United States Patent
Perrot et al.

(10) Patent No.: US 10,766,966 B2
(45) Date of Patent: *Sep. 8, 2020

(54) CD73 BLOCKADE

(71) Applicant: INNATE PHARMA, Marseilles (FR)

(72) Inventors: Ivan Perrot, Cassis (FR); Carine Paturel, Marcy l'Etoile (FR); Laurent Gauthier, Marseilles (FR)

(73) Assignee: INNATE PHARMA, Marseilles (FR)

( * ) Notice: Subject to any disclaimer, the term of this patent is extended or adjusted under 35 U.S.C. 154(b) by 403 days.

This patent is subject to a terminal disclaimer.

(21) Appl. No.: 15/517,991

(22) PCT Filed: Oct. 9, 2015

(86) PCT No.: PCT/EP2015/073370
§ 371 (c)(1),
(2) Date: Apr. 10, 2017

(87) PCT Pub. No.: WO2016/055609
PCT Pub. Date: Apr. 14, 2016

(65) Prior Publication Data
US 2018/0237536 A1    Aug. 23, 2018

Related U.S. Application Data

(60) Provisional application No. 62/062,323, filed on Oct. 10, 2014, provisional application No. 62/118,549, filed on Feb. 20, 2015, provisional application No. 62/133,597, filed on Mar. 16, 2015, provisional application No. 62/188,881, filed on Jul. 6, 2015.

(51) Int. Cl.
*C07K 16/00* (2006.01)
*C07K 16/28* (2006.01)
*C07K 16/40* (2006.01)
*C07K 16/30* (2006.01)

(52) U.S. Cl.
CPC .......... *C07K 16/2896* (2013.01); *C07K 16/30* (2013.01); *C07K 16/40* (2013.01); *C07K 2317/21* (2013.01); *C07K 2317/24* (2013.01); *C07K 2317/33* (2013.01); *C07K 2317/34* (2013.01); *C07K 2317/41* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2018/0030144 A1    2/2018  Chanteux et al.

FOREIGN PATENT DOCUMENTS

| WO | WO 2016/131950 | 8/2016 |
| WO | WO 2017/064043 | 4/2017 |

OTHER PUBLICATIONS

Arias et al. (J. of Cell Biol. vol. 136, No. 2, Jan. 1997, 421-431). (Year: 1997).*
Airas, L. et al. "Differential Regulation and Function of CD73, a Glycosyl-Phosphatidylinositol-linked 70-kD Adhesion Molecule, on Lymphocytes and Endothelial Cells" *The Journal of Cell Biology*, Jan. 27, 1997, pp. 421-431, vol. 136, No. 2.
Flocke, K. et al. "Isolation and characterization of 5'-nucleotidase of a human pancreatic tumor cell line" *Biochimica et Biophysica Acta*, Jan. 29, 1991, pp. 273-281, vol. 1076, No. 2.
Flocke, K. et al. "Monoclonal antibodies against 5'-nucleotidase from a human pancreatic tumor cell line: their characterization and inhibitory capacity on tumor cell adhesion to fibronectin substratum" *European Journal of Cell Biology*, Jun. 1, 1992, pp. 62-70, vol. 58, No. 1.
Gurd, J. W. et al. "Distribution of Liver Plasma Membrane 5' Nucleotidase as Indicated by Its Reaction with Anti-Plasma Membrane Serum" *Archives of Biochemistry and Biophysics*, Sep. 1, 1974, pp. 305-311, vol. 164, No. 1.
Sadej, R. et al. "Ecto-5'-Nucleotidase (eN, CD73) is Coexpressed with Metastasis Promoting Antigens in Human Melanoma Cells" *Nucleosides, Nucleotides, and Nucleic Acids*, Jun. 1, 2006, pp. 1119-1123, vol. 25. Nos. 9-11.
Häusler, S. F. M. et al. "Anti-CD39 and anti-CD73 antibodies A1 and 7G2 improve targeted therapy in ovarian cancer by blocking adenosine-dependent immune evasion" *American Journal of Translational Research*, Jan. 15, 2014, pp. 129-139, vol. 6, No. 2.
Written Opinion in International Application No. PCT/EP2015/073370, dated Jan. 26, 2016, pp. 1-9.
Claims as filed for U.S. Appl. No. 15/767,661, 2018, pp. 1-6.

* cited by examiner

*Primary Examiner* — Meera Natarajan
(74) *Attorney, Agent, or Firm* — Saliwanchik, Lloyd & Eisenschenk

(57) ABSTRACT

This disclosure relates to antibodies that bind an epitope present on CD73 expressed at the surface of cells, including tumor cells, and that inhibit the enzymatic (ecto-5' nucleotidase) activity of the CD73 enzyme. Such agents can be used for the treatment of diseases such as cancers.

12 Claims, 9 Drawing Sheets

Specification includes a Sequence Listing.

OPEN

CLOSED

OPEN

CLOSED

CD73 BLOCKADE

CROSS-REFERENCE TO RELATED APPLICATIONS

This application is the U.S. national stage application of International Patent Application No. PCT/EP2015/073370, filed Oct. 9, 2015, which claims the benefit of U.S. Provisional Application No. 62/062,323, filed 10 Oct. 2014; U.S. 62/118,549 filed 20 Feb. 2015; U.S. 62/133,597 filed 16 Mar. 2015; and U.S. 62/188,881 filed 6 Jul. 2015; all of which are incorporated herein by reference in their entirety; including any drawings.

REFERENCE TO SEQUENCE LISTING

The present application is being filed along with a Sequence Listing in electronic format. The Sequence Listing is provided as a file entitled "CD73-1_ST25", created 8 Oct. 2015, which is 24 KB in size. The information in the electronic format of the Sequence Listing is incorporated herein by reference in its entirety.

FIELD OF THE INVENTION

The present invention relates to antigen-binding compounds (e.g. antibodies) that inhibit CD73. The invention also relates to cells producing such compounds; methods of making such compounds, and antibodies, fragments, variants, and derivatives thereof; pharmaceutical compositions comprising the same; methods of using the compounds to diagnose, treat or prevent diseases, e.g. cancer.

BACKGROUND

CD73 (ecto-5'-nucleotidase) is a 70-kDa glycosylphosphatidylinositol (GPI)-anchored protein normally expressed on endothelial cells and subsets of hematopoietic cells. CD73, together with CD39, regulates adenosine triphosphate (ATP) metabolism. CD39 (NTPDase-1) converts ATP into AMP, with only trace amounts of ADP being released, while CD73 catalyzes the conversion of AMP to adenosine.

Adenosine triphosphate (ATP) and its metabolites AMP and adenosine, have important roles in cellular metabolism, signalling and immune homeostasis. The release of extracellular adenosine triphosphates (ATP) in response to cell death or cellular stress acts to activate immune responses. However, its metabolite adenosine has immunosuppressive activity. Extracellular adenosine accumulates in cancerous tissues and constitutes an important mechanism of tumor immune escape. Among other effects, tumor-derived adenosine profoundly inhibits infiltrating effector T cells through adenylyl cyclase-activating A2A receptors.

CD73 expression has been reported in a range of tumor cells, including leukemia, bladder cancer, glioma, glioblastoma, ovarian cancer, melanoma, prostate cancer, thyroid cancer, esophageal cancer and breast cancer. CD73 expression has also been associated with a prometastatic phenotype in melanoma and breast cancer. It has been shown that therapy with an antibody that binds murine CD73 can inhibit breast tumor growth and metastasis in mice (Stagg, et al. (2010) Proc. Natl. Acad. Sci. USA 104:1547-1552). Antibodies however generally do not cross react with human and mouse CD73, complicating the study of the antibodies and the biological functions of CD73. It has been shown that genetic deletion of A2A receptors can induce T cell-dependent tumor rejection (Ohta, et al., (2006) Proc Natl Acad Sci USA 103:13132-13137). Knock-down using siRNA or over-expression of CD73 on tumor cells can modulate tumor growth and metastasis (Beavis et al (2013 Proc. Natl. Acad. Sci. USA 110:14711-716; Stagg et al. (2010), supra; Jin et al. (2010) Cancer Res. 70: 2245-55). CD73–/– mice are protected from transplanted and spontaneous tumors (Stagg et al. (2010) Cancer Res. 71: 2892-2900). In humans, high CD73 expression had been shown to be a negative prognostic for triple negative breast cancer (Loi et al (2013 Proc. Natl. Acad. Sci. USA 110: 11091-11096).

Despite the long-standing interest in CD73 as a therapeutic target, the activity required of an agent to target CD73 in vivo has not been fully elucidated. While CD73 is expressed on tumor cells, it is also expressed on different cells of the immune system, notably CD4 and CD8 T cells, as well as B cells. While some antibodies have been reported to bind human CD73 and increase the activity or proliferation of T cells or modify the migration of tumor cells, it remains to be clarified how such antibodies function since such T cell modulation and CD73-mediated transmission of co-stimulatory signals have been reported to be possible without dependence on the ecto-5'nucleotidase activity of CD73 (Gutensohn et al. 1995 Cell Immunol. 161:213-217). Consequently, antibodies generically referred to as CD73 inhibitors may not act by modulating the ecto-5'nucleotidase activity of CD73. One antibody, 7G2 (mIgG2 isotype, Life Technologies), has been reported to inhibit CD73, however this antibody does not bind cell surface CD73 in flow cytometry, or at best only with very low affinity. Another antibody that binds CD73, clone AD2 (mouse IgG1 isotype), has been reported to cause receptor clustering and internalization but have minimal effect on enzymatic activity. Yet another agent, 1E9 (mouse IgG3 isotype, Santa Cruz Biotechnology, Inc.), is reported to promote T cell signaling independently of enzymatic inhibition. A further mAb, 4G4 (IgG1 isotype, Novus Biologicals), is reported to induce CD73 shedding from the T cell surface. Only one agent, although not further characterized, was reported to have partial ability to block enzymatic in an assay using recombinant CD73 (Sachsenmeier et al. ((2012) J. Biomed. Screening 17:993-998), and was later described as an antibody that induces intracellular internalization (Rust et al. (2013) Mol. Cancer 12:11). Additionally, one further complicating factor is that the antibodies described in the literature have generally been of murine isotypes that are capable of being bound by Fcγ receptors, making it difficult to separate any potential blocking effect from Fc-mediated effects. Anti-CD73 antibodies that are bound by Fcγ receptors can for example mediate depletion (e.g. by ADCC) of CD73-expressing tumor cells (and possibly CD73-expressing immune suppressor cells), and/or may elicit the production of pro-inflammatory cytokines rather than any true blocking effect. Consequently, the mode of action of antibodies remains elusive.

Thus, despite the interest in targeting CD73, the characteristics of the most effective anti-CD73 antibodies remains to be determined. No antibodies have been reported that bind the CD73 active site. CD73 expression on different cell types, including immune cells and tumor cells, combined with use of antibodies that either do not actually block CD73 or are not pure blockers, create a complex setting for evaluation of the underlying activity of antibodies. New assays and antibodies are needed.

SUMMARY OF THE INVENTION

The inventors have discovered antibodies that bind an epitope present on CD73 expressed at the surface of cells, including tumor cells, and that inhibit the enzymatic (ecto-5′ nucleotidase) activity of the CD73 enzyme. The antibodies can inhibit the enzymatic activity of membrane-bound CD73 protein expressed at the surface of cells. Advantageously, these antibodies can be used as pure CD73 blocking antibodies, e.g., they inhibit the enzymatic activity of membrane-bound CD73 protein expressed at the surface of cells without substantially binding Fcγ receptors and/or without substantially directing ADCC toward a CD73-expressing cell. Optionally, the antibodies retain an Fc domain and retain binding to human FcRn.

Optionally, in contrast to some antibodies capable of depleting CD73-expressing tumor cells (which, e.g., can provide full efficacy at concentrations equal or substantially lower than that which provides receptor saturation), the antibodies can advantageously be used as pure blockers and administered in an amount effective to neutralize the enzymatic activity of CD73 for a desired period of time, e.g. 1 week, 2 weeks, a month, until the next successive administration of anti-CD73 antibody.

Optionally the antibodies are pure blockers and directed to neutralize the enzymatic activity of CD73 in the tumor environment. Optionally the antibodies comprise a modified Fc domain, e.g. to decrease protease sensitivity (e.g. toward proteases such as MMPs in the tumor environment) and/or to decrease binding to human Fcγ receptors (e.g., CD16).

The disclosure in one aspect provides assays that can be used to identify true CD73 function blocking antibodies. As shown herein, in previous soluble enzyme blocking assays, the vast majority of antibodies found to block as bivalent antibodies are false positives, while monovalent binding antibodies may have no or little blocking activity, possibly due the inability to block the active site or act as allosteric inhibitors when not binding to each CD73 polypeptide within the CD73 dimer. Previous cellular assays could not distinguish between mechanisms of action, and the antibodies reported to decrease CD73 activity may combine multiple mechanisms of action, for example induction of receptor internalization, receptor shedding and/or Fcγ receptor-mediated effects. Because residual CD73 enzymatic activity can result in sufficient adenosine generation to mediate immunosuppressive effects, high levels of antibody-mediated enzyme blockade are advantageous in order to mediate a therapeutic effect.

The disclosure in one aspect provides antibodies that bind an epitope present on human CD73 polypeptide expressed at the surface of cells, including but limited to tumor cells, and that inhibit the enzymatic (ecto-5′ nucleotidase) activity of the CD73 enzyme.

The disclosure in one aspect provides antibodies that can inhibit the enzymatic activity of soluble recombinant CD73 protein.

The antibodies of the disclosure do not cause intracellular internalization of, or more generally down-modulation of, cell surface-expressed CD73 and/or do not depend thereupon for their CD73 inhibitory activity. The antibodies of the disclosure can provide greater inhibitory potency (the ability to substantially neutralize CD73 enzymatic activity) than antibodies that inhibit CD73 by causing CD73 internalization. As opposed to antibodies that inhibit soluble CD73 by other mechanisms (e.g. causing CD73-antibody oligomer formation), the antibodies of the disclosure are capable of inhibiting the enzymatic activity of CD73 at all concentrations, including at higher (e.g. 10 fold) excess of antibody:enzyme. Furthermore, unlike antibodies that bind an epitope on recombinant CD73 that may be modified or absent on cell surface CD73 (e.g. antibody 7G2) or with affinity that is too low to translate into efficacy in CD73-expressing cells, the present antibodies bind with high affinity to an epitope that is present and/or remains intact on cell surface CD73, providing the antibodies with the ability to potently neutralize of the enzymatic activity of cellular CD73. The present antibodies inhibit CD73 enzymatic activity in cells but can optionally also inhibit the ecto-5′nucleotidase activity of soluble recombinant CD73 (as observed in a cell-free assay using soluble dimeric CD73 polypeptide).

Furthermore, exemplary antibodies (see, e.g., antibodies 11E1, 6E1, 3C12 and 8C7) are disclosed herein which are believe to be capable of acting as allosteric inhibitors of CD73 expressed by cells, e.g. they inhibit the activity of the human CD73 polypeptide without binding to the enzymatic active site of the CD73 polypeptide, and/or that they are non-competitive inhibitors of CD73, e.g., they inhibit the activity of the human CD73 polypeptide without detectably reducing binding between the CD73 polypeptide and a natural substrate thereof. The exemplary antibodies lose binding to CD73 mutants having a substitution at residues A99, E129, K133, E134 and A135. In view of binding of the exemplary antibodies to CD73 both in the presence and absence of the CD73 active site inhibitor APCP, their epitope on CD73 appears to be present on CD73 not only in the "open" conformation when not bound to substrate but also in the "closed" conformation when bound to a substrate (e.g. a natural substrate such as AMP or an inhibitor or other compound that binds the active site such as an AMP analogue adenosine 5′-($\alpha$,$\beta$-methylene)diphosphate (APCP)).

Accordingly, in one aspect the disclosure provides an allosteric inhibitor of the CD73 polypeptide. In one aspect, the allosteric inhibitor is an antibody. In one aspect provides an antibody that binds human CD73 polypeptide expressed at the surface of a cell, including but limited to tumor cells, and that inhibit the enzymatic (ecto-5′ nucleotidase) activity CD73 polypeptide, wherein the antibody is an allosteric inhibitor of the CD73 polypeptide.

Moreover, exemplary antibodies are described herein that bind to an epitope on CD73 that is present on the same face when CD73 is present as a CD73 dimer, e.g., potentially permitting an antibody to bind bivalently to one CD73 dimer, notably in "closed" position where the binding sites are spatially further apart. In view of binding to ligand-bound CD73, the antibodies described herein may be useful for binding to CD73 when bound to AMP, e.g., in the tumor environment where upstream ADP and/or AMP are present at significant levels prior to treatment). The tumor microenvironment can be characterized by any appropriate parameter, for example high levels of ADP (e.g. generated by dying cells), taken up by CD39 on stromal and cellular infiltrate (e.g. TReg cells) to yield high levels of AMP, as well as more generally by AMP, adenosine, by presence or levels of CD39 expression or CD39-expressing cells, by presence or levels of CD73 expression or CD73-expressing cells, by presence or levels of adenosine receptor expression or adenosine-receptor expressing cells. Thus, CD73 molecules in the tumor environment may be in the substrate-bound conformation, and the ability to bind and inhibit substrate-bound cellular CD73 (e.g. cells expressing CD73 pre-incubated with substrate such as AMP) in addition to non-substrate bound CD73 may provide greater ability to inhibit CD73 in vivo. Optionally, levels of ADP or AMP (and/or ATP or adenosine) can be assessed in the tumor environment prior to treatment. The antibodies may have a particular advantage for treatment in an individual having significant levels (e.g. high levels, compared to a reference) ADP, AMP, ATP or adenosine in the tumor sample.

Accordingly, in one aspect the disclosure provides an antibody that binds human CD73 polypeptide expressed at the surface of cells and that inhibits the enzymatic (ecto-5' nucleotidase) activity of the CD73 polypeptide, wherein the antibody is capable of binding bivalently to a single CD73 polypeptide dimer (a soluble CD73 polypeptide dimer or a CD73 polypeptide dimer expressed by a cell). Optionally, the antibody binds with a first antigen binding domain to a first CD73 polypeptide within the dimer and with a second antigen binding domain to a second CD73 polypeptide. In one aspect the antibody is an allosteric inhibitor of the CD73 polypeptide.

Accordingly, in another aspect the disclosure provides an antibody that binds human CD73 polypeptide expressed at the surface of cells and that inhibits the enzymatic (ecto-5' nucleotidase) activity of the CD73 polypeptide, wherein the antibody is capable of binding the CD73 polypeptide in the substrate-bound conformation.

Despite efforts in the literature to screen for CD73-inhibition antibodies, existing antibodies do not neutralize cellular CD73, or at best cause CD73 down-modulation. The inventors provide herein an explanation why these antibodies no longer inhibit CD73 in cells: antibodies that are capable of binding CD73 homodimers in bivalent manner and that inhibit recombinant CD73 in solution may be causing oligomerization of the CD73 polypeptides and anti-CD73 antibodies into complexes (e.g., structures containing more than two or more antibodies and two or more CD73 dimers), presenting difficulties to distinguish an true inhibitor from a false positive.

Through design of improved assay methods conducted at higher excess of antibody:enzyme, we present herein antibodies with bivalent binding to CD73 that have no dependence upon oligomerization. In particular, the anti-CD73 antibodies provided herein are capable of inhibiting the enzymatic activity of soluble human dimeric CD73 polypeptide when the antibodies are in a setting/configuration where they not capable of forming oligomers, e.g. when they are provided at a substantial molar excess (e.g. at least 10-fold, 20-fold, 100-fold, etc.) to the CD73 polypeptide dimers. Antibodies that function by causing oligomerization fail to inhibit CD73 when the antibodies provided at a substantial molar excess to the CD73 polypeptide dimers. The antibodies furthermore bind an epitope on CD73 that is maintained when CD73 is expressed at the cell surface. Through use of this assay, antibodies can also be identified that bind bivalently to a single CD73 dimer; such antibodies may have improved CD73-binding and CD73 blocking activity in vitro and vivo in CD73-expressing cells. The antibodies identified by these methods were then tested in cellular enzymatic activity assays using purified antibody, and found to neutralize the enzymatic activity of cellular CD73. Antibodies that inhibit CD73 by inducing internalization or that lose significant binding to cellular CD73 were less potent and were not able to neutralize enzymatic activity, providing at best only partial inhibition of the enzymatic activity of CD73 in cells.

The epitope on CD73 bound by these antibodies is present on CD73 polypeptides as expressed by a range of cells, e.g. cancer cells, CD4 T cells, CD8 T cells, B cells, transfected cells, and binds with high affinity as determined by flow cytometry. For example, an antibody can be characterized by an $EC_{50}$ as determined by flow cytometry, of no more than 5 µg/ml, optionally no more than 2 µg/ml, no more than 1 µg/ml, no more than 0.5 µg/ml, no more than 0.1 µg/ml or no more than 0.05 µg/ml, for binding to cells that express at their surface a CD73 polypeptide. In one embodiment the cells are cells that are made to express CD73 at their surface. In one embodiment the cells are cells that endogenously express CD73 at their surface, e.g. cancer cells, leukemia cells, bladder cancer cells, glioma cells, glioblastoma cells, ovarian cancer cells, melanoma cells, prostate cancer cells, thyroid cancer cells, esophageal cancer cells or breast cancer cells.

In one embodiment, the CD73 neutralizing antibodies can be characterized by being capable of causing a decrease in cells' 5'-ectonucletidase activity of CD73 by at least 60%, 75% or 80%. In one embodiment, the CD73-neutralizing antibodies can be characterized by an $EC_{50}$ for inhibition of 5'-ectonucletidase activity of CD73 expressed by a cell of no more than 1 µg/ml, optionally no more than 0.5 µg/ml, optionally no more than 0.2 µg/ml.

Optionally, inhibition of 5'-ectonucletidase activity of CD73 expressed by a cell is determined by assessing neutralization of 5' ectonucleotidase activity in MDA-MB-231 cells by quantifying hydrolysis of AMP to adenosine (see, e.g., Example 5).

The epitope on CD73 bound by the neutralizing antibodies disclosed herein does not result in the down-modulation of CD73 expression on cells (and, e.g., does not cause clustering and internalization of the antibody-CD73 complex), including when full length antibodies are used that bind CD73 in bivalent manner. The anti-CD73 antibody thus remains bound, together with CD73, at the cell surface. In view of the broad tissue expression of CD73, antibodies that do not trigger CD73 down-modulation and/or internalization may provide improved pharmacological properties and greater amounts of antibody in the tumor microenvironment.

In one embodiment, provided is an isolated antibody that specifically binds human CD73 (e.g. a polypeptide comprising the amino acid sequence of SEQ ID NOS: 1 or 2) and which neutralizes the 5'-ectonucleotidase activity of a homodimeric human CD73 polypeptide in solution. In one embodiment, provided is an antibody that binds and inhibits the enzymatic activity of a soluble human CD73 polypeptide, notably an antibody that neutralizes the CD73-mediated catabolism of AMP to adenosine. In one embodiment, the antibody binds CD73 in bivalent manner. In one embodiment, the antibody is a non-depleting antibody e.g., an Fc silent antibody. In one embodiment, the antibody neutralizes CD73 in solution without reliance on induction of CD73 polypeptide:anti-CD73 antibody oligomers.

In one embodiment, provided is an isolated antibody that specifically binds human CD73 at the surface of a cell and that is capable of neutralizing the 5'-ectonucletidase activity of a soluble human CD73 polypeptide. In one embodiment, the antibody does not induce the oligomerization of the soluble CD73.

In one embodiment, provided is an isolated antibody that specifically binds human CD73 at the surface of a cell and that is capable of neutralizing the 5'-ectonucletidase activity of cellular CD73 (CD73 expressed by cells). In one embodiment, provided is an isolated antibody that specifically binds and neutralizing the 5'-ectonucletidase activity of a human CD73 at the surface of a cell and that is not internalized into CD73-expressing cells upon binding to CD73. The antibody does not cause multimerization and subsequence internalization of CD73. In one embodiment, provided is an antibody that binds and is capable of inhibiting the enzymatic activity of a recombinant human CD73 polypeptide in solution, wherein said antibody is not internalized into CD73-expressing cells. In one embodiment, the non-internalizing antibody binds CD73 in bivalent manner. In one embodiment, the antibody is a non-depleting antibody, e.g., an Fc silent antibody. The antibody is capable of neutralizing the 5'-ectonucleotidase activity of a dimeric human CD73 polypeptide in solution, moreover without reliance on induction of CD73 polypeptides: anti-CD73 antibodies oligomers.

In one embodiment, provided is an antibody that specifically binds bivalently to human CD73 polypeptides and inhibits the enzymatic activity of cellular human CD73 (and optionally further recombinant soluble human CD73), wherein said antibody is not internalized into CD73-expressing cells. Preferably, the antibody substantially lacks Fcγ receptor binding (e.g. via its Fc domain).

In one aspect, provided is an isolated antibody that specifically binds human CD73 at the surface of a cell pre-incubated with AMP, and that is capable of neutralizing the 5'-ectonucletidase activity thereof. Optionally, neutralizing the 5'-ectonucletidase activity is determined by assessing neutralization of 5' ectonucleotidase activity in MDA-MB-231 cells by quantifying hydrolysis of AMP to adenosine (see, e.g., Example 5).

In any of the embodiments herein, the antibody can be characterized by being capable of binding a human CD73 polypeptide whose active site is occupied by a substrate, e.g. AMP, APCP. In any of the embodiments herein, the antibody can be characterized by being capable of inhibiting the 5'-ectonucletidase activity of a cell expressing CD73 when such cell has been pre-incubated with AMP. The invention also results, inter alia, from the discovery of an epitope on human CD73 that permits highly-effective targeting for neutralizing CD73 activity in cells and individuals suffering from cancer. The antibodies compete for one another for binding to CD73, (but did not compete with reference soluble CD73 blocking antibodies) suggesting a region on CD73 which is particularly suitable for inhibition of enzymatic activity of CD73 and that remains present on the CD73 polypeptide when expressed at the cell surface. Advantageously, the epitope is present on each of human and non-human primate CD73, as expressed on the cell surface, as well as on CD73 as expressed by cancer cells.

In one aspect, provided is an anti-CD73 antibody that binds a common antigenic determinant present on both soluble CD73 and CD73 expressed at the cell surface.

In one aspect, provided is an anti-CD73 antibody that binds a common antigenic determinant present on CD73 when it is "open" conformation (when CD73 active site is not occupied by/bound to a substrate, e.g. AMP, APCP) and "closed" CD73 when it is "closed" conformation (when CD73 active site is occupied by/bound to a substrate, e.g. AMP, APCP).

In one aspect, provided is an anti-CD73 antibody that binds an antigenic determinant within each CD73 polypeptide chain within a CD73 dimer, e.g., wherein the antigenic determinants are present on a common face of the CD73 dimer.

In one aspect, provided is an anti-CD73 antibody that binds that bind an epitope on CD73 comprising one, two, three, four or five of the residues selected from the group consisting of A99, E129, K133, E134, and A135 (with reference to SEQ ID NO: 1).

In one aspect, provided is an anti-CD73 antibody that has reduced binding to a CD73 polypeptide having a mutation at a residue selected from the group consisting of: A99, E129, K133, E134, and A135 (with reference to SEQ ID NO: 1); optionally, the mutant CD73 polypeptide has the mutations: A99S, E129A, K133A, E134N, and A135S.

Provided in one aspect provided is an anti-CD73 antibody that competes for binding to an epitope on CD73 bound by 11E1, 8C7, 3C12 and/or 6E1, (e.g., that competes for binding to an epitope on a CD73 polypeptide with an antibody having the heavy and light chain CDRs or variable regions of any of 11E1, 8C7, 3C12 or 6E1).

In one aspect of any of the embodiments herein, provided is an antigen-binding compound that binds the same epitope and/or competes for binding to a CD73 polypeptide with monoclonal antibodies 11E1, 8C7, 3C12 and/or 6E1 (e.g., that competes for binding to a CD73 polypeptide with an antibody having the heavy and light chain CDRs or variable regions of any of 11E1, 8C7, 3C12 or 6E1). In one embodiment, provided is antigen-binding compound binds the same epitope and/or competes for binding to a CD73 polypeptide with an antibody selected from the group consisting of:
 (a) an antibody having respectively a VH and VL region of SEQ ID NOS: 3 and 4 (11E1);
 (b) an antibody having respectively a VH and VL region of SEQ ID NOS: 21 and 22 (6E1)
 (c) an antibody having respectively a VH and VL region of SEQ ID NOS: 28 and 29 (8C7); and
 (d) an antibody having respectively a VH and VL region of SEQ ID NOS: 36 and 37 (3C12).

In one embodiment, an anti-CD73 antibody binds an epitope comprising one, two or three amino acid residues selected from the group consisting of the amino acid residues on CD73 bound by 11E1, 6E1, 3C12 or 8C7. In one embodiment, the amino acid residues on CD73 are selected from the group consisting of the residues listed in Table 1.

In one aspect of any of the embodiments herein, the antibody may have a heavy and/or light chain having one, two or three CDRs of the respective heavy and/or light chain of an antibody selected from the group consisting of antibody 11E1, 6E1, 3C12 and 8C7.

In any of the embodiments herein, the anti-CD73 antibodies can be characterized by binding to human CD73 polypeptides expressed on the surface of a cell (e.g. a tumor cell, a cell made to express CD73, e.g. an MDA-MB-231 tumor cell line, or a recombinant host cell made to express CD73, as shown in the Examples), and optionally further wherein the antibody binds with high affinity as determined by flow cytometry. For example, an antibody can be characterized by an $EC_s$, as determined by flow cytometry, of no more than 5 µg/ml, optionally no more than 1 µg/ml, no more than 0.5 µg/ml, no more than 0.1 µg/ml or no more than 0.05 µg/ml, for binding to cells that express at their surface a CD73 polypeptide, e.g. tumor cells expressing CD73, cells expressing at their surface a CD73 polypeptide, lymphocytes expressing CD73, etc. Optionally, an antigen-binding compound has an $EC_{50}$ of no more than 1 µg/ml, optionally no more than 0.5 µg/ml, no more than 0.1 µg/ml, or no more than 0.05 µg/ml for binding to (i) cells expressing at their surface human CD73 (e.g. a polypeptide having the amino acid sequence of SEQ ID NO: 1) and/or (ii) cells expressing at their surface human non-human primate CD73 (e.g. a cynomolgus monkey CD73).

In one aspect of any of the embodiments herein, the anti-CD73 antibody is a tetrameric antibody comprising two heavy and two light chains, the heavy chains comprising Fc regions of human isotype and which substantially lack binding to human Fcγ receptors (e.g. CD16A, CD16B, CD32A, CD32B and/or CD64).

In one embodiment, the antibodies are administered to an individual having a cancer in an amount and frequency sufficient to neutralize the activity of CD73 in the tumor microenvironment. In one embodiment, the antibodies are administered in an amount and frequency sufficient to decrease the generation and/or concentration of adenosine in the tumor microenvironment. In one embodiment, the antibodies are administered in an amount and frequency sufficient to increase the generation and/or concentration of ATP in the tumor microenvironment. In one embodiment, the antibodies are administered in an amount and frequency sufficient to neutralize the activity of CD73 expressed by tumor cells. In one embodiment, the antibodies are administered in an amount and frequency sufficient to neutralize the activity of CD73 expressed by CD4 T cells, CD8 T cells and/or B cells.

The antibodies will be useful in inhibiting CD73-mediated catabolism of AMP to adenosine, e.g. decreasing the concentration of adenosine in the tumor microenvironment. These antibodies will therefore be useful in reversing the immunosuppressive effect of CD73 and/or adenosine on T cells, B cells and other cells that express adenosine receptors, for example in the treatment of cancer. In one embodiment, the anti-CD73 antibody neutralizes adenosine-mediated inhibition of proliferation, cytokine production, cytotoxicity and/or NFκB activity in T cells.

Because the CD73-mediated catabolism of AMP to adenosine is irreversible, whereas the catabolism of ATP to ADP and ADP to AMP by CD39 is reversible (by NDK kinase and adenylate kinase, respectively), the antibodies that block the irreversible CD73-mediated catabolism will increase the pool of AMP, thereby being of use in increasing the concentrations of ADP and ATP, e.g. in the tumor microenvironment. The antibodies can be useful to increase the formation of ADP from AMP and the formation of ATP from ADP. Since ATP has immune activating roles, the anti-CD73 antibodies can be useful in activating T cells, for example in the treatment of cancer.

The antibodies will be useful in inhibiting the production, amounts and/or concentrations of adenosine into the tumor microenvironment The antibodies that neutralize the activity of a soluble human CD73 polypeptide dimer can further neutralize CD73 in any other suitable context, e.g. in a reporter cell made to express CD73, in a T cell, etc.

Provided is a method for treating an individual, the method comprising administering to an individual (e.g. an individual having a disease, a tumor, etc.) a therapeutically active amount of any of the anti-CD73 antigen binding compounds described herein. In one aspect provided is a method for treating an individual, the method comprising, consisting essentially of or consisting of administering to an individual (e.g. an individual having a disease, a tumor, etc.) a therapeutically active amount of an antigen binding compound of the disclosure that inhibits a CD73 polypeptide. In one embodiment, the antibody inhibits a CD73 polypeptide in a cellular and optionally further a non-cellular assay, e.g. a recombinant CD73, a soluble CD73. Preferably the compound is a non-depleting antibody (an antibody that does not deplete cells to which it binds, e.g., an Fc silent antibody). Optionally, the compound binds to CD73 in bivalent manner. Optionally, the antibody is a chimeric, humanized or human antibody. Optionally, the antibody comprises a heavy chain constant region of IgG4 isotype.

In one aspect provided is a method for decreasing adenosine produced by a CD73-expressing cell (e.g. an immune cell and/or a tumor cell in an individual), or a method for neutralizing of the enzymatic activity of cellular CD73, the method comprising, consisting essentially of or consisting of: bringing the CD73-expressing cell into contact with an antigen binding compound of the disclosure that inhibits CD73. In one embodiment, the step of bringing the CD73-expressing cell into contact with an antigen binding compound of the disclosure comprises administering to an individual a therapeutically active amount of an antigen binding compound that inhibits a CD73. In one embodiment the individual has a cancer.

In one aspect provided is a method for decreasing adenosine present in the tumor environment (e.g. in an individual), the method comprising, consisting essentially of or consisting of: administering to an individual a therapeutically active amount of an antigen binding compound that inhibits a CD73 polypeptide. In one embodiment the individual has a cancer.

In one embodiment, the active amount of an antigen binding compound that inhibits a CD73 polypeptide is an amount effective to achieve and/or maintain (e.g. until the subsequent administration of antigen binding compound) a blood concentration of at least the $EC_{50}$, optionally the $EC_{70}$, optionally substantially the $EC_{100}$, for inhibition of CD73-mediated catabolism of AMP to adenosine in an individual. In one embodiment, the active amount of an antigen binding compound that inhibits a CD73 polypeptide is an amount effective to achieve the $EC_{50}$, optionally the $EC_{70}$, optionally substantially the $EC_{100}$, for inhibition of CD73-mediated catabolism of AMP to adenosine in an extravascular tissue of an individual. In one embodiment, the active amount an antigen binding compound that inhibits a CD73 polypeptide is an amount effective to achieve the ECs, optionally the $EC_{70}$, optionally substantially the $EC_{100}$, for inhibition of CD73-mediated catabolism of AMP to adenosine in an individual. In one embodiment, the active amount of an antigen binding compound that inhibits a CD73 polypeptide is between 1 and 20 mg/kg body weight. In one embodiment, the active amount is administered to an individual weekly, every two weeks, monthly or every two months.

Optionally the individual is human having or who is susceptible to having a cancer.

The antibodies are optionally characterized by binding affinity ($K_D$) for a human CD73 polypeptide of less than (better than) $10^{-9}$M, preferably less than $10^{-10}$ M, or preferably less than $10^{-11}$M, and/or by binding human CD73 with an EC50 lower than (better binding than) 1 µg/ml, preferably wherein the antibody has an $EC_{50}$ of no more than 0.5 µg/ml, optionally no more than 0.2 µg/ml, optionally no more than 0.1 µg/ml, for binding to cells (e.g. tumor cells) expressing human CD73 at the cell surface.

The antibodies are optionally chimeric, human or humanized antibodies.

The antibodies are optionally characterized by an $EC_{50}$ for neutralization of the enzymatic activity of CD73 in CD73-expressing cells of less than (better than) 1 µg/ml, optionally less than 0.5 µg/ml.

In one embodiment, the antibody is a monoclonal antibody or a fragment thereof that retains binding specificity and ability to neutralize the enzymatic activity of CD73. In one embodiment, the antibody is an IgG1, IgG2, IgG3, or IgG4 antibody. For example, the antibody may be an antibody comprising an Fc domain of human IgG4 isotype, or an antibody comprising an Fc domain of any human IgG isotype (e.g. IgG1, IgG2, IgG3, or IgG4) modified to reduce binding between the Fc domain and an Fcγ receptor (e.g. CD16). Preferably, the antigen-binding compound does not comprise an Fc domain capable of inducing antibody mediated cellular cytotoxicity (ADCC) and/or CDC; optionally the antigen-binding compound does not comprise an Fc domain capable of substantially binding to a FcγRIIIA (CD16) polypeptide (e.g., comprises an Fc domain not capable of substantially binding to a FcγRIIIA (CD16) polypeptide; lacks an Fc domain (e.g. lacks a CH2 and/or CH3 domain; comprises an Fc domain of IgG4 isotype). In one embodiment, the Fc domain (e.g. of human IgG1, IgG2, IgG3 or IgG4 isotype) comprises an amino acid modification (e.g. substitution) compared to a wild-type Fc domain, wherein the substitution reduces the ability of the Fc domain (or antibodies containing it) to bind to an Fcγ receptor (e.g. CD16) and/or to bind complement. Optionally, if an Fc domain of IgG4 isotype is present, such Fc domain may comprise a stabilizing mutation to decrease formation of half-antibodies such as a mutation in the hinge, e.g. a S241P (S228P) mutation. Optionally the antigen-binding compound consists of or comprises a Fab, Fab', Fab'-SH, F (ab')2, Fv, a diabody, single-chain antibody fragment, or a multispecific antibody comprising multiple different antibody fragments. In one embodiment, the antigen-binding compound is not linked to a toxic moiety.

Also provided are nucleic acids encoding the human or humanized antibody or antibody fragment having any of the foregoing properties, a vector comprising such a nucleic acid, a cell comprising such a vector, and a method of producing a human anti-CD73 antibody, comprising culturing such a cell under conditions suitable for expression of the anti-CD73 antibody. The disclosure also relates to compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers). The disclosure further relates various new and useful methods making and using such antibodies, nucleic acids, vectors, cells, organisms, and/or compositions, such as in the modulation of CD73-mediated biological activities, for example in the treatment of diseases related thereto, notably cancers.

The disclosure also provides methods of producing or testing an antibody which binds and neutralizes the enzymatic activity of CD73, said method comprising the steps of:
  (a) providing a plurality of antibodies that bind a CD73 polypeptide,
  (b) bringing each of said antibodies into contact (e.g., separately from one another) with a soluble CD73 polypeptide (e.g. in a cell-free assay, e.g. in the presence of AMP), and
  (c) selecting an antibody (e.g. those of step (b)) that neutralizes the enzymatic activity of said soluble CD73 polypeptide. In one embodiment, the antibodies are capable of binding CD73 in bivalent manner, e.g. the antibodies are full length IgG antibodies. Optionally, step (b) comprises bringing each of said antibodies into contact with a soluble CD73 polypeptide in a cell-free assay, wherein antibodies are provided in a molar excess of antibody (compared to CD73 polypeptide). Optionally, the CD73 polypeptide is a soluble CD73 dimer. Optionally step (c) comprises selecting an antibody that neutralizes the enzymatic activity of said soluble CD73 polypeptide when antibodies are provided at a molar excess of antibody to CD73 dimers (e.g., an at least 2-fold, 5-fold, 10-fold, or 100-fold molar excess).

In one embodiment, the step of providing a plurality of antibodies comprises immunizing a non-human mammal with an immunogen comprising a CD73 polypeptide.

The disclosure also provides a method of potentiating the activity of lymphocytes (e.g., T cells) in a subject in need thereof, or for restoring the activity of lymphocytes (e.g., T cells), or a method of relieving the adenosine-mediated inhibition of lymphocytes (e.g., T cells), which method comprises administering to the subject an effective amount of any of the foregoing compositions. In one embodiment, the subject is a patient suffering from cancer. For example, the patient may be suffering from a solid tumor, e.g. colorectal cancer, renal cancer, ovarian cancer, lung cancer, breast cancer or malignant melanoma. Alternatively, the patient may be suffering from a hematopoietic cancer, e.g., acute myeloid leukaemia, chronic myeloid leukaemia, multiple myeloma, or non-Hodgkin's lymphoma.

The disclosure also provides a method for treatment of disease in an individual, the treatment comprising administering to the individual an anti-CD73 antibody that neutralizes the enzymatic activity of CD73 for at least one administration cycle in which the anti-CD73 antibody is administered at least once, optionally at least twice, in an amount effective to achieve, and/or to maintain between two successive administrations of the anti-CD73 antibody, a concentration in blood (serum) or an extravascular tissue (e.g. tumor environment) that corresponds to at least the $EC_{50}$ (e.g. an $EC_{50}$ between 0.01 and 0.5 μg/ml), optionally the $EC_{70}$ or optionally the $EC_{100}$, for neutralization of the enzymatic activity of CD73 (e.g. an $EC_{100}$ between 0.05 and 1 μg/ml, between 0.1 and 1 μg/ml). The antibody can for example be administered in an amount to achieve and/or maintained a concentration in circulation or in an extravascular tissue (e.g. tumor environment) of at least about 0.1 μg/ml, 0.5 μg/ml, 1 μg/ml or 2 μg/ml). For example, to achieve a concentration in an extravascular tissue of between 0.05 and 1 μg/ml, or between 0.1 and 1 μg/ml, the anti-CD73 antibody is administered in amounts effective to achieve a concentration in circulation of the anti-CD73 antibody of between 0.5 and 10 μg/ml, or between 1 and 10 μg/ml. Optionally, the anti-CD73 antibody is administered at least twice and in amounts effective to maintain the concentration of the anti-CD73 antibody at least the aforementioned concentration for at least 1 week, 2 weeks, 3 weeks, 4 weeks, between two successive administrations of the anti-CD73 antibody and/or throughout the administration cycle.

The disclosure also provides a method for treatment of disease in an individual, the treatment comprising administering to the individual an anti-CD73 antibody that neutralizes the enzymatic activity of CD73 for at least one administration cycle in which the anti-CD73 antibody is administered at least once, optionally at least twice, in an amount effective to achieve, and/or to maintain between two successive administrations of the anti-CD73 antibody, a blood or tissue concentration of anti-CD73 antibody of at least 1 μg/ml, optionally at least 10 μg/ml, optionally between 1 and 100 μg/ml. Optionally, the anti-CD73 antibody is administered at least twice and in amounts effective to maintain a continuous blood or tissue concentration of the anti-CD73 antibody of at least 1 μg/ml, optionally at least 10 μg/ml, optionally between 1 and 100 μg/ml, for at least 1 week, 2 weeks, 3 weeks, 4 weeks, between two successive administrations of the anti-Cd73 antibody and/or throughout the administration cycle.

These aspects are more fully described in, and additional aspects, features, and advantages will be apparent from, the description provided herein.

DETAILED DESCRIPTION OF THE INVENTION

Definitions

Figure 1:
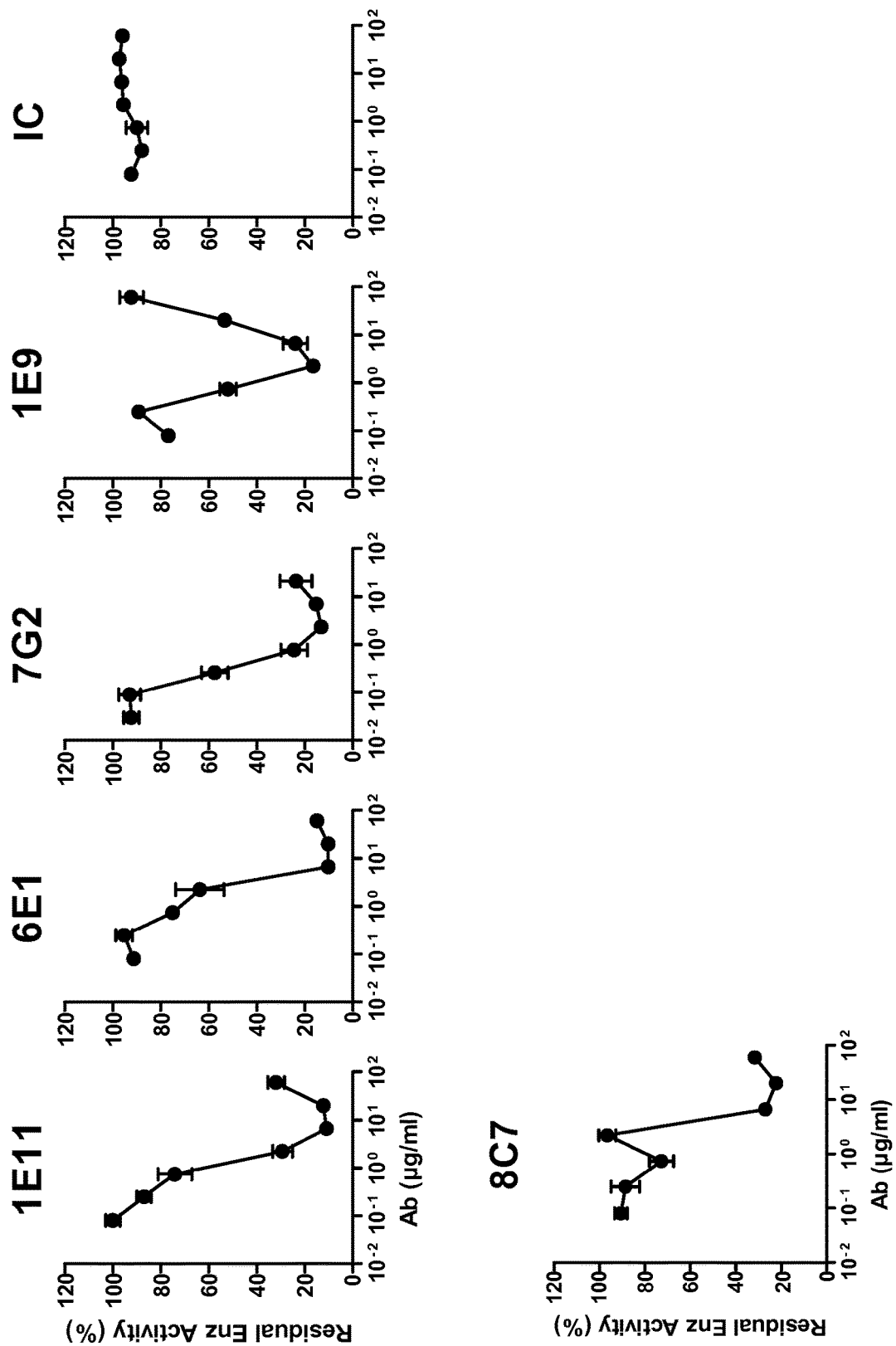
FIG. 1 shows ability of anti-CD73 antibodies to block enzymatic activity of CD73, assessed by measuring ability of test mAbs to affect CD73's ability to cleaves AMP into adenosine+inorganic phosphate that restores luciferase activity and light emission. Results are expressed as residual enzyme activity (%). Antibodies 11E1, 8C7, 6E1 and 3C12 (not shown) cause a strong decrease in enzyme activity, and continue to reduce residual enzyme activity even when provided at excess, an immune-complex-independent setting.

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

Human CD73, also known as ecto-5'-nudeotidase and as 5-prime-ribonucleotide phosphohydrolase, EC 3.1.3.5, encoded by the NT5E gene, exhibits 5-nucleotidase, notably AMP-, NAD-, and NMN-nucleosidase, activities. CD73 catalyzes the conversion at neutral pH of purine 5-prime mononucleotides to nucleosides, the preferred substrate being AMP. The enzyme consists of a dimer of 2 identical 70-kD subunits bound by a glycosyl phosphatidyl inositol linkage to the external face of the plasma membrane The amino acid sequence of Human CD73 preprotein (monomer), including a signal sequence at amino acids 1-26, is shown in Genbank under accession number NP_002517, the entire disclosure of which is incorporated herein by reference, and as follows:

```
                                               (SEQ ID NO: 1)
MCPRAARAPA TLLLALGAVL WPAAGAWELT ILHTNDVHSR

LEQTSEDSSK CVNASRCMGG VARLFTKVQQ IRRAEPNVLL

LDAGDQYQGT IWFTVYKGAE VAHFMNALRY DAMALGNHEF

DNGVEGLIEP LLKEAKFPIL SANIKAKGPL ASQISGLYLP

YKVLPVGDEV VGIVGYTSKE TPFLSNPGTN LVFEDEITAL

QPEVDKLKTL NVNKIIALGH SGFEMDKLIA QKVRGVDVVV

GGHSNTFLYT GNPPSKEVPA GKYPFIVTSD DGRKVPVVQA

YAFGKYLGYL KIEFDERGNV ISSHGNPILL NSSIPEDPSI

KADINKWRIK LDNYSTQELG KTIVYLDGSS QSCRFRECNM

GNLICDAMIN NNLRHTDEMF WNHVSMCILN GGGIRSPIDE

RNNGTITWEN LAAVLPFGGT FDLVQLKGST LKKAFEHSVH

RYGQSTGEFL QVGGIHVVYD LSRKPGDRVV KLDVLCTKCR

VPSYDPLKMD EVYKVILPNF LANGGDGFQM IKDELLRHDS

GDQDINVVST YISKMKVIYP AVEGRIKFST GSHCHGSFSL

IFLSLWAVIF VLYQ.
```

In the context herein, "neutralize the enzymatic activity of CD73", refers to a process in which the 5'-nucleotidase (5'-ectonucleotidase) activity of CD73 is inhibited. This comprises, notably the inhibition of CD73-mediated generation of adenosine, i.e. the inhibition of CD73-mediated catabolism of AMP to adenosine. This can be measured for example in a cell-free assay that measures the capacity of a test compound to inhibit the conversion of AMP to adenosine, either directly or indirectly. In one embodiment, an antibody preparation causes at least a 50% decrease in the conversion of AMP to adenosine, at least a 70% decrease in the conversion of AMP to adenosine, or at least a 80% decrease in the conversion of AMP to adenosine, referring, for example, to the assays described herein.

Whenever within this whole specification "treatment of cancer" or the like is mentioned with reference to anti-CD73 binding agent (e.g. antibody), there is meant: (a) method of treatment of cancer, said method comprising the step of administering (for at least one treatment) an anti-CD73 binding agent, (preferably in a pharmaceutically acceptable carrier material) to an individual, a mammal, especially a human, in need of such treatment, in a dose that allows for the treatment of cancer, (a therapeutically effective amount), preferably in a dose (amount) as specified herein; (b) the use of an anti-CD73 binding agent for the treatment of cancer, or an anti-CD73 binding agent, for use in said treatment (especially in a human); (c) the use of an anti-CD73 binding agent for the manufacture of a pharmaceutical preparation for the treatment of cancer, a method of using an anti-CD73 binding agent for the manufacture of a pharmaceutical preparation for the treatment of cancer, comprising admixing an anti-CD73 binding agent with a pharmaceutically acceptable carrier, or a pharmaceutical preparation comprising an effective dose of an anti-CD73 binding agent that is appropriate for the treatment of cancer; or (d) any combination of a), b), and c), in accordance with the subject matter allowable for patenting in a country where this application is filed.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. CD73, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody, it means that the antibody competes with the monoclonal antibody in a binding assay using either recombinant CD73 molecules or surface expressed CD73 molecules. For example, if a test antibody reduces the binding of a reference antibody to a CD73 polypeptide or CD73-expressing cell in a binding assay, the antibody is said to "compete" respectively with the reference antibody.

The term "affinity", as used herein, means the strength of the binding of an antibody to an epitope. The affinity of an antibody is given by the dissociation constant Kd, defined as [Ab]×[Ag]/[Ab–Ag], where [Ab–Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "deplete" or "depleting", with respect to CD73-expressing cells, means a process, method, or compound that results in killing, elimination, lysis or induction of such killing, elimination or lysis, so as to negatively affect the number of such CD73-expressing cells present in a sample or in a subject.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917), or a similar system for determining essential amino acids responsible for antigen binding. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Ws.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Antibodies

The anti-CD73 agent that can be used for the treatment of cancers binds an extra-cellular portion of human CD73 polypeptide and neutralizes the enzymatic activity of CD73 expressed on the surface of a cell, e.g. a tumor cell. In one embodiment the agent inhibits the 5'-ectonucleotidase activity of CD73. In one embodiment the antibody inhibits CD73-mediated generation of adenosine. In one embodiment the antibody inhibits CD73-mediated catabolism of AMP to adenosine. In one embodiment the antibody inhibits adenosine-mediated inhibition of lymphocyte activity (e.g. T cells). In one embodiment the antibody binds and/or inhibits the enzymatic active site on CD73. In one aspect, the agent is an antibody selected from a full-length antibody, an antibody fragment, and a synthetic or semisynthetic antibody-derived molecule.

In one aspect, the agent is an antibody selected from a fully human antibody, a humanized antibody, and a chimeric antibody.

In one aspect, the agent is a fragment of an antibody comprising a constant domain selected from IgG1, IgG2, IgG3 and IgG4.

In one aspect, the agent is an antibody fragment selected from a Fab fragment, a Fab' fragment, a Fab'-SH fragment, a F(ab)2 fragment, a F(ab')2 fragment, an Fv fragment, a started hereHeavy chain Ig (a llama or camel Ig), a $V_{HH}$ fragment, a single domain FV, and a single-chain antibody fragment.

In one aspect, the agent is a synthetic or semisynthetic antibody-derived molecule selected from a scFV, a dsFV, a minibody, a diabody, a triabody, a kappa body, an IgNAR; and a multispecific antibody.

The present disclosure thus concerns antibodies or other antigen-binding agents binding to CD73.

In one aspect, the antibody is in at least partially purified form.

In one aspect, the antibody is in essentially isolated form.

The antibodies may be produced by a variety of techniques known in the art.

Typically, they are produced by immunization of a non-human animal, preferably a mouse, with an immunogen comprising a CD73 polypeptide, preferably a human CD73 polypeptide. The CD73 polypeptide may comprise the full length sequence of a human CD73 polypeptide, or a fragment or derivative thereof, typically an immunogenic fragment, i.e., a portion of the polypeptide comprising an epitope exposed on the surface of cells expressing a CD73 polypeptide. Such fragments typically contain at least about 7 consecutive amino acids of the mature polypeptide sequence, even more preferably at least about 10 consecutive amino acids thereof. Fragments typically are essentially derived from the extra-cellular domain of the receptor. In one embodiment, the immunogen comprises a wild-type human CD73 polypeptide in a lipid membrane, typically at the surface of a cell. In a specific embodiment, the immunogen comprises intact cells, particularly intact human cells, optionally treated or lysed. In another embodiment, the polypeptide is a recombinant CD73 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with CD73 polypeptides.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A, X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to CD73 polypeptide gene products. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to CD73 polypeptides, e.g., CD73-expressing cells.

Hybridomas that are confirmed to produce a monoclonal antibody can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to CD73, particularly substantially or essentially the same epitope as monoclonal antibody 11E1, 8C7 or 6E1, can be readily determined using any one of a variety of immunological screening assays in which antibody competition can be assessed. Many such assays are routinely practiced and are well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (11E1, 8C7 or 6E1, for example) and test antibodies are admixed (or pre-adsorbed) and applied to a sample containing CD73 polypeptides. Protocols based upon western blotting and the use of BIA-CORE analysis are suitable for use in such competition studies.

In certain embodiments, one pre-mixes the control antibodies (11E1, 8C7, 3C12 or 6E1, for example) with varying amounts of the test antibodies (e.g., about 1:10 or about 1:100) for a period of time prior to applying to the CD73 antigen sample. In other embodiments, the control and varying amounts of test antibodies can simply be admixed during exposure to the CD73 antigen sample. As long as one can distinguish bound from free antibodies (e.g., by using separation or washing techniques to eliminate unbound antibodies) and 11E1, 8C7, 3C12 or 6E1 from the test antibodies (e.g., by using species-specific or isotype-specific secondary antibodies or by specifically labeling 11E1, 8C7, 3C12 or 6E1 with a detectable label) one can determine if the test antibodies reduce the binding of 11E1, 8C7, 3C12 or 6E1 to the antigens, indicating that the test antibody recognizes substantially the same epitope as 11E1, 8C7, 3C12 or 6E1. The binding of the (labelled) control antibodies in the absence of a completely irrelevant antibody can serve as the control high value. The control low value can be obtained by incubating the labelled (11E1, 8C7, 3C12 or 6E1) antibodies with unlabelled antibodies of exactly the same type (11E1, 8C7, 3C12 or 6E1), where competition would occur and reduce binding of the labelled antibodies. In a test assay, a significant reduction in labelled antibody reactivity in the presence of a test antibody is indicative of a test antibody that recognizes substantially the same epitope, i.e., one that "cross-reacts" or competes with the labelled (11E1, 8C7, 3C12 or 6E1) antibody. Any test antibody that reduces the binding of 11E1, 8C7, 3C12 or 6E1 to CD73 antigens by at least about 50%, such as at least about 60%, or more preferably at least about 80% or 90% (e.g., about 65-100%), at any ratio of 11E1, 8C7, 3C12 or 6E1:test antibody between about 1:10 and about 1:100 is considered to be an antibody that binds to substantially the same epitope or determinant as 11E1, 8C7, 3C12 or 6E1. Preferably, such test antibody will reduce the binding of 11E1, 8C7, 3C12 or 6E1 to the CD73 antigen by at least about 90% (e.g., about 95%).

Competition can also be assessed by, for example, a flow cytometry test. In such a test, cells bearing a given CD73 polypeptide can be incubated first with 11E1, 8C7, 3C12 or 6E1, for example, and then with the test antibody labelled with a fluorochrome or biotin. The antibody is said to compete with 11E1, 8C7, 3C12 or 6E1 if the binding obtained upon preincubation with a saturating amount of 11E1, 8C7, 3C12 or 6E1 is about 80%, preferably about 50%, about 40% or less (e.g., about 30%, 20% or 10%) of the binding (as measured by mean of fluorescence) obtained by the antibody without preincubation with 11E1, 8C7, 3C12 or 6E1. Alternatively, an antibody is said to compete with 11E1, 8C7, 3C12 or 6E1 if the binding obtained with a labelled 11E1, 8C7, 3C12 or 6E1 antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a CD73 antigen is immobilized may also be employed. The surface in the simple competition assay is preferably a BIACORE chip (or other media suitable for surface plasmon resonance analysis). The control antibody (e.g., 11E1, 8C7, 3C12 or 6E1) is then brought into contact with the surface at a CD73-saturating concentration and the CD73 and surface binding of the control antibody is measured. This binding of the control antibody is compared with the binding of the control antibody to the CD73-containing surface in the absence of test antibody. In a test assay, a significant reduction in binding of the CD73-containing surface by the control antibody in the presence of a test antibody indicates that the test antibody recognizes substantially the same epitope as the control antibody such that the test antibody "cross-reacts" with the control antibody. Any test antibody that reduces the binding of control (such as 11E1, 8C7, 3C12 or 6E1) antibody to a CD73 antigen by at least about 30% or more, preferably about 40%, can be considered to be an antibody that binds to substantially the same epitope or determinant as a control (e.g., 11E1, 8C7, 3C12 or 6E1). Preferably, such a test antibody will reduce the binding of the control antibody (e.g., 11E1, 8C7, 3C12 or 6E1) to the CD73 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the CD73 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

The antibodies will bind to CD73-expressing cells from an individual or individuals with a disease characterized by expression of CD73-positive cells, i.e. an individual that is a candidate for treatment with one of the herein-described methods using an anti-CD73 antibody. Accordingly, once an antibody that specifically recognizes CD73 on cells is obtained, it can optionally be tested for its ability to bind to CD73-positive cells (e.g. cancer cells). In particular, prior to treating a patient with one of the present antibodies, one may optionally test the ability of the antibody to bind malignant cells taken from the patient, e.g. in a blood sample or tumor biopsy, to maximize the likelihood that the therapy will be beneficial in the patient.

In one embodiment, the antibodies are validated in an immunoassay to test their ability to bind to CD73-expressing cells, e.g. malignant cells. For example, a blood sample or tumor biopsy is performed and tumor cells are collected. The ability of a given antibody to bind to the cells is then assessed using standard methods well known to those in the art. Antibodies may bind for example to a substantial proportion (e.g., 20%, 30%, 40%, 50%, 60%, 70%, 80% or more) of cells known to express CD73, e.g. tumor cells, from a significant percentage of individuals or patients (e.g., 10%, 20%, 30%, 40%, 50% or more). Antibodies can be used for diagnostic purposes to determine the presence or level of malignant cells in a patient, for example as a biomarker to assess whether a patient is suitable for treatment with an anti-CD73 agent, or for use in the herein-described therapeutic methods. To assess the binding of the antibodies to the cells, the antibodies can either be directly or indirectly labelled. When indirectly labelled, a secondary, labelled antibody is typically added.

Determination of whether an antibody binds within an epitope region can be carried out in ways known to the person skilled in the art. As one example of such mapping/characterization methods, an epitope region for an anti-CD73 antibody may be determined by epitope "foot-printing" using chemical modification of the exposed amines/carboxyls in the CD73 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g. by using trypsin in a ratio of about 1:50 to CD73 or o/n digestion at and pH 7-8, followed by mass spectrometry (MS) analysis for peptide identification. The peptides protected from trypsin cleavage by the anti-CD73 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the CD73 polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "foot-printing". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chroma-togr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody can be identified in one or more of the exemplary competition assays described herein.

Upon immunization and production of antibodies in a vertebrate or cell, particular selection steps may be performed to isolate antibodies as claimed. In this regard, in a specific embodiment, the disclosure also relates to methods of producing such antibodies, comprising: (a) immunizing a non-human mammal with an immunogen comprising a CD73 polypeptide; and (b) preparing antibodies from said immunized animal; and (c) selecting antibodies from step (b) that are capable of binding CD73.

Typically, an anti-CD73 antibody provided herein has an affinity for a CD73 polypeptide (e.g. as a CD73 homodimer) in the range of about $10^4$ to about $10^{11}$ $M^{-1}$ (e.g., about $10^8$ to about $10^{10}$ $M^{-1}$). For example, in a particular aspect the disclosure provides Anti-CD73 antibody that have an average disassociation constant ($K_D$) of less than $1 \times 10^{-9}$ M with respect to CD73, as determined by, e.g., surface plasmon resonance (SPR) screening (such as by analysis with a BIAcore™ SPR analytical device). In a more particular exemplary aspect, the disclosure provides anti-CD73 antibodies that have a KD of about $1 \times 10^{-8}$ M to about $1 \times 10^{-10}$ M, or about $1 \times 10^{-9}$ M to about $1 \times 10^{-11}$ M, for CD73.

Antibodies can be characterized for example by a mean KD of no more than about (i.e. better affinity than) 100, 60, 10, 5, or 1 nanomolar, preferably sub-nanomolar or optionally no more than about 500, 200, 100 or 10 picomolar. KD can be determined for example for example by immobilizing recombinantly produced human CD73 proteins on a chip surface, followed by application of the antibody to be tested in solution. In one embodiment, the method further comprises a step (d), selecting antibodies from (b) that are capable of competing for binding to CD73 with antibody 11E1, 8C7, 3C12 or 6E1.

In one aspect of any of the embodiments, the antibodies prepared according to the present methods are monoclonal antibodies. In another aspect, the non-human animal used to produce antibodies according to the methods herein is a mammal, such as a rodent, bovine, porcine, fowl, horse, rabbit, goat, or sheep.

DNA encoding an antibody that binds an epitope present on CD73 polypeptides is isolated from a hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding the monoclonal antibodies of the disclosure, e.g., antibody 11E1, 8C7, 3C12 or 6E1, can be readily isolated and sequenced using conventional procedures (e.g., by using oligonucleotide probes that are capable of binding specifically to genes encoding the heavy and light chains of murine antibodies). In one aspect, provided is a nucleic acid encoding a heavy chain or a light chain of an anti-CD73 antibody of any embodiment herein. Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. In one embodiment, provided is an isolated nucleic acid sequence encoding a light chain and/or a heavy chain of an antibody (e.g. 11E1, 8C7, 3C12 or 6E1), as well as a recombinant host cell comprising (e.g. in its genome) such nucleic acid. Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

Optionally, antibodies of the disclosure can be specified to be antibodies other than any one or more of antibodies 7G2 (Life Technologies Corp.), antibody 4G4 (Abcam, product ref. ab81720), antibody AD2 (Biolegend Corp, product ref. 344004), antibody 1E9 (Santa Cruz Biotechnology Corp., product sc-32299), 067-213 antibody described in US 2014/0235833, the anti-CD73 antibody referenced in Sachsenmeier et al. ((2012) J. Biomed. Screening 17:993-998 and/or in Rust et al. (2013) Mol. Cancer 12:11, or antibody MED19447 (Medimmune Corp, Gaithersburg Md.) referenced in Huang et al. (2015) AACR Annual meeting; Abstract 1538, or derivatives of the foregoing, e.g. that comprise the antigen binding region or heavy and/or light chain CDRs, in whole or in part. In other embodiments, the above-mentioned antibodies may, depending on the nature of the antibody, be modified so as to have the characteristics of the antibodies of the present disclosure.

Once antibodies are identified that are capable of binding CD73 and/or having other desired properties, they will also typically be assessed, using standard methods including those described herein, for their ability to bind to other polypeptides, including unrelated polypeptides. Ideally, the antibodies only bind with substantial affinity to CD73, and do not bind at a significant level to unrelated polypeptides, or other polypeptides of the 5'-nucleotidase family. However, it will be appreciated that, as long as the affinity for CD73 is substantially greater (e.g., 10×, 100×, 500×, 1000×, 10,000×, or more) than it is for other, unrelated polypeptides), then the antibodies are suitable for use in the present methods.

In one embodiment, the anti-CD73 antibodies can be prepared such that they do not have substantial specific binding to human Fcγ receptors, e.g., any one or more of CD16A, CD16B, CD32A, CD32B and/or CD64). Such antibodies may comprise constant regions of various heavy chains that are known not to bind Fcγ receptors. One such example is a wild type human IgG4 constant region (IgG4 have minimal Fcγ receptor binding). A human IgG4 constant region can further comprise a stabilizing S228P (S241P) substitution) to retain bivalent binding ability in vivo by preventing Fab arm exchange. Alternatively, antibody fragments that do not comprise (or comprise portions of) constant regions, such as F(ab')2 fragments, can be used to avoid Fc receptor binding. Fc receptor binding can be assessed according to methods known in the art, including for example testing binding of an antibody to Fc receptor protein in a BIACORE assay. Also, generally any antibody IgG isotype can be used in which the Fc portion is modified (e.g., by introducing 1, 2, 3, 4, 5 or more amino acid substitutions) to minimize or eliminate binding to Fc receptors (see, e.g., WO 03/101485, the disclosure of which is herein incorporated by reference). Assays such as cell based assays, to assess Fc receptor binding are well known in the art, and are described in, e.g., WO 03/101485.

In one embodiment, the antibody can comprise one or more specific mutations in the Fc region that result in "Fc silent" antibodies that have minimal interaction with effector cells. Silenced effector functions can be obtained by mutation in the Fc region of the antibodies and have been described in the art: N297A mutation, the LALA mutations, (Strohl, W., 2009, Curr. Opin. Biotechnol. vol. 20(6):685-691); and D265A (Baudino et al., 2008, J. Immunol. 181: 6664-69) see also Heusser et al., WO2012/065950, the disclosures of which are incorporated herein by reference. In one embodiment, an antibody comprises one, two, three or more amino acid substitutions in the hinge region. In one embodiment, the antibody is an IgG1 or IgG2 and comprises one, two or three substitutions at residues 233-236, optionally 233-238 (EU numbering). In one embodiment, the antibody is an IgG4 and comprises one, two or three substitutions at residues 327, 330 and/or 331 (EU numbering). Examples of silent Fc IgG1 antibodies are the LALA mutant comprising L234A and L235A mutation in the IgG1 Fc amino acid sequence. Another example of an Fc silent mutation is a mutation at residue D265, or at D265 and P329 for example as used in an IgG1 antibody as the DAPA (D265A, P329A) mutation (U.S. Pat. No. 6,737,056). Another silent IgG1 antibody comprises a mutation at residue N297 (e.g. N297A, N297S mutation), which results in aglycosylated/non-glycosylated antibodies. Other silent mutations include: substitutions at residues L234 and G237 (L234A/G237A); substitutions at residues S228, L235 and R409 (S228P/L235E/R409K,T,M,L); substitutions at residues H268, V309, A330 and A331 (H268Q/V309L/A330S/A331S); substitutions at residues C220, C226, C229 and P238 (C220S/C226S/C229S/P238S); substitutions at residues C226, C229, E233, L234 and L235 (C226S/C229S/E233P/L234V/L235A; substitutions at residues K322, L235 and L235 (K322A/L234A/L235A); substitutions at residues L234, L235 and P331 (L234F/L235E/P331S); substitutions at residues 234, 235 and 297; substitutions at residues E318, K320 and K322 (L235E/E318A/K320A/K322A); substitutions at residues (V234A, G237A, P238S); substitutions at residues 243 and 264; substitutions at residues 297 and 299; substitutions such that residues 233, 234, 235, 237, and 238 defined by the EU numbering system, comprise a sequence selected from PAAAP, PAAAS and SAAAS (see WO2011/066501).

Fc silent antibodies result in no or low ADCC activity, meaning that an Fc silent antibody exhibits an ADCC activity that is below 50% specific cell lysis. Preferably an antibody substantially lacks ADCC activity, e.g., the Fc silent antibody exhibits an ADCC activity (specific cell lysis) that is below 5% or below 1%. Fc silent antibodies can also result in lack of FcγR-mediated cross-linking of CD73 at the surface of a CD73-expression.

In one embodiment, the antibody has a substitution in a heavy chain constant region at any one, two, three, four, five or more of residues selected from the group consisting of: 220, 226, 229, 233, 234, 235, 236, 237, 238, 243, 264, 268, 297, 298, 299, 309, 310, 318, 320, 322, 327, 330, 331 and 409 (numbering of residues in the heavy chain constant region is according to EU numbering according to Kabat). In one embodiment, the antibody comprises a substitution at residues 234, 235 and 322. In one embodiment, the antibody has a substitution at residues 234, 235 and 331.

In one embodiment, the Fc silent antibody comprises an Fc domain comprising an amino acid substitution at residues 234, 235 and 331, for example the "TM" mutation having substitutions L234F, L235E and P331S. In one embodiment, the antibody comprises an Fc domain comprising an amino acid substitution at residues 234, 235 and 322, or at residues 234, 235 and 331, described in US Patent publication no. US2015/0125444, wherein residue 234 is F (phenylalanine); residue 235 is Alanine (A), Asparagine (N), Phenylalanine (F), Glutamine (Q), or Valine (V); residue 322 is Alanine (A), Aspartic acid (D), Glutamic acid (E), Histidine (H), Asparagine (N), or Glutamine (Q); and residue 331 is Alanine (A) or Glycine (G). Amino acid residues are indicated according to EU numbering according to Kabat.

In one embodiment, the antibody comprises an Fc domain comprising an amino acid substitution that increases binding to human FcRn polypeptides in order to increase the in vivo half-life of the antibody. Exemplary mutations are described in Strohl, W., 2009, Curr. Opin. Biotechnol. vol. 20(6):685-691, the disclosure of which is incorporated herein by reference. Examples of substitutions used in antibodies of human IgG1 isotype are substitutions at residues M252, S254 and T256; substitutions at residues T250 and M428; substitutions at residue N434; substitutions at residues H433 and N434; substitutions at residues T307, E380 and N434; substitutions at residues T307, E380, and N434; substitutions at residues M252, S254, T256, H433, N434 and 436; substitutions at residue I253; substitutions at residues P257, N434, D376 and N434.

In one embodiment, the antibody comprises an Fc domain comprising an amino acid substitution that confers decreased sensitivity to cleavage by proteases. Matrix metalloproteinases (MMPs) represent the most prominent family of proteinases associated with tumorigenesis. While cancer cells can express MMPs, the bulk of the extracellular MMP is provided by different types of stromal cells that infiltrate the tumor and each produce a specific set of proteinases and proteinase inhibitors, which are released into the extracellular space and specifically alter the milieu around the tumor. The MMPs present in the tumor microenvironment can cleave antibodies within the hinge region and may thus lead to the inactivation of therapeutic antibodies that are designed to function within the tumor site. In one embodiment, the Fc domain comprising an amino acid substitution has decreased sensitivity to cleavage by any one, two, three or more (or all of) of the proteases selected from the group consisting of: GluV8, IdeS, gelatinase A (MMP2), gelatinase B (MMP-9), matrix metalloproteinase-7 (MMP-7), stromelysin (MMP-3), and macrophage elastase (MMP-12). In one embodiment, the antibody decreased sensitivity to cleavage comprises an Fc domain comprising an amino acid substitution at residues E233-L234 and/or L235. In one embodiment, the antibody comprises an Fc domain comprising an amino acid substitution at residues E233, L234, L235 and G236. In one embodiment, the antibody comprises an Fc domain comprising an amino acid substitution at one or more residues 233-238, e.g., such that E233-L234-L235-G236 sequence is replaced by P233-V234-A235 (G236 is deleted). See, e.g., WO99/58572 and WO2012087746, the disclosures of which are incorporated herein by reference.

An antigen-binding compound can at any desired stage be assessed for its ability to inhibit the enzymatic activity of CD73, notably to block the 5'-nucleotidase activity of CD73 and to reduce the production of adenosine by a CD73-expressing cell, and in turn restore the activity of and/or relieve the adenosine-mediated inhibition of lymphocytes.

The ability of an antibody to inhibit the enzymatic activity of CD73 can be tested in a cell-free assay using recombinant soluble human CD73 (as dimers) and AMP, where conversion of AMP to adenosine (and/or inhibition thereof) is detected directly (e.g. by measurement of substrates and products, i.e. AMP, adenosine and/or phosphate), or indirectly. In one example, AMP and/or adenosine are detected via HPLC before and after incubation of the test compound with recombinant CD73. Recombinant CD73 is available, e.g., from R&D Systems (Minneapolis, Minn.).

The inhibitory activity (i.e. cytotoxicity enhancing potential) of an antibody can also be assessed in any of a number of other ways. For example, in an indirect assay, a luciferase-based reagent is used (e.g. CellTiter-Glo® system available from Promega), to detect the disappearance of AMP. The luciferase reaction in the assay is inhibited by AMP. Adding the CD73 enzyme to the reaction degrades the AMP, and relieves the inhibition, producing a detectable signal (see Example 2 herein).

The assays using soluble CD73 will be include testing at conditions where the antibodies are provided at a substantial molar excess (e.g. 10-fold, 20-fold, 50-fold, 100-fold, etc.) to the CD73 polypeptide dimers. When provided in molar excess to the enzyme, the anti-CD73 antibodies will no longer be capable of forming multimeric complexes of antibodies and CD73 dimers; antibodies that retain inhibition of the enzymatic activity of CD73 can then be selected.

The ability of an antibody to inhibit the 5'-ectonucletidase enzymatic activity of CD73 can alternatively or in addition also be tested in a cellular assay (using cells that express CD73). Advantageously, antibodies can be tested or screened first in the cell-free assay to identify antibodies that block the activity of the enzyme to reduce likelihood of selecting antibodies that inhibit CD73 by causing internalization of CD73, and then tested as purified antibody in cellular assays. Cellular assays can be carried out as shown in the Examples herein. For example, a CD73-expressing cell line (e.g. MDA-MB-231 cell line) are plated in flat-bottom 96 well plates in presence of anti-CD73 antibodies and incubated. AMP is added to the cells and incubated at 4° C. (to avoid CD73 down-modulation). Plates are then centrifuged and supernatant is transferred to flat bottom 96 well culture plate. Free phosphate produced by the hydrolysis of AMP into adenosine is then quantified. A decrease in hydrolysis of AMP into adenosine in the presence of antibody indicate the antibody inhibits cellular CD73.

In one embodiment, an antibody preparation causes at least a 50% decrease in the enzymatic activity of a CD73 polypeptide, preferably at least a 60%, 70% or 80% decrease in the enzymatic activity of a CD73 polypeptide (e.g. a soluble homodimeric CD73 polypeptide; CD73 expressed by cells).

The activity of an antibody can also be measured in an indirect assay for its ability to modulate the activity of lymphocytes, for example to relieve the adenosine-mediated inhibition of lymphocyte activity, or to cause the activation of lymphocyte activity. This can be addressed, for example, using a cytokine-release assay. In another example, an antibody can be evaluated in an indirect assay for its ability to modulate the proliferation of lymphocytes.

The antibody can be tested for its ability to internalize or to induce down-modulation of CD73, e.g. whether by internalization or induction of CD73 shedding from the cell surface. Whether an anti-CD73 antibody internalizes upon binding CD73 on a mammalian cell, or whether a CD73 polypeptide undergoes intracellular internalization (e.g. upon being bound by an antibody) can be determined by various assays including those described in the experimental examples herein (e.g., Example 7). In other examples, to test internalization in vivo, the test antibody is labeled and introduced into an animal known to have CD73 expressed on the surface of certain cells. The antibody can be radio-labeled or labeled with fluorescent or gold particles, for instance. Animals suitable for this assay include a mammal such as a nude mouse that contains a human CD73-expressing tumor transplant or xenograft, or a mouse into which cells transfected with human CD73 have been introduced, or a transgenic mouse expressing the human CD73 transgene. Appropriate controls include animals that did not receive the test antibody or that received an unrelated antibody, and animals that received an antibody to another antigen on the cells of interest, which antibody is known to be internalized upon binding to the antigen. The antibody can be administered to the animal, e.g., by intravenous injection. At suitable time intervals, tissue sections of the animal can be prepared using known methods or as described in the experimental examples below, and analyzed by light microscopy or electron microscopy, for internalization as well as the location of the internalized antibody in the cell. For internalization in vitro, the cells can be incubated in tissue culture dishes in the presence or absence of the relevant antibodies added to the culture media and processed for microscopic analysis at desired time points. The presence of an internalized, labeled antibody in the cells can be directly visualized by microscopy or by autoradiography if radiolabeled antibody is used. Optionally, in microscopy, co-localization with a known polypeptide or other cellular component can be assessed; for example co-localization with endosomal/lysosomal marker LAMP-1 (CD107a) can provide information about the subcellular localization of the internalized antibody. Alternatively, in a quantitative biochemical assay, a population of cells comprising CD73-expressing cells are contacted in vitro or in vivo with a radiolabeled test antibody and the cells (if contacted in vivo, cells are then isolated after a suitable amount of time) are treated with a protease or subjected to an acid wash to remove un-internalized antibody on the cell surface. The cells are ground up and the amount of protease resistant, radioactive counts per minute (cpm) associated with each batch of cells is measured by passing the homogenate through a scintillation counter. Based on the known specific activity of the radiolabeled antibody, the number of antibody molecules internalized per cell can be deduced from the scintillation counts of the ground-up cells. Cells are "contacted" with antibody in vitro preferably in solution form such as by adding the cells to the cell culture media in the culture dish or flask and mixing the antibody well with the media to ensure uniform exposure of the cells to the antibody.

Antibody Epitopes

In one aspect, the antibodies bind a common antigenic determinant present on both soluble CD73 and CD73 expressed at the cell surface.

In one aspect, the antibodies bind substantially the same epitope as antibody 11E1, 8C7, 3C12 or 6E1. In one embodiment, the antibodies bind to an epitope of CD73 that at least partially overlaps with, or includes at least one residue in, the epitope bound by antibody 11E1, 8C7, 3C12 or 6E1. The residues bound by the antibody can be specified as being present on the surface of the of the CD73 polypeptide, e.g. in a CD73 polypeptide expressed on the surface of a cell. The amino acid residues on CD73 bound by the antibody can for example be selected from the group consisting of the residues listed in Table 1.

Binding of anti-CD73 antibody to cells transfected with CD73 mutants can be measured and compared to the ability of anti-CD73 antibody to bind wild-type CD73 polypeptide (e.g., SEQ ID NOS: 1 or 2). A reduction in binding between an anti-CD73 antibody and a mutant CD73 polypeptide (e.g., a mutant CD73 of Table 1) means that there is a reduction in binding affinity (e.g., as measured by known methods such FACS testing of cells expressing a particular mutant, or by Biacore testing of binding to mutant polypeptides) and/or a reduction in the total binding capacity of the anti-CD73 antibody (e.g., as evidenced by a decrease in Bmax in a plot of anti-CD73 antibody concentration versus polypeptide concentration). A significant reduction in binding indicates that the mutated residue is directly involved in binding to the anti-CD73 antibody or is in close proximity to the binding protein when the anti-CD73 antibody is bound to CD73.

In some embodiments, a significant reduction in binding means that the binding affinity and/or capacity between an anti-CD73 antibody and a mutant CD73 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type CD73 polypeptide. In certain embodiments, binding is reduced below detectable limits. In some embodiments, a significant reduction in binding is evidenced when binding of an anti-CD73 antibody to a mutant CD73 polypeptide is less than 50% (e.g., less than 45%, 40%, 35%, 30%, 25%, 20%, 15% or 10%) of the binding observed between the anti-CD73 antibody and a wild-type CD73 polypeptide.

In some embodiments, anti-CD73 antibodies are provided that exhibit significantly lower binding for a mutant CD73 polypeptide in which a residue in a segment comprising an amino acid residue bound by antibody 11E1, 8C7, 3C12 or 6E1 is substituted with a different amino acid. In one embodiment, the mutant is a mutant selected from mutants 1-15 of Table 1, e.g., mutant 3, or to a mutant comprising one or more of the amino acid substitutions of such mutant 3, compared to binding to a wild-type CD73 polypeptide (e.g. the polypeptide of SEQ ID NO: 1).

Optionally an antibody that loses binding to one or more mutants of mutants 1-15 does not exhibit significantly lower binding for one or more other mutants CD73 polypeptides of Table 1, e.g., one or more (or all of) mutants 2, 5, 6 or 7.

In one aspect, the anti-CD73 antibodies have reduced binding to a CD73 polypeptide having a mutation at a residue selected from the group consisting of: A99, E129, K133, E134, and A135 (with reference to SEQ ID NO: 1); optionally, the mutant CD73 polypeptide has the mutations: A99S, E129A, K133A, E134N, and A135S.

Optionally, in one aspect, the anti-CD73 antibodies do not have reduced binding to a CD73 polypeptide having a mutation at a residue selected from the group consisting of: Q70, R73, A74, A107 and R109 (with reference to SEQ ID NO: 1); optionally, the mutant CD73 polypeptide has the mutations: A99S, Q70S, R73A, A74E, A107I and R109G.

In one aspect, the anti-CD73 antibodies bind an epitope on CD73 comprising one, two, three, four or five of the residues selected from the group consisting of A99, E129, K133, E134, and A135 (with reference to SEQ ID NO: 1).

Optionally, in one aspect, the anti-CD73 antibodies do not bind an epitope on CD73 comprising one, two, three, four or five of the residues selected from the group consisting of Q70, R73, A74, A107 and R109 (with reference to SEQ ID NO: 1).

Antibody CDR Sequences
Antibody 11E1

The amino acid sequence of the heavy chain variable region of antibody 11E1 is listed as SEQ ID NO: 3, the amino acid sequence of the light chain variable region is listed as SEQ ID NO: 4. In a specific embodiment, the disclosure provides an antibody that binds essentially the same epitope or determinant as monoclonal antibodies 11E1; optionally the antibody comprises the hypervariable region of antibody 11E1. In any of the embodiments herein, antibody 11E1 can be characterized by the amino acid sequences and/or nucleic acid sequences encoding it. In one embodiment, the monoclonal antibody comprises the Fab or F(ab')$_2$ portion of 11E1. Also provided is a monoclonal antibody that comprises the heavy chain variable region of 11E1. According to one embodiment, the monoclonal antibody comprises the three CDRs of the heavy chain variable region of 11E1 Also provided is a monoclonal antibody that further comprises the variable light chain variable region of 11E1 or one, two or three of the CDRs of the light chain variable region of 11E1. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 11E1 are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, the disclosure provides an antibody, wherein the antibody comprises: a HCDR1 region of 11E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 11E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 11E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 11E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 11E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 11E1 comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 6E1

The amino acid sequence of the heavy chain variable region of antibody 6E1 is listed as SEQ ID NO: 21, the amino acid sequence of the light chain variable region is listed as SEQ ID NO: 22. In a specific embodiment, the disclosure provides an antibody that binds essentially the same epitope or determinant as monoclonal antibodies 6E1; optionally the antibody comprises the hypervariable region of antibody 6E1. In any of the embodiments herein, antibody 6E1 can be characterized by the amino acid sequences and/or nucleic acid sequences encoding it. In one embodiment, the monoclonal antibody comprises the Fab or F(ab')$_2$ portion of 6E1. Also provided is a monoclonal antibody that comprises the heavy chain variable region of 6E1. According to one embodiment, the monoclonal antibody comprises the three CDRs of the heavy chain variable region of 6E1 Also provided is a monoclonal antibody that further comprises the variable light chain variable region of 6E1 or one, two or three of the CDRs of the light chain variable region of 6E1. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 6E1 are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, the disclosure provides an antibody, wherein the antibody comprises: a HCDR1 region of 6E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 6E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 6E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 6E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 6E1 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 6E1 comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 3C12

The amino acid sequence of the heavy chain variable region of antibody 3C12 is listed as SEQ ID NO: 36, the amino acid sequence of the light chain variable region is listed as SEQ ID NO: 37. In a specific embodiment, the disclosure provides an antibody that binds essentially the same epitope or determinant as monoclonal antibodies 3C12; optionally the antibody comprises the hypervariable region of antibody 3C12. In any of the embodiments herein, antibody 3C12 can be characterized by the amino acid sequences and/or nucleic acid sequences encoding it. In one embodiment, the monoclonal antibody comprises the Fab or F(ab')$_2$ portion of 3C12. Also provided is a monoclonal antibody that comprises the heavy chain variable region of 3C12. According to one embodiment, the monoclonal antibody comprises the three CDRs of the heavy chain variable region of 3C12. Also provided is a monoclonal antibody that further comprises the variable light chain variable region of 3C12 or one, two or three of the CDRs of the light chain variable region of 3C12. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 3C12 are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, the disclosure provides an antibody, wherein the antibody comprises: a HCDR1 region of 3C12 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 3C12 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 3C12 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 3C12 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 3C12 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 3C12 comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

Antibody 8C7

The amino acid sequence of the heavy chain variable region of antibody 8C7 is listed as SEQ ID NO: 28, the amino acid sequence of the light chain variable region is listed as SEQ ID NO: 29. In a specific embodiment, the disclosure provides an antibody that binds essentially the same epitope or determinant as monoclonal antibodies 8C7; optionally the antibody comprises the hypervariable region of antibody 8C7. In any of the embodiments herein, antibody 8C7 can be characterized by the amino acid sequences and/or nucleic acid sequences encoding it. In one embodiment, the monoclonal antibody comprises the Fab or F(ab')$_2$ portion of 8C7. Also provided is a monoclonal antibody that comprises the heavy chain variable region of 8C7. According to one embodiment, the monoclonal antibody comprises the three CDRs of the heavy chain variable region of 8C7 Also provided is a monoclonal antibody that further comprises the variable light chain variable region of 8C7 or one, two or three of the CDRs of the light chain variable region of 8C7. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody 8C7 are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, the disclosure provides an antibody, wherein the antibody comprises: a HCDR1 region of 8C7 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 8C7 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 8C7 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 8C7 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR2 region of 8C7 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR3 region of 8C7 comprising an amino acid sequence as set forth in Table A, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Table A for each CDR), those of the Chotia numbering system as indicated in Table A for each CDR), those of the IMGT numbering system as indicated in Table A for each CDR), or any other suitable numbering system.

In another aspect, the disclosure provides an antibody that binds human CD73, comprising:

(a) the hypervariable regions of the heavy chain variable region of SEQ ID NOS: 3, 21, 28 or 36, optionally wherein one, two, three or more amino acids are substituted by a different amino acid; and (b) the hypervariable regions of the light chain variable region of SEQ ID NOS: 3, 22, 29 or 37, optionally wherein one, two, three or more amino acids are substituted by a different amino acid.

In another aspect, the disclosure provides an antibody that binds human CD73, comprising:

(a) a heavy chain CDR 1 amino acid sequence as shown in any one of SEQ ID NOS: 5-7 or 30-32, optionally wherein one, two, three or more amino acids in a CDR may be substituted by a different amino acid;

(b) a heavy chain CDR 2 amino acid sequence as shown in any one of SEQ ID NOS: 8-10, 23, 24 or 33, optionally wherein one, two, three or more amino acids in a CDR may be substituted by a different amino acid;

(c) a heavy chain CDR 3 amino acid sequence as shown in any one of SEQ ID NOS: 11-13, 25 or 27, optionally wherein one, two, three or more amino acids in a CDR may be substituted by a different amino acid;

(d) a light chain CDR 1 amino acid sequence as shown in any one of SEQ ID NOS: 14, 15, 16, 34 or 35 optionally wherein one, two, three or more amino acids in a CDR may be substituted by a different amino acid;

(e) a light chain CDR 2 amino acid sequence as shown in any one of SEQ ID NOS: 17 or 18, optionally wherein one, two, three or more amino acids in a CDR may be substituted by a different amino acid; and/or (f) a light chain CDR 3 amino acid sequence as shown in any one of SEQ ID NOS: 19 or 20, optionally wherein one, two, three or more amino acids in a CDR may be substituted by a different amino acid.

In another aspect of any of the embodiments herein, any of the CDRs 1, 2 and 3 of the heavy and light chains of 11E1, 8C7, 3C12 or 6E1 may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In one aspect of any of the embodiments herein, any antibody may comprise a heavy and/or light chain having CDR1, 2 and/or 3 sequences according to the respective formula selected from the respective Formulas (I) to (V). In any embodiment herein, a particular HCDR1-3 or LCDR-1-3 may be specified as having a sequence of the respective Formulas (I) to (VI). In one 44 preferred embodiment, the antibody comprises a light chain comprising the three LCDRs and a heavy chain comprising the three HCDRs.

In one embodiment, HCDR1 comprises an amino acid sequence of Formula (I):

$$\text{S-Y-N-M-Xaa}_1, \quad \text{(SEQ ID NO: 38)}$$

wherein Xaa$_1$ may be a conservative or non-conservative substitution of any of the amino acids indicated or a deletion or insertion, optionally wherein Xaa$_1$ is Y (Tyr) or N (Asp).

In one embodiment, HCDR2 comprises an amino acid sequence of Formula (IIa):

(SEQ ID NO: 39)
Y-I-D-P-Y-N-G-G-Xaa$_2$-S-Y-N-Xaa$_3$-Xaa$_4$-F-K-G, or a subsequence thereof, e.g., an amino acid sequence of Formula (IIb):

(SEQ ID NO: 40)
Y-I-D-P-Y-N-G-G-Xaa$_2$, wherein Xaa$_2$ may be a conservative or non-conservative substitution of any of the amino acids indicated or a deletion or insertion, optionally wherein Xaa$_2$ is S (Ser) or T (Thr); wherein Xaa$_3$ may be a conservative or non-conservative substitution of any of the amino acids indicated or a deletion or insertion, optionally wherein Xaa$_3$ is Q (Gln) or L (Leu); wherein Xaa$_4$ may be a conservative or non-conservative substitution of any of the amino acids indicated or a deletion or insertion, optionally wherein Xaa$_4$ is K (Lys) or T (Thr).

In one embodiment, HCDR3 comprises an amino acid sequence of Formula (III):

(SEQ ID NO: 41)
G-Y-Xaa$_5$-N-Y-K-A-W-F-A-Y, wherein Xaa$_5$ may be a conservative or non-conservative substitution of any of the amino acids indicated or a deletion or insertion, optionally wherein Xaa$_5$ is G (Gly) or N (Asn).

In one embodiment, LCDR1 comprises an amino acid sequence of Formula (IV):

(SEQ ID NO: 42)
K-A-S-Q-S-V-Xaa$_6$-N-D-V-A, wherein Xaa$_6$ may be a conservative or non-conservative substitution of any of the amino acids indicated or a deletion or insertion, optionally wherein Xaa$_6$ is T (Thr) or S (Ser).

in one embodiment, LCDR2 comprises an amino acid sequence of Formula (V):

(SEQ ID NO: 43)
Y-A-S-Xaa$_7$-R-Y-T, wherein Xaa$_7$ may be a conservative or non-conservative substitution of any of the amino acids indicated or a deletion or insertion, optionally wherein Xaa$_7$ is T (Thr) or N (Asn)

In one embodiment, LCDR3 comprises an amino acid sequence of SEQ ID NO: 19 or 20.

In one embodiment, an antibody may comprise a heavy chain comprising:
  a a heavy chain CDR1 (HCDR1) comprising an amino acid sequence of SEQ ID NO: 38; and/or
  b a heavy chain CDR2 (HCDR2) comprising an amino acid sequence of SEQ ID NO: 39 (or 40); and/or
  c a heavy chain CDR3 (HCDR3) comprising an amino acid sequence of SEQ ID NO: 41.

In one embodiment, an antibody may comprise a light chain comprising:
  a a light chain CDR1 (LCDR1) comprising an amino acid sequence selected from SEQ ID NO: 42; and/or
  b a light chain CDR2 (LCDR2) comprising an amino acid sequence of SEQ ID NO: 43; and/or
  c a light chain CDR3 (LCDR3) comprising an amino acid sequence of SEQ ID NO: 19 or 20.

In any of the antibodies, e.g., 11E1, 8C7, 3C12 or 6E1, the specified variable region and CDR sequences may comprise sequence modifications, e.g. a substitution (1, 2, 3, 4, 5, 6, 7, 8 or more sequence modifications). In one embodiment, a CDRs 1, 2 and/or 3 of the heavy and light chains comprises one, two, three or more amino acid substitutions, where the residue substituted is a residue present in a sequence of human origin. In one embodiment the substitution is a conservative modification. A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for retained function (i.e., the properties set forth herein) using the assays described herein.

The sequences of the CDRs, according to IMGT, Kabat and Chothia definitions systems, have been summarized in Table A below. The sequences of the variable regions of the antibodies are listed in Table B below (if leader sequences are present any antibody chain can be specified to start at the amino acid position immediately following the end of the leader sequence), and each CDRs underlined. In any embodiment herein, a VL or VH sequence can be specified or numbered so as to contain or lack a signal peptide or any part thereof.

TABLE A

| mAb | CDR definition | HCDR1 SEQ ID | HCDR1 Sequence | HCDR2 SEQ ID | HCDR2 Sequence | HCDR3 SEQ ID | HCDR3 Sequence |
|---|---|---|---|---|---|---|---|
| 1E11 | Kabat | 5 | SYNMY | 8 | YIDPYNGGTSYNQKFKG | 11 | GYGNYKAWFAY |
|  | Chotia | 6 | GYAFTSY | 9 | PYNG | 12 | YGNYKAWFA |
|  | IMGT | 7 | GYAFTSYN | 10 | IDPYNGGT | 13 | ARGYGNYKAWFAY |
| 6E1 | Kabat | 5 | SYNMY | 23 | YIDPYNGGSSYNQKFKG | 25 | GYNNYKAWFAY |
|  | Chotia | 6 | GYAFTSY | 9 | PYNG | 26 | YNNYKAWFA |
|  | IMGT | 7 | GYAFTSYN | 24 | IDPYNGGS | 27 | ARGYNNYKAWFAY |
| 8C7 | Kabat | 30 | SYNMN | 33 | YIDPYNGGSSYNLTFKG | 11 | GYGNYKAWFAY |
|  | Chotia | 31 | GYAFASY | 9 | PYNG | 12 | YGNYKAWFA |
|  | IMGT | 32 | GYAFASYN | 24 | IDPYNGGS | 13 | ARGYGNYKAWFAY |
| 3C12 | Kabat | 30 | SYNMN | 33 | YIDPYNGGSSYNLTFKG | 11 | GYGNYKAWFAY |
|  | Chotia | 31 | GYAFASY | 9 | PYNG | 12 | YGNYKAWFA |
|  | IMGT | 32 | GYAFASYN | 24 | IDPYNGGS | 13 | ARGYGNYKAWFAY |

| mAb | CDR definition | LCDR1 SEQ | LCDR1 Sequence | LCDR2 SEQ | LCDR2 Sequence | LCDR3 SEQ ID | LCDR3 Sequence |
|---|---|---|---|---|---|---|---|
| 1E11 | Kabat | 14 | KASO5VINDVA | 17 | YASNRYT | 19 | QQDYSSLT |
|  | Chotia | 15 | SQSVIND | 18 | YAS | 20 | DYSSL |
|  | IMGT | 16 | QSVTND | 18 | YAS | 19 | QQDYSSLT |
| 6E1 | Kabat | 14 | KASQ5VINDVA | 17 | YASNRYT | 19 | QQDYSSLT |
|  | Chotia | 15 | SQSVIND | 18 | YAS | 20 | DYSSL |
|  | IMGT | 16 | QSVTND | 18 | YAS | 19 | QQDYSSLT |
| 8C7 | Kabat | 44 | KASQSVSNDVA | 17 | YASTRYT | 19 | QQDYSSLT |
|  | Chotia | 34 | SQSVSND | 18 | YAS | 20 | DYSSL |
|  | IMGT | 35 | QSVSND | 18 | YAS | 19 | QQDYSSLT |
| 3C12 | Kabat | 38 | KASQSVSNDVA | 17 | YASTRYT | 19 | QQDYSSLT |
|  | Chotia | 34 | SQSVSND | 18 | YAS | 20 | DYSSL |
|  | IMGT | 35 | QSVSND | 18 | YAS | 19 | QQDYSSLT |

TABLE B

| | SEQ ID NO: | Amino Acid Sequence |
|---|---|---|
| 11E1 VH | 3 | EIQLQQSGPELVKPGASVKVSCKASGYAFTSYNMYWVKQSHGKSLEWIGYIDPYNGGTSYNQKFKGKATLTVDKSSSTAYMHLNSLTSEDSAVYYCARGYGNYKAWFAYWGQGTLVTVSA |
| 11E1 VL | 4 | DAVMTQTPKFLLVSAGDRVTITCKASQSVTNDVAWYQQKPGQSPKLLIYYASNRYTGVPDRFTGSGYGTDFTFTISTVQAEDLAVYFCQQDYSSLTFGAGTKLELK |
| 6E1 VH | 21 | EFQLQQSGPELVKPGASVKVSCKASGYAFTSYNMYWVKQSHGKRLEWIGYIDPYNGGSSYNQKFKGKATLTVDKSSSTAYMHLNNLTSEDSAVYYCARGYNNYKAWFAYWGQGTLVTVSA |
| 6E1 VL | 22 | SIVMTQTPKFLLVSAGDRVTITCKASQSVTNDVAWYQQKPGQSPKLLIYYASNRYTGVPDRFTGSGYGTDFTFTISTMQAEDLAVYFCQQDYSSLTFGAGTKLELK |
| 8C7 VH | 28 | EVQLQQSGPELVKPGASVKVSCKASGYAFASYNMNWVKQSHGKSLDWIGYIDPYNGGSSYNLTFKGKATLTVDKSSTTAYMHLNSLTSEDSAVYYCARGYGNYKAWFAYWGQGTLVTVSAASTKGP |
| 8C7 VL | 29 | SIVMTPTPKFLLVSAGDRVTITCKASQSVSNDVAWYQQKPGQSPKLLIYYASTRYTGVPDRFTGSGYGTDFTFTISTVQAEDLAVYFCQQDYSSLTFGAGTKLELKRTVAAP |
| 3C12 VH | 36 | QIQLQQSGPELVKPGASVKVSCKASGYAFASYNMNWVKQSHGKSLDWIGYIDPYNGGSSYNLTFKGKATLTVDKSSTTAYMHLNSLTSEDSAVYYCARGYGNYKAWFAYWGQGTLVTVSAASTKGP |
| 3C12 VL | 37 | DVVMTQTPKFLLVSAGDRVTITCKASQSVSNDVAWYQQKPGQSPKLLIYYASTRYTGVPDRFTGSGYGTDFTFTISTVQAEDLAVYFCQQDYSSLTFGAGTKLELKRTVAAP |

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific (e.g. bispecific) antibodies formed from antibody fragments. Included, inter alia, are a nanobody, domain antibody, single domain antibody or a "dAb".

In certain embodiments, the DNA of a hybridoma producing an antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Optionally an antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for CD73 and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host according that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

Antibody Formulations

An anti-CD73 antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment.

In a further embodiment, the formulation further comprises a pharmaceutically acceptable preservative. In a further embodiment, the formulation further comprises an isotonic agent. In a further embodiment, the formulation also comprises a chelating agent. In a further embodiment the formulation further comprises a stabilizer. In a further embodiment, the formulation further comprises a surfactant. For convenience reference is made to Remington: *The Science and Practice of Pharmacy*, 19$^{th}$ edition, 1995.

It is possible that other ingredients may be present in the peptide pharmaceutical formulation. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation.

Pharmaceutical compositions containing an antibody may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Suitable antibody formulations can also be determined by examining experiences with other already developed therapeutic monoclonal antibodies. Several monoclonal antibodies have been shown to be efficient in clinical situations, such as Rituxan (Rituximab), Herceptin (Trastuzumab) Xolair (Omalizumab), Bexxar (Tositumomab), Campath (Alemtuzumab), Zevalin, Oncolym and similar formulations may be used with the antibodies. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Diagnosis and Treatment of Malignancies

Methods of treating an individual, notably a human patient, using an anti-CD73 antibody as described herein are also provided for. In one embodiment, the disclosure provides for the use of an antibody as described herein in the preparation of a pharmaceutical composition for administration to a human patient. Typically, the patient suffers from, or is at risk for, cancer.

For example, in one aspect, provided is a method of restoring or potentiating the activity of lymphocytes in a patient in need thereof, comprising the step of administering a neutralizing anti-CD73 antibody to said patient. The antibody can be for example a human or humanized anti-CD73 antibody, which antibody reduces or abrogates the 5'-nucleotidase activity of human CD73. In one embodiment, the method directed at increasing the activity of lymphocytes (e.g. T cells) in patients having a disease in which increased lymphocyte activity is beneficial or which is caused or characterized by immunosuppression, immunosuppressive cells, or, e.g., adenosine generated by CD4 T cells, CD8 T cells, B cells). The methods will be particularly useful for example patients having a solid tumor in which it is suspected the tumor microenvironment (and CD73-mediated adenosine production therein) may contribute to lack of recognition by the immune system (immune escape). The tumor may, for example, be characterized by CD73-expressing immune cells, e.g., CD4 T cells, CD8 T cells, B cells.

More specifically, the methods and compositions are utilized for the treatment of a variety of cancers and other proliferative diseases. Because these methods operate by reducing adenosine that inhibits the anti-tumor activity of lymphocytes and possibly additionally by increasing ATP that can increase the anti-tumor activity of lymphocytes, they are applicable to a very broad range of cancers, including in particular solid tumors in which adenosine in the tumor microenvironment may play a strong role in suppressing the anti-tumor immune response. In one embodiment, a human patient treated with an anti-CD73 antibody has liver cancer, bone cancer, pancreatic cancer, skin cancer, cancer of the head or neck, breast cancer, lung cancer, non-small cell lung cancer (NSCLC), castrate resistant prostate cancer (CRPC), melanoma, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present disclosure is also applicable to treatment of metastatic cancers. Patients can be tested or selected for one or more of the above described clinical attributes prior to, during or after treatment.

In one embodiment, the anti-CD73 antibody is administered an amount effective to achieve and/or maintain in an individual (e.g. for 1, 2, 3, 4 weeks, and/or until the subsequent administration of antigen binding compound) a blood concentration of at least the $EC_{50}$, optionally the $EC_{70}$, optionally substantially the $EC_{100}$, for neutralization of the enzymatic activity of CD73. In one embodiment, the active amount of anti-CD73 antibody is an amount effective to achieve the $EC_{50}$, optionally the $EC_{70}$, optionally substantially the $EC_{100}$, for neutralization of the enzymatic activity of CD73 in an extravascular tissue of an individual. In one embodiment, the active amount of anti-CD73 antibody is an amount effective to achieve (or maintain) in an individual the $EC_{50}$, optionally the $EC_{70}$, optionally substantially the $EC_{100}$, for inhibition of neutralize the enzymatic activity of CD73.

Optionally, in one embodiment, in contrast to some antibodies that are directed to the depletion of CD73-expressing tumor cells by ADCC (which, e.g., can provide full efficacy at concentrations equal or substantially lower than that which provides receptor saturation), the anti-CD73 antibody is a pure blocker (no substantial Fcγ receptor-mediated activity) and is administered in an amount effective to neutralize the enzymatic activity of CD73 for a desired period of time, e.g. 1 week, 2 weeks, a month, until the next successive administration of anti-CD73 antibody.

In one embodiment, the anti-CD73 antibody is administered in an amount effective to achieve and/or maintain (e.g. for 1, 2, 3, 4 weeks, and/or until the subsequent administration of anti-CD73 antibody) in an individual a blood concentration of at least the $EC_{50}$, optionally the $EC_{70}$, optionally substantially the $EC_{100}$, for inhibition of CD73-mediated catabolism of AMP to adenosine (e.g., by assessing neutralization of 5' ectonucleotidase activity in MDA-MB-231 cells by quantifying hydrolysis of AMP to adenosine, see Example 5). In one embodiment, the amount of anti-CD73 antibody is an amount effective to achieve (or maintain) the $EC_{50}$, optionally the $EC_{70}$, optionally substantially the $EC_{100}$, for inhibition of CD73-mediated catabolism of AMP to adenosine in an extravascular tissue of an individual.

In one embodiment, provided is a method for treating or preventing cancer in an individual, the method comprising administering to an individual having disease an anti-CD73 antibody in an amount that achieves or maintains for a specified period of time a concentration in circulation, optionally in an extravascular tissue of interest (e.g. the tumor or tumor environment), that is higher than the concentration required for 50%, 70%, or full (e.g. 90%) receptor saturation CD73-expressing cells in circulation (for example as assessed in PBMC). Optionally the concentration achieved is at least 20%, 50% or 100% higher than the concentration required for the specified receptor saturation.

In one embodiment, provided is a method for treating or preventing cancer in an individual, the method comprising administering to the individual an anti-CD73 antibody in an amount that achieves or maintains for a specified period of time a concentration in circulation, optionally in an extravascular tissue of interest (e.g. the tumor or tumor environment), that is higher than the $EC_{50}$, optionally $EC_{70}$ or optionally $EC_{100}$, for binding to CD73-expressing cells (e.g., as assessed by titrating anti-CD73 antibody on CD73-expressing cells, for example MDA-MB-231 cells as in Example 4). Optionally the concentration achieved is at least 20%, 50% or 100% higher than the $EC_{50}$, optionally $EC_{70}$ or optionally $EC_{100}$, for binding to CD73-expressing cells.

In any embodiment, the antibody can for example have an $EC_{50}$, optionally $EC_{70}$ or optionally $EC_{100}$, for binding to CD73-expressing cells in human PBMC of between 0.5-100 ng/ml, optionally 1-100 ng/ml, optionally 30-100 ng/ml, e.g. about 30-90 ng/ml, (e.g., as assessed by titrating anti-CD73 antibody on CD73-expressing cells, for example MDA-MB-231 cells as in Example 4). For example the $EC_{50}$ may be about 30, 37, 39, 43, 57, 58, 61, 62, 90, 95, 143 ng/ml.

The $EC_{50}$ for neutralization of the enzymatic activity of CD73 with the anti-CD73 antibody can be for example between about 0.01 µg/ml and 1 µg/ml, optionally between 0.1 µg/ml and 10 µg/ml, optionally between 0.1 µg/ml and 1 µg/ml. For example the $EC_{50}$ may be about 0.1 µg/ml, about 0.2 µg/ml or about 0.3 µg/ml. Thus an amount of this anti-CD73 antibody is for example administered so at to achieve and/or maintain a blood concentration of at least 0.1 µg/ml, optionally at least 0.2 µg/ml, optionally at least 1 µg/ml, or optionally at least 2 µg/ml.

When tissues outside of the vasculature are targeted (the tumor environment, e.g., in the treatment of solid tumors), an approximately 10-fold higher dose is typically believed to be needed, compared to the dose that provides the corresponding concentration in circulation. An amount of anti-CD73 antibody administered so at to achieve (and/or maintain) a concentration in circulation (blood) of about 1 µg/ml, 2 µg/ml, 10 µg/ml, or 20 µg/ml is expected to achieve (and/or maintain) an extravascular tissue (e.g. tumor tissue) concentration of about 0.1 µg/ml, 0.2 µg/ml, 1 µg/ml, 2 µg/ml, respectively.

In one embodiment, an anti-CD73 antibody is for example administered in an amount so at to achieve and/or maintain a tissue (e.g. tumor environment) concentration of at least 0.1 µg/ml, optionally at least 0.2 µg/ml, optionally at least 1 µg/ml, or optionally at least 2 µg/ml. The antibody can for example be administered in an amount to achieve and/or maintained a blood concentration of at least about 1 µg/ml, 2 µg/ml, 10 µg/ml, or 20 µg/ml, e.g. between 1-100 µg/ml, 10-100 µg/ml, 1-50 µg/ml, 1-20 µg/ml, or 1-10 µg/ml. The amount administered can be adjusted to as to provide for maintenance of the desired concentration for the duration of a specified period of time following administration (e.g. 1, 2, 3, 4 weeks, etc).

In some embodiments, an amount of anti-CD73 antibody is administered so as to obtain a concentration in blood (serum) or an extravascular tissue (e.g. tumor environment) that corresponds to at least the $EC_{70}$ or the $EC_{100}$ for neutralization of the enzymatic activity of CD73. The antibody can for example be administered in an amount to achieve and/or maintained a blood concentration or an extravascular tissue (e.g. tumor environment) of at least about 1 µg/ml, 2 µg/ml, 10 µg/ml, or 20 µg/ml.

The $EC_{50}$, $EC_{70}$ or the $EC_{100}$ can be assessed for example in a cellular assay for neutralization of the enzymatic activity of CD73 as shown in the Examples herein (e.g. neutralization of 5' ectonucleotidase activity in MDA-MB-231 cells by quantifying hydrolysis of AMP to adenosine, see Example 5). "$EC_{50}$" with respect to neutralization of the enzymatic activity of CD73, refers to the efficient concentration of anti-CD73 antibody which produces 50% of its maximum response or effect with respect to neutralization of the enzymatic activity.). "$EC_{70}$" with respect to neutralization of the enzymatic activity of CD73, refers to the efficient concentration of anti-CD73 antibody which produces 70% of its maximum response or effect. "$EC_{100}$" with respect to neutralization of the enzymatic activity of CD73, refers to the efficient concentration of anti-CD73 antibody which produces its substantially maximum response or effect with respect to such neutralization of the enzymatic activity.

In some embodiments, particularly for the treatment of solid tumors, the concentration achieved is designed to lead to a concentration in tissues (outside of the vasculature, e.g. in the tumor or tumor environment) that corresponds to at least the $EC_{50}$ for neutralization of the enzymatic activity, optionally at about, or at least about, the $EC_{100}$.

In one embodiment, the amount of anti-CD73 antibody is between 1 and 20 mg/kg body weight. In one embodiment, the amount is administered to an individual weekly, every two weeks, monthly or every two months.

In one embodiment provided is a method of treating a human individual having a cancer, comprising administering to the individual an effective amount of an anti-CD73 antibody of the disclosure for at least one administration cycle (optionally at least 2, 3, 4 or more administration cycles), wherein the cycle is a period of eight weeks or less, wherein for each of the at least one cycles, one, two, three or four doses of the anti-CD73 antibody are administered at a dose of 1-20 mg/kg body weight. In one embodiment, the anti-CD73 antibody is administered by intravenous infusion.

Suitable treatment protocols for treating a human include, for example, administering to the patient an amount as disclosed herein of an anti-CD73 antibody, wherein the method comprises at least one administration cycle in which at least one dose of the anti-CD73 antibody is administered. Optionally, at least 2, 3, 4, 5, 6, 7 or 8 doses of the anti-CD73 antibody are administered. In one embodiment, the administration cycle is between 2 weeks and 8 weeks.

In one embodiment, provided is a method for treating or preventing a disease (e.g. a cancer, a solid tumor, a hematological tumor) in an individual, the method comprising administering to an individual having disease (e.g. a cancer, a solid tumor) an anti-CD73 antibody that neutralizes the enzymatic activity of CD73 for at least one administration cycle, the administration cycle comprising at least a first and second (and optionally a $3^{rd}$, $4^{th}$, $5^{th}$ $6^{th}$, $7^{th}$ and/or $8^{th}$ or further) administration of the anti-CD73 antibody, wherein the anti-CD73 antibody is administered in an amount effective to achieve, or to maintain between two successive administrations, a blood (serum) concentration of anti-CD73 antibody of at least 0.1 µg/ml, optionally at least 0.2 µg/ml, optionally at least 1 µg/ml, or optionally at least 2 µg/ml (e.g. for treatment of a hematological tumor), or optionally at least about 1 µg/ml, 2 µg/ml, 10 µg/ml, or 20 µg/ml, e.g. between 1-100 µg/ml, 1-50 µg/ml, 1-20 µg/ml, or 1-10 µg/ml (e.g. for treatment of a solid tumor, for treatment of a hematological tumor). In one embodiment, a specified continuous blood concentration is maintained, wherein the blood concentration does not drop substantially below the specified blood concentration for the duration of the specified time period (e.g. between two administrations of antibody, number of weeks, 1 week, 2 weeks, 3 weeks, 4 weeks), i.e. although the blood concentration can vary during the specified time period, the specified blood concentration maintained represents a minimum or "trough" concentration. In one embodiment, a therapeutically active amount of an anti-CD73 antibody is an amount of such antibody capable of providing (at least) the $EC_{50}$ concentration, optionally the $EC_{70}$ concentration optionally the $EC_{100}$ concentration, in blood and/or in a tissue for neutralization of the enzymatic activity of CD73 for a period of at least about 1 week, about 2 weeks, or about one month, following administration of the antibody.

Prior to or during a course of treatment with an anti-CD73 antibody of the disclosure, presence or levels or CD73-expressing cells, adenosine, ADP and/or AMP levels can be assessed within and/or adjacent to a patient's tumor to assess whether the patient is suitable for treatment (e.g. to predict whether the patient is likely to respond to treatment). Increased presence or levels or CD73-expressing cells, levels of adenosine, ADP and/or AMP may indicate an individual is suitable for treatment with (e.g. likely to benefit from) an anti-CD73 antibody of the disclosure (including but not limited to an antibody that inhibits substrate-bound CD73).

Prior to or during a course of treatment with an anti-CD73 antibody of the disclosure, adenosine, ADP and/or AMP levels can also be assessed within and/or adjacent to a patient's tumor to assess whether the patient is benefitting from treatment with an anti-CD73 antibody. Decreased levels of adenosine, ADP and/or AMP compared following an administration (or dosing of antibody) compared to levels prior to treatment (or dosing of antibody) may indicate an individual is benefitting from treatment with an anti-CD73 antibody of the disclosure (including but not limited to an antibody that inhibits substrate-bound CD73). Optionally, if a patient is benefitting from treatment with the anti-CD73 antibody, methods can further comprise administering a further dose of the anti-CD73 antibody to the patient (e.g., continuing treatment).

In one embodiment, assessing adenosine, ADP and/or AMP levels within and/or adjacent to a patient's tumor the tissue sample comprises obtaining from the patient a biological sample of a human tissue selected from the group consisting of tissue from a cancer patient, e.g., cancer tissue, tissue proximal to or at the periphery of a cancer, cancer adjacent tissue, adjacent non-tumorous tissue or normal adjacent tissue, and detecting adenosine, ADP and/or AMP levels within the tissue. The levels from the patient can be comparing the level to a reference level, e.g. corresponding to a healthy individual.

In one embodiment, the disclosure provides a method for the treatment or prevention of a cancer in an individual in need thereof, the method comprising:

a) detecting CD73-expressing cells (or adenosine, ADP and/or AMP) the tumor environment, optionally within the tumor and/or within adjacent tissue, and b) upon a determination that tumor environment comprises CD73-expressing cells (or adenosine, ADP and/or AMP), optionally at a level that is increased compared to a reference level, administering to the individual an anti-CD73 antibody. Optionally, detecting CD73-expressing cells (or adenosine, ADP and/or AMP) within the tumor environment comprises obtaining from the individual a biological sample that comprises cancer tissue and/or tissue proximal to or at the periphery of a cancer (e.g., cancer adjacent tissue, adjacent non-tumorous tissue or normal adjacent tissue), and detecting levels of CD73-expressing cells (or adenosine, ADP and/or AMP). CD73-expressing cells may comprise, for example, tumor cells, CD4 T cells, CD8 T cells, B cells.

A patient having a cancer can be treated with the anti-CD73 antibody with our without a prior detection step to assess expression of CD73 on cells in the tumor microenvironment (e.g. on tumor cells, CD4 T cells, CD8 T cells, B cells). Optionally, the treatment methods can comprises a step of detecting a CD73 nucleic acid or polypeptide in a biological sample of a tumor from an individual (e.g., in cancer tissue, tissue proximal to or at the periphery of a cancer, cancer adjacent tissue, adjacent non-tumorous tissue or normal adjacent tissue). A determination that a biological sample comprises cells expressing CD73 (e.g. prominently expressing; expressing CD73 at a high level, high intensity of staining with an anti-CD73 antibody, compared to a reference) indicates that the patient has a cancer that may have a strong benefit from treatment with an agent that inhibits CD73. In one embodiment, the method comprises determining the level of expression of a CD73 nucleic acid or polypeptide in a biological sample and comparing the level to a reference level corresponding to a healthy individual. A determination that a biological sample comprises cells expressing CD73 nucleic acid or polypeptide at a level that is increased compared to the reference level indicates that the patient has a cancer that can be treated with an anti-CD73 antibody of the disclosure. Optionally, detecting a CD73 polypeptide in a biological sample comprises detecting CD73 polypeptide expressed on the surface of a malignant cell, a CD4 T cell, CD8 T cell, B cell. In one embodiment, a determination that a biological sample comprises cells that prominently expresses CD73 nucleic acid or polypeptide indicates that the patients has a cancer that can be treated with an anti-CD73 antibody of the disclosure. "Prominently expressed", when referring to a CD73 polypeptide, means that the CD73 polypeptide is expressed in a substantial number of cells taken from a given patient. While the definition of the term "prominently expressed" is not bound by a precise percentage value, in some examples a receptor said to be "prominently expressed" will be present on at least 10%, 20% 30%, 40%, 50° %, 60%, 70%, 80%, or more of the tumor cells taken from a patient.

Determining whether an individual has a cancer characterized by cells that express a CD73 polypeptide can for example comprise obtaining a biological sample (e.g. by performing a biopsy) from the individual that comprises cells from the cancer environment (e.g. tumor or tumor adjacent tissue), bringing said cells into contact with an antibody that binds an CD73 polypeptide, and detecting whether the cells express CD73 on their surface.

Optionally, determining whether an individual has cells that express CD73 comprises conducting an immunohistochemistry assay.

In one embodiment, the disclosure provides a method for the treatment or prevention of a cancer in an individual in need thereof, the method comprising:

a) determining the CD73 polypeptide status of cells within the tumor environment, optionally within the tumor and/or within adjacent tissue, and b) upon a determination that tumor environment comprises cells that express CD73 polypeptide, optionally at a level that is increased compared to a reference level, administering to the individual an anti-CD73 antibody. In one embodiment, the cells are tumor cells. In another embodiment, the cells within the tumor environment, tumor and/or adjacent tissue are non-malignant immune cells, e.g., T cells. Optionally, determining the CD73 polypeptide status within the tumor environment comprises obtaining from the individual a biological sample that comprises cancer tissue and/or tissue proximal to or at the periphery of a cancer (e.g., cancer adjacent tissue, adjacent non-tumorous tissue or normal adjacent tissue), bringing said cells into contact with an antibody that binds a CD73 polypeptide, and detecting cells that express CD73.

The antibody compositions may be used in as monotherapy or combined treatments with one or more other therapeutic agents, including agents normally utilized for the particular therapeutic purpose for which the antibody is being administered. The additional therapeutic agent will normally be administered in amounts and treatment regimens typically used for that agent in a monotherapy for the particular disease or condition being treated. Such therapeutic agents include, but are not limited to anti-cancer agents and chemotherapeutic agents.

In one embodiment, the second or additional second therapeutic agent is an antibody or other Fc domain-containing protein capable of inducing ADCC toward a cell to which it is bound, e.g. via CD16 expressed by an NK cell. Typically, such antibody or other protein will comprise a domain that binds to an antigen of interest, e.g. an antigen present on a tumor cell (tumor antigen), and an Fc domain or portion thereof, and will exhibit binding to the antigen via the antigen binding domain and to Fcγ receptors (e.g. CD16) via the Fc domain. In one embodiment, its ADCC activity will be mediated at least in part by CD16. In one embodiment, the additional therapeutic agent is an antibody having a native or modified human Fc domain, for example a Fc domain from a human IgG1 or IgG3 antibody. The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils. The term "ADCC-inducing antibody" refers to an antibody that demonstrates ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody.

In one embodiment, the second or additional second therapeutic agent is an agent (e.g., an antibody) that inhibits CTLA-4 or the PD-1 axis (i.e. inhibits PD-1 or PD-L1). Antibodies that bind CTLA-4, PD1 or PD-L1 can be used, for example, at the exemplary doses and/or frequencies that such agents are used as monotherapy, e.g., as described below.

PD-1 is an inhibitory member of the CD28 family of receptors that also includes CD28, CTLA-4, ICOS and BTLA. PD-1 is expressed on activated B cells, T cells, and myeloid cells Okazaki et al. (2002) Curr. Opin. Immunol. 14: 391779-82; Bennett et al. (2003) J Immunol 170:711-8). Two ligands for PD-1 have been identified, PD-L1 and PD-L2, that have been shown to downregulate T cell activation upon binding to PD-1 (Freeman et al. (2000) J Exp Med 192:1027-34; Latchman et al. (2001) Nat Immunol 2:261-8; Carter et al. (2002) Eur J Immunol 32:634-43). PD-L1 is abundant in a variety of human cancers (Dong et al. (2002) Nat. Med. 8:787-9). The interaction between PD-1 and PD-L1 results in a decrease in tumor infiltrating lymphocytes, a decrease in T-cell receptor mediated proliferation, and immune evasion by the cancerous cells. Immune suppression can be reversed by inhibiting the local interaction of PD-1 with PD-L1, and the effect is additive when the interaction of PD-1 with PD-L2 is blocked as well. Blockade of PD-1 can advantageously involve use of an antibody that prevents PD-L1-induced PD-1 signalling, e.g. by blocking the interaction with its natural ligand PD-L1. In one aspect the antibody binds PD-1 (an anti-PD-1 antibody); such antibody may block the interaction between PD-1 and PD-L1 and/or between PD-1 and PD-L2. In another aspect the antibody binds PD-L1 (an anti-PD-L1 antibody) and blocks the interaction between PD-1 and PD-L1.

There are currently at least six agents blocking the PD-1/PD-L1 pathway that are marketed or in clinical evaluation, any of these may be useful in combination with the anti-CD73 antibodies of the disclosure. One agent is BMS-936558 (Nivolumab/ONO-4538, Bristol-Myers Squibb; formerly MDX-1106). Nivolumab, (Trade name Opdivo®) is an FDA-approved fully human IgG4 anti-PD-L1 mAb that inhibits the binding of the PD-L1 ligand to both PD-1 and CD80 and is described as antibody 5C4 in WO 2006/121168, the disclosure of which is incorporated herein by reference. For melanoma patients, the most significant OR was observed at a dose of 3 mg/kg, while for other cancer types it was at 10 mg/kg. Nivolumab is generally dosed at 10 mg/kg every 3 weeks until cancer progression.

MK-3475 (human IgG4 anti-PD1 mAb from Merck), also referred to as lambrolizumab or pembrolizumab (Trade name Keytruda®) has been approved by the FDA for the treatment of melanoma and is being tested in other cancers. Pembrolizumab was tested at 2 mg/kg or 10 mg/kg every 2 or 3 weeks until disease progression. DNA constructs encoding the variable regions of the heavy and light chains of the humanized antibodies h409 All have been deposited with the American Type Culture Collection Patent Depository (10801 University Blvd., Manassas, Va.). The plasmid containing the DNA encoding the heavy chain of h409A-1 1 was deposited on Jun. 9, 2008 and identified as 081469_SPD-H and the plasmid containing the DNA encoding the light chain of h409Al 1 was deposited on Jun. 9, 2008 and identified as 0801470_SPD-L-I 1.

MPDL3280A/RG7446 (anti-PD-L1 from Roche/Genentech) is a human anti-PD-L1 mAb that contains an engineered Fc domain designed to optimize efficacy and safety by minimizing FcγR binding and consequential antibody-dependent cellular cytotoxicity (ADCC). Doses of ≤1, 10, 15, and 25 mg/kg MPDL3280A were administered every 3 weeks for up to 1 year. In phase 3 trial, MPDL3280A is administered at 1200 mg by intravenous infusion every three weeks in NSCLC.

AMP-224 (Amplimmune and GSK) is an immunoadhesin comprising a PD-L2 extracellular domain fused to an Fc domain.

Pidlizumab (CT-011; CureTech) (humanized IgG1 anti-PD1 mAb from CureTech/Teva), Pidlizumab (CT-011; CureTech) (see e.g., WO2009/101611) Thirty patients with rituximab-sensitive relapsed FL were treated with 3 mg/kg intravenous CT-011 every 4 weeks for 4 infusions in combination with rituximab dosed at 375 mg/m2 weekly for 4 weeks, starting 2 weeks after the first infusion of CT-011.

Further known PD-1 antibodies and other PD-1 inhibitors include AMP-224 (a B7-DC/IgG1 fusion protein licensed to GSK), AMP-514 described in WO 2012/145493, antibody MEDI-4736 (an anti-PD-L1 developed by AstraZeneca/Medimmune) described in WO2011/066389 and US2013/034559, antibody YW243.55.S70 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/014708, WO2009/114335 and WO2013/019906, the disclosures of which are hereby incorporated by reference. Further examples of anti-PD1 antibodies are disclosed in WO2015/085847 (Shanghai Hengrui Pharmaceutical Co. Ltd.), for example antibodies having light chain variable domain CDR1, 2 and 3 of SEQ ID NO: 6, SEQ ID NO: 7 and/or SEQ ID NO: 8, respectively, and antibody heavy chain variable domain CDR1, 2 and 3 of SEQ ID NO: 3, SEQ ID NO: 4 or SEQ ID NO: 5, respectively, wherein the SEQ ID NO references are the numbering according to WO2015/085847, the disclosure of which is incorporated herein by reference. Antibodies that compete with any of these antibodies for binding to PD-1 or PD-L1 also can be used.

CTLA-4 (cytotoxic T-lymphocyte-associated protein 4), also known as CD152 is another inhibitory member of the CD28 family of receptors, and is expressed on T cells. Antibodies that bind and inhibit CTLA-4 are known in the art. In one example, the antibody is ipilimumab (trade name Yervoy®, Bristol-Myers Squibb), a human IgG antibody. An exemplary administration regimen for Yervoy is 3 mg/kg invtravenously over 90 minutes every three weeks. In one example, the antibody used in combination with the anti-CD73 antibodies of the disclosure is an antibody that competes with ipilimumab for binding to CTLA-4.

In the treatment methods, the CD73-binding compound and the second therapeutic agent can be administered separately, together or sequentially, or in a cocktail. In some embodiments, the antigen-binding compound is administered prior to the administration of the second therapeutic agent. For example, the CD73-binding compound can be administered approximately 0 to 30 days prior to the administration of the second therapeutic agent. In some embodiments, an CD73-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, a CD73-binding compound is administered concurrently with the administration of the therapeutic agents. In some embodiments, a CD73-binding compound is administered after the administration of the second therapeutic agent. For example, a CD73-binding compound can be administered approximately 0 to 30 days after the administration of the second therapeutic agent. In some embodiments, a CD73-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

EXAMPLES

Example 1: Generation of New Anti-huCD73 Antibodies

To obtain anti-human CD73 antibodies, Balb/c mice were immunized with a recombinant human CD73-His extracellular domain recombinant protein (cloned and produced at Innate Pharma as described below). Mice received one primo-immunization with an emulsion of 50 µg CD73 protein and Complete Freund Adjuvant, intraperitoneally, a 2nd immunization with an emulsion of 50 µg CD73 protein and Incomplete Freund Adjuvant, intraperitoneally, and finally a boost with 10 µg CD73 protein, intravenously.

Immune spleen cells were fused 3 days after the boost with X63.Ag8.653 immortalized B cells, and cultured in the presence of irradiated spleen cells. Hydridomas were plated in semi-solid methylcellulose-containing medium and growing clones were picked using a clonepix 2 apparatus (Molecular Devices)

Primary screen: Supernatant (SN) of growing clones were tested in a primary screen by flow cytometry using parental and huCD73-, cynoCD73- or moCD73-expressing recombinant host cell lines. HuCD73- and cynoCD73-expressing recombinant host cells were stained with 0.35 µM and 0.035 µM CFSE, respectively. For the flow cytometry screening, all cells were equally mixed and the presence of reacting antibodies in supernanants was revealed by Goat anti-mouse polyclonal antibody (pAb) labeled with PE. 47 antibodies were found to bind both human and cynomolgus CD73. All antibodies that bound huCD73 and cynoCD73 were produced as chimeric human IgG1 antibodies with a heavy chain N297Q (Kabat EU numbering) mutation which results in lack of N-linked glycosylation and substantial lack of binding to Fcγ receptors.

Secondary screen: this informative screen (see Example 2) was done on recombinant CD73 protein to evaluate the CD73 enzymatic activity blockade properties of the 47-selected antibodies. 35/47 antibodies appear to completely or partially block CD73 activity.

Cloning, production and purification of recombinant huCD73

Molecular Biology

The huCD73 protein was cloned from MIAPACA-2 cDNA using the following primers TACGACTCA-CAAGCTTGCCGCCACCATGTGTCCCCGAGC-CGCGCG (SEQ ID NO: 45) (Forward) and CCGC-CCCGACTCTAGAtcaGTGATGGTGATGATGGTGctt gatccgaccttcaactg SEQ ID NO: 46) (Reverse). The purified PCR product was then cloned into an expression vector using the InFusion cloning system. A 6×His tag was added in the C-terminal part of the protein for the purification step.

Amino acid sequence of the cloned huCD73:

```
                                    (SEQ ID NO: 2)
M C P R A A R A P A T L L L A L G A V L W P A A G A

W E L T I L H T N D V H S R L E Q T S E D S S K C V

N A S R C M G G V A R L F T K V Q Q I R R A E P N V

L L L D A G D Q Y Q G T I W F T V Y K G A E V A H F

M N A L R Y D A M A L G N H E F D N G V E G L I E P

L L K E A K F P I L S A N I K A K G P L A S Q I S G

L Y L P Y K V L P V G D E V V G I V G Y T S K E T P

F L S N P G T N L V F E D E I T A L Q P E V D K L K

T L N V N K I I A L G H S G F E M D K L I A Q K V R

G V D V V V G G H S N T F L Y T G N P P S K E V P A

G K Y P F I V T S D D G R K V P V V Q A Y A F G K Y

L G Y L K I E F D E R G N V I S S H G N P I L L N S

S I P E D P S I K A D I N K W R I K L D N Y S T Q E

L G K T I V Y L D G S S Q S C R F R E C N M G N L I

C D A M I N N N L R H T D E M F W N H V S M C I L N

G G G I R S P I D E R N N G T I T W E N L A A V L P

F G G T F D L V Q L K G S T L K K A F E H S V H R Y

G Q S T G E F L Q V G G I H V V Y D L S R K P G D R

V V K L D V L C T K C R V P S Y D P L K M D E V Y K

V I L P N F L A N G G D G F Q M I K D E L L R H D S

G D Q D I N V V S T Y I S K M K V I Y P A V E G R I

K H H H H H H.
```

Expression and Purification of the huCD73 Proteins

After validation of the sequence cloned, cells were nucleofected and the producing pool was then sub-cloned to obtain a cell clone producing the huCD73 protein. Supernatant from the huCD73 clone grown in roller was harvested and purified using Ni-NTA column and eluted using 250 mM imidazole. The purified proteins were then loaded onto a S200 size exclusion chromatography column. The purified protein corresponding to a dimer was formulated in a Tris 20 mM pH 7.5, NaCl 120 mM and CaCl2 4 mM buffer for enzyme activity assays, while formulation buffer is supplemented with 20% glycerol.

Example 2: Evaluation of Soluble CD73 Blockade

The ability of anti-CD73 antibodies to block enzymatic activity of CD73 was evaluated as described in Sachsenmeier et al. (J Biomol Screening, 2012). Briefly, 500 ng/ml of recombinant human CD73-his were incubated in white 96W flat bottom microplates in presence of dose-range of anti-CD73 or isotype control Abs. Plates were incubated for 1h at 37° C. 12.5 µM ATP and 125 µM AMP were added to each well and plates are incubated at 37° C. for 30 supplemental minutes. Luciferase/luciferin-containing Cell Titer Glo (Promega) is added into wells, plates were incubated for 5 minutes at RT in the dark and emitted light is measured using an Enspire apparatus (Perkin Elmer).

Excess of AMP is known to block ATP-dependent luciferase activity. Addition of CD73 that cleaves AMP into adenosine+inorganic phosphate restores luciferase activity and light emission. Thus, antibodies that block enzymatic activity of CD73 will diminish light emission.

The percentage of enzyme inhibition is evaluated as described below:

Conditions:
ATP+AMP: maximal luciferase inhibition (100%)
ATP+AMP+CD73: no luciferase inhibition (0%)
Formula:

$$\text{Residual } CD73 \text{ activity:} \frac{(CD73 + Ab + ATP + AMP) - (ATP + AMP)}{(CD73 + ATP + AMP) - (ATP + AMP)} * 100$$

35 antibodies obtained in Example 1, as well as reference mAbs 7G2, 4G4 and 1E9, were all found to inhibit CD73 activity using this experimental setting.

Considering the mixed results reported with reference antibodies, we considered whether CD73 blockade may arise from cross-linking of CD73 dimers by bivalent antibodies rather than true blockade of the enzymatic site. That is, antibodies may be causing oligomeric complexes of the CD73 dimers since bivalently binding mAbs may bind to two different CD73 homodimers, in turn leading to larger protein complexes). We then tested this possibility by performing blocking assays at high ratios of antibody:CD73 dimers. In this setting the mAbs are in large excess and induction of oligomeric complexes may occur, permitting true CD73 functional blockade to be observed. In this setting, practically all antibodies, including the reference mAbs 4G4 and 1E9, did not inhibit the enzymatic activity of CD73.

Antibodies 11E1, 8C7, 3C12 and 6E1 functionally blocked CD73 at all concentrations tested. Exemplary results are shown in FIG. 1 for mAbs 11E1, 8C7 and 6E1. A further antibody (results not shown) was subsequently found to have low affinity for CD73 expressed on the surface of cells, thus possibly representing an epitope that is not suitable for high affinity binding to cell surface CD73. Available anti-CD73 reference antibodies reported in recent publications were also tested: 7G2, 4G4 and 1E9 were evaluated for CD73 blockade. Results (see FIG. 1) showed that 7G2 blocked CD73 whereas 4G4 and 1E9 did not block CD73 activity, as residual enzyme activity rebounded to about the starting level or the negative control. Antibody AD2 was also tested and found not to block CD73 activity at any concentration. 4G4 and 1E9 are thus representative of the class of antibodies that non-specifically inhibit CD73 in this assay, possibly by causing oligomerization in solution. Thus, antibodies 7G2, 11E1, 8C7, 3C12 and 6E1 functionally blocked CD73 in this assay.

The $EC_{50}$ values for CD73 blockade are shown in the table below.

| Ab | EC50 (µg/ml) |
|---|---|
| 1E11 | 0.41 |
| 6E1 | 0.33 |
| 8C7 | 1.29 |
| 3C12 | 0.41 |

Example 3: Ab Titration on Rec CD73 Protein by ELISA

Antibodies that functionally blocked soluble recombinant CD73 were more fully characterized for binding to soluble recombinant human CD73.

5 µg/ml of recombinant human CD73 protein (IPH, isoform E6) was coated on MaxiSorp ELISA plates (Nunc) in PBS, overnight at 4° C. Plates were washed 5 times in washing buffer (PBS, 0.05% Tween20) and unspecific sites were saturated by adding 200 µl/w TBS starting block buffer (Thermo Ficher). Dose-range of anti-CD73 antibodies were incubated for 2h at 37° C. Plates were washed 5 times in washing buffer and HRP-coupled goat anti-human or goat anti-mouse IgG Fc fragment secondary antibody (Bethyl, 1/50000) was added for 1 hr at RT to detect bound anti-CD73 antibodies. Plates were washed 5 times in washing buffer and bound secondary antibody is revealed by adding TMB (HRP substrate) and incubating plates for 5 to 10 min at RT in the dark. The enzymatic reaction was stopped by adding HCl 1M and O.D. was measured at 450 nm. Optical density vs. anti-CD73 Ab concentration was plotted on graphs and EC50 is calculated using GraphPad Prism software.

Figure 2:
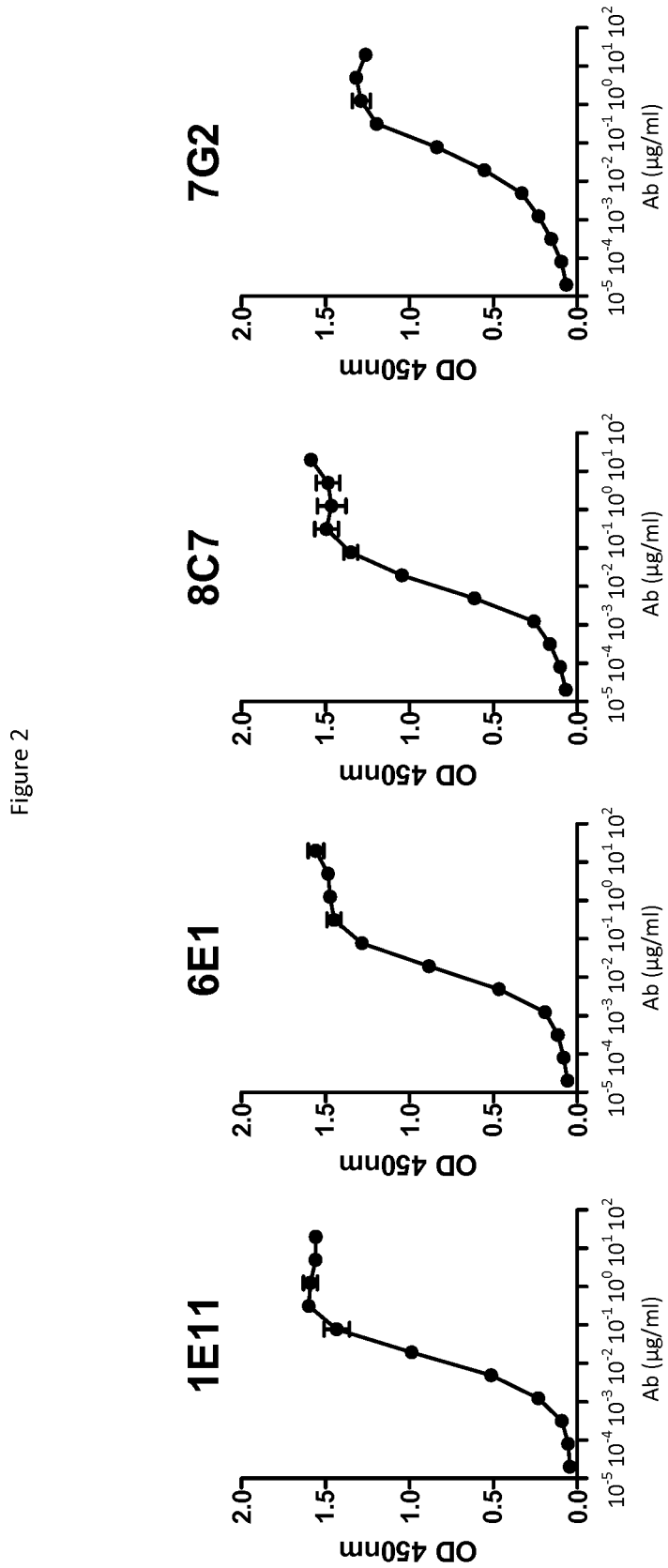
FIG. 2 show the results of titration of antibodies by ELISA on soluble recombinant human CD73 polypeptide.

Results are shown in FIG. 2. Antibodies, 11E1, 8C7, 6E1 and 7G2 all bound soluble recombinant CD73. $EC_{50}$ values for binding are shown in the table below.

| Antibody | EC50 (µg/ml) |
|---|---|
| 11E1 | 0.012 |
| 6E1 | 0.014 |
| 8C7 | 0.009 |
| 3C12 | 0.014 |
| 7G2 | 0.037 |

Example 4: Flow Cytometry Titration

Human-, cynomolgus- and mouse-CD73-expressing recombinant host cell lines or human MDA-MB-231 breast adenocarcinoma that endogenously expresses CD73 were used to evaluate ability of anti-CD73 antibodies to bind human CD73 and to cross-react on cynomolgus and/or mouse CD73. MDA-MB-231 cells are available from ATCC (reference HTB-26). $10^5$ cells resuspended in PBS/0.2% BSA/0.02% NaN3 (named "staining buffer") are distributed into round bottom 96W-microplates. Dose-range of anti-CD73 antibodies was added to the plates and cells are incubated for 45 min at 4° C. Cells were washed three times in staining buffer by spinning plates at 400 g for 3 min at 4° C. PE-coupled goat anti-mouse or goat anti-human IgG Fc fragment secondary antibodies (Beckman Coulter) diluted in staining buffer were added to the cells and plates are incubated for 30 additional minutes at 4° C. Cells were washed three times as described above and analyzed on an Accury C6 flow cytometer equipped with an HTFC plate reader.

Median of fluorescence vs. antibodies concentration was plotted on graphs and EC50 is calculated using GraphPad Prism program.

Figure 3:
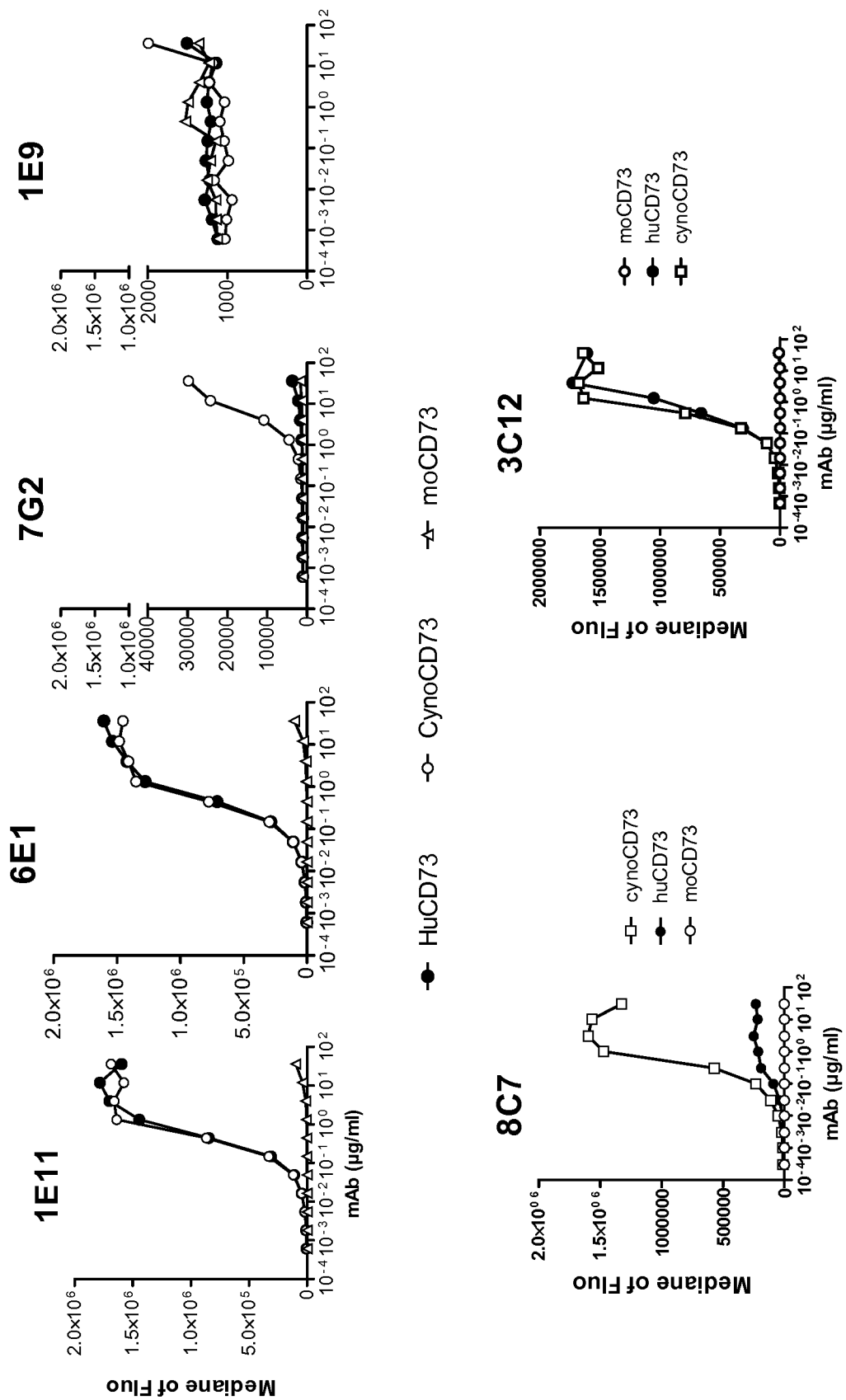
FIG. 3 shows results of titration of antibodies by flow cytometry on human-, cynomolgus- and mouse-CD73-expressing recombinant host cell lines. 11E1, 8C7, 3C12 and 6E1, but not 7G2 or 1E9, bind to recombinant host cells expressing human and cynomolgus (but not mouse) CD73 with excellent affinity.

Results are shown in FIG. 3 for new mAbs 11E1, 8C7, 3C12 and 6E1, as well as reference mAbs 7G2 and 1E9. mAbs 11E1, 8C7, 3C12 and 6E1 bind to recombinant host cells expressing human or cynomolgus (but not mouse) CD73 with excellent affinity. MAbs 7G2 and 1E9, however, show poor binding to cells expressing human or cynomolgus CD73.

Figure 4:
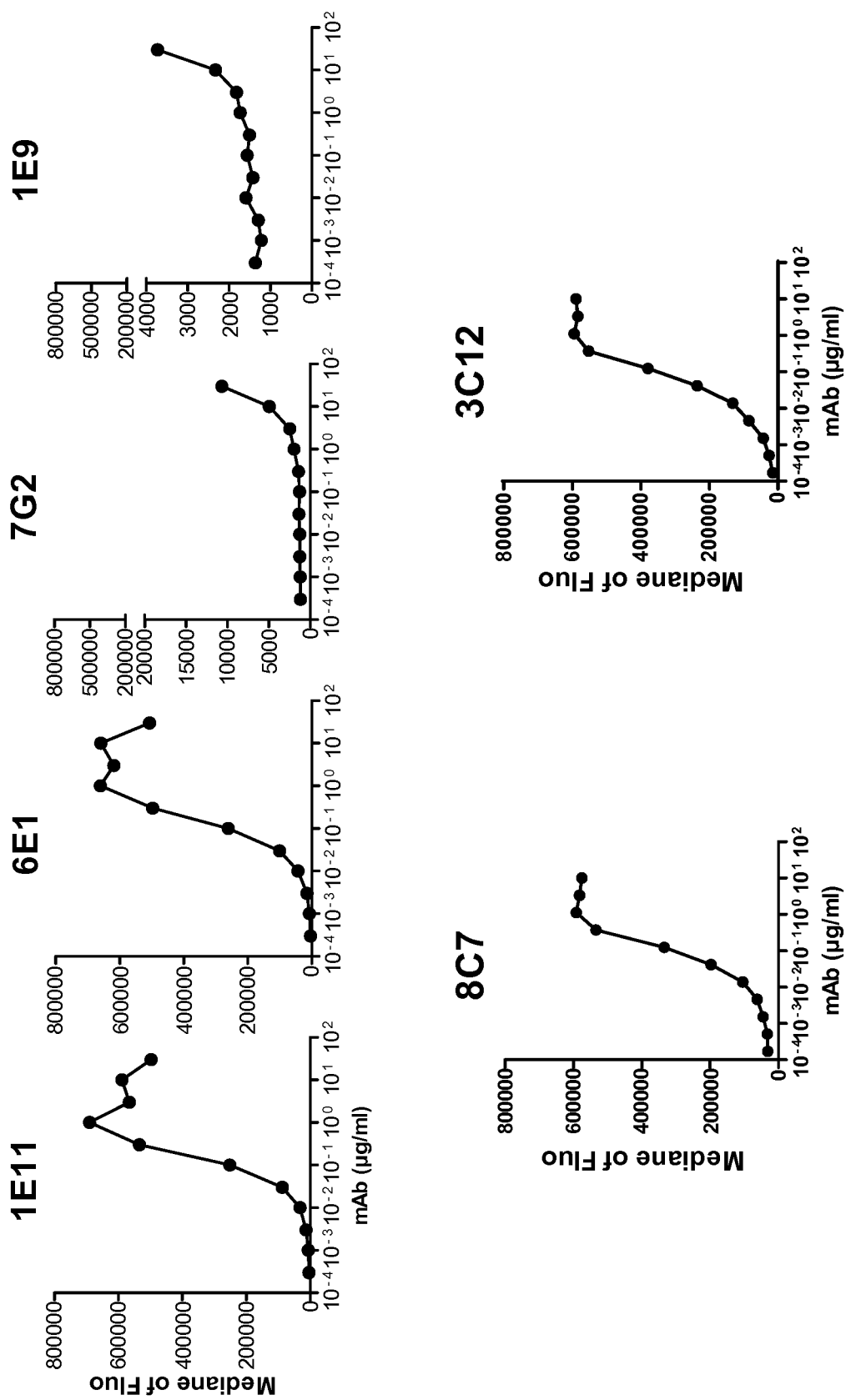
FIG. 4 shows results of titration of antibodies by flow cytometry on human MDA-MB-231 breast adenocarcinoma cells that endogenously expresses CD73. 11E1, 8C7, 3C12 and 6E1, but not 7G2 or 1E9, bind to MDA-MB-231 cells with excellent affinity.

Experiments were repeated using human MDA-MB-231 breast adenocarcinoma cells that endogenously expresses CD73. Again mAbs 11E1, 8C7, 3C12 and 6E1 bind with excellent affinity while mAbs 7G2 and 1E9 show poor binding. Results on MDA-MB-231 cells are shown in FIG. 4.

It is possible that 7G2 and 1E9 bind to an epitope on CD73 that is presented differently in recombinant CD73 and CD73 on the surface of the CD73-expressing cells, including notably human tumor cells that endogenously expresses CD73, resulting in mAbs that bind well to recombinant CD73 (e.g. used in immunization) but not to cell surface CD73. The epitopes bound by 11E1, 8C7, 3C12 and 6E1 on the other hand, remains present on cell surface CD73.

Experiments were then repeated using human MDA-MB-231 breast adenocarcinoma cells that endogenously expresses CD73. Cells were pre-incubated at 37° C. for 30 minutes in the presence or not of 200 µM adenosine 5'-(α, β-methylene)diphosphate (APCP), followed by addition of antibodies. APCP is an analog of ADP and binds irreversibly to the active site of CD73. When bound by APCP, CD73 changes conformation from an "open" conformation to a "closed" conformation. mAbs 11E1, 8C7, 3C12 and 6E1 bound MDA-MB-231 cells with good affinity both in the presence and absence of APCP. In the presence of APCP, the EC50 was similar to that observed in the absence of APCP. The plateau for maximal binding of 11E1, 8C7, 3C12 and 6E1 was higher in the absence of APCP than in the presence of APCP, while the inverse was true for AD2. EC50 figures are shown in the table below.

| Antibody | EC50 (ng/ml) | |
| --- | --- | --- |
|  | Medium | APCP |
| 11E1 | 61.11 | 37.5 |
| 3C12 | 57.22 | 43.11 |
| 6E1 | 58.39 | 39.48 |
| 8C7 | 90.29 | 143.4 |
| AD2 | 62.89 | 95.92 |

Example 5: Cellular CD73 Activity Blockade

Part A: Blockade in MDA-MB-231 Tumor Cells

The ability of anti-CD73 antibodies to neutralize the 5'-ectonucletidase enzymatic activity of cell-surface expressed CD73 was evaluated. The MDA-MB-231 tumor cell line was used a model tumor cell line that expresses CD73.

All reagents used in the experiment detailed below were diluted in TBS pH7.5 (Tris 20 mM pH7.5, NaCl 150 mM). MDA-MB-231 cell line is recovered in PBS-EDTA and washed twice in TBS pH7.5. 0.5 to $1 \times 10^5$ cells were plated in flat-bottom 96 well plates in presence of dose-range of anti-CD73 antibodies and incubated for 2 hours at 4° C. 200 mM AMP was added to the cells for a 30 minutes incubation period at 4° C. (to avoid CD73 down-modulation). Plates were then centrifuged and 50 µl supernatant are transferred in flat bottom 96 well culture plate. Free phosphate produced by the hydrolysis of AMP into adenosine was quantified using the Malachite Green Phosphate Detection Kit (R&D Systems) and following TDS provided by the manufacturer. Phosphate concentration vs. anti-CD73 Ab concentration was plotted in graphs and EC50 is calculated using Graph-Pad Prism software.

Figure 5:
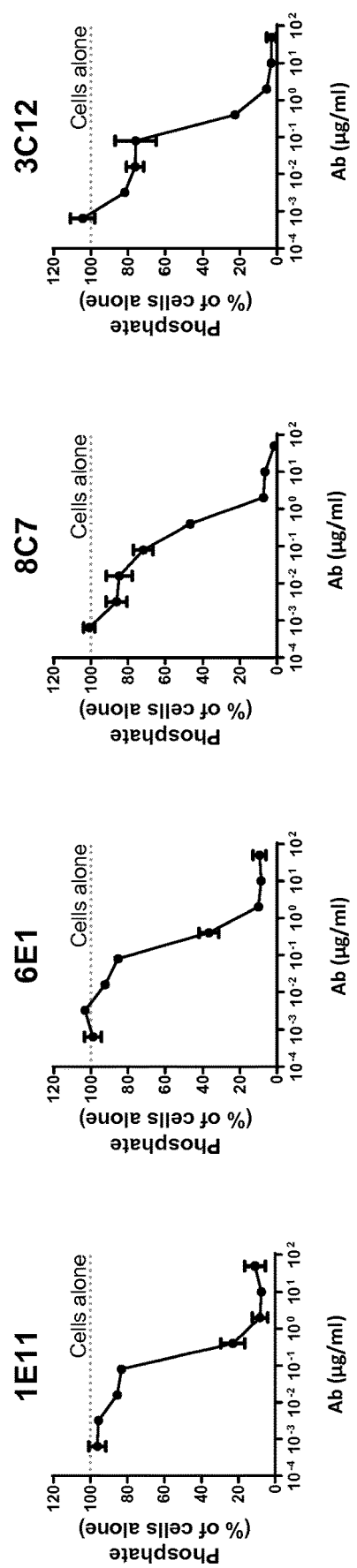
FIG. 5 shows antibodies 11E1, 8C7, 3C12 and 6E1 neutralize the enzymatic activity of cellular CD73.

Results are shown in FIG. 5. Antibodies 11E1, 8C7, 3C12 and 6E1 neutralized the enzymatic activity of cellular CD73, with $EC_{50}$ values shown in the table below.

| Ab | EC50 (µg/ml) |
| --- | --- |
| 1E11 | 0.195 |
| 6E1 | 0.209 |
| 8C7 | 0.319 |
| 3C12 | 0.210 |

Each antibody achieved a decrease of more than 75%, or more than 80% of the enzymatic activity. Antibody 7G2, consistent with poor binding to cellular CD73 (see Example 4), did not neutralize enzymatic activity of cellular CD73. Antibody 7G2, consistent with its limited ability to bind cell surface CD73, did not neutralize CD73 enzymatic activity at any concentration, and only elicited a slight partial inhibition at the highest concentrations tested.

In each case, for the non-internalizing antibodies 1E11, 6E1, 8C7 and 3C12, the $EC_{50}$ values required for neutralization of the enzymatic activity of cellular CD73 in MDA-MB-231 cell were several-fold higher than the $EC_{50}$ values required for binding to cell surface CD73 in MDA-MB-231 cells.

Part B: Blockade in MDA-MB-231, H292 and A375 tumor cells

The ability of anti-CD73 antibodies to neutralize the 5'-ectonucletidase enzymatic activity of cell-surface expressed CD73 was evaluated using the same assay as above, this time in multiple experiments using three tumor cell lines that express CD73 lines in parallel: the MDA-MB-231 breast adenocarcinoma tumor cell line, the H292 lung cancer cell line (see, e.g., ATCC reference CRL-1848), and the A375 melanoma cancer cell line (see, e.g., ATCC reference CRL-1619). The effective concentrations required for neutralization (ECs, e.g. EC50, EC70, EC100) shown in the table below were calculated as a mean from repeated experiments on the three different CD73-expressing cell types.

| Antibody | 1E11 | 3C12 | 6E1 | 8C7 |
| --- | --- | --- | --- | --- |
| N = | 8 | 8 | 8 | 2 |
| $EC_{50}$ (µg/ml) | 0.10 | 0.14 | 0.13 | 0.21 |
| $EC_{70}$ (µg/ml) | 0.15 | 0.18 | 0.19 | 0.46 |
| $EC_{100}$ (µg/ml) | 0.52 | 0.30 | 0.68 | 0.72 |

Example 6: Flow Cytometry Competition Study

A human CD73-expressing recombinant host cell line was used to evaluate competition between our candidates and other commercial anti-CD73 antibodies. $10^5$ cells resuspended in staining buffer were distributed into round bottom 96W-microplates. A fixed dose of test antibodies (1 µg/ml) is added to the cells in presence or not of a dose-range of reference mouse anti-human CD73 antibodies. Cells were incubated for 45 minutes at 4° C. then washed three times as described above. PE-coupled or goat anti-human IgG Fc fragment secondary antibodies (Beckman Coulter) diluted in staining buffer were added to the cells and plates are incubated for 30 additional minutes at 4° C. Cells were washed three times and analyzed on an Accury C6 flow cytometer equipped with an HTFC plate reader.

Median of fluorescence vs. antibodies concentration was plotted. To study epitopes of CD73-neutralizing antibodies, the ability of known antibodies to block the binding of new antibodies to the cell membrane CD73 was evaluated as competition between antibodies. Reference antibody 7G2, shown in Example 2 to have the ability to neutralize CD73 without dependence upon induction of oligomerization, but which does not bind or neutralize CD73 in cellular assays, was tested with new antibody candidates. Neither antibodies 11E1, 8C7, 3C12 nor 6E1 competed with 7G2 for binding to CD73, showing that 7G2 binds to an area on CD73 distinct from that of the new antibodies.

Example 7: CD73 Down-Modulation

Human MDA-MB-231 breast adenocarcinoma cell line that endogenously expresses CD73 was used to evaluate the capacity of anti-CD73 antibodies to down regulate CD73 expression. $10^5$ cells resuspended in staining buffer were distributed into flat bottom 96W-microplates. 10 µg/ml of anti-CD73 antibodies were added to the cells and plates are incubated at 4° C. or 37° C. for a time course. At T=10 min, 30 min, 1h, 2h, 3h and 4h, cells were recovered using PSB/2 mM EDTA, washed three times in staining buffer as prior described and incubated at 4° C. until end of the time course. 10 µg/ml of a AlexaFLuor 647-coupled non-competing anti-CD73 antibody were added to the cells and plates are incubated for 30 min at 4° C. Cells were washed three times and analyzed on an Accury C6 flow cytometer equipped with an HTFC plate reader.

Percentage of expression vs. incubation time is plotted on graphs.

Figure 6:
FIG. 6 shows the ability of various antibodies to cause down-modulation of CD73 expression on cells. Each of AD2, 7G2 and 1E9 caused down-modulation of CD73, however none of antibodies 11E1, 8C7, 3C12, or 6E1 caused a decrease in cell surface CD73.
Figure 6:
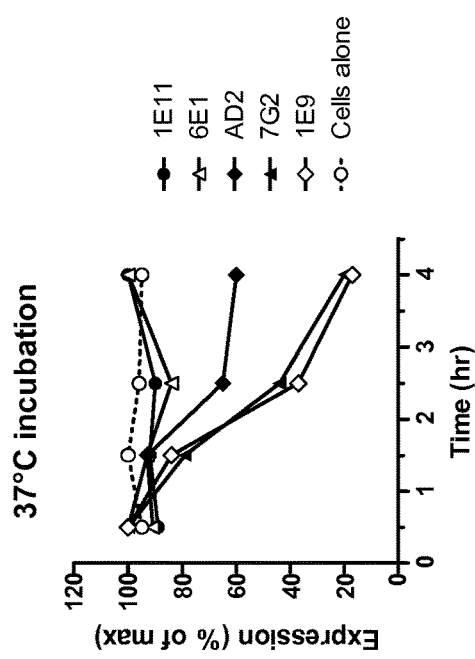
Figure 6:
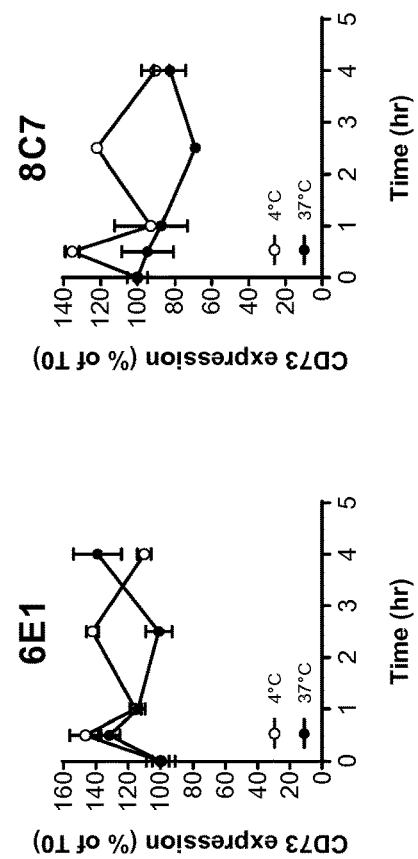
Figure 6:
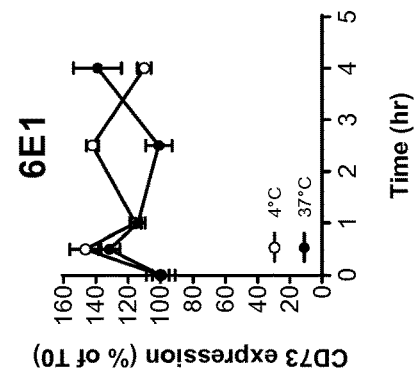
Figure 6:
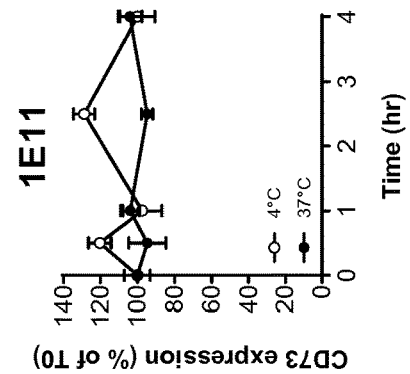

Antibodies were evaluated for their ability to cause down-modulation of CD73 expression on cells, and compared to reference mAbs AD2, 7G2 and 1E9. Each of AD2, 7G2 and 1E9 caused down-modulation of CD73, suggesting that these mAbs may be causing clustering and internalization of CD73. AD2 caused a decrease of well over 20% while 7G2 and 1E9 each caused a decrease in over 50% of receptor at the cell surface. Neither antibody 11E1, 8C7, 3C12 or 6E1 caused a decrease in CD73 at the cell surface. Results are shown in FIG. 6.

Example 8: Epitope Mapping

In order to define the epitopes of anti-CD73 antibodies, we designed CD73 mutants defined by substitutions of amino acids exposed at the molecular surface over the surface of CD73. Mutants were transfected in Hek-293T cells, as shown in the table below. The targeted amino acid mutations in the table 1 below are shown using numbering of SEQ ID NO: 1.

TABLE 1

| Mutant | Substitutions | | | | | | |
|---|---|---|---|---|---|---|---|
| 1 | E46A | S49A | V52A | N53A | R56L | M58V | |
| 2 | Q70S | R73A | A74E | A107I | R109G | | |
| 3 | A99S | E129A | K133A | E134N | A135S | | |
| 4 | K145A | K147A | S152H | S155A | Y161S | E203A | K206A |
| 5 | P165S | D168G | N211A | E296A | R297A | | |
| 6 | K179A | E196A | I197S | T198A | E224A | M225S | Q231A |
| 7 | K262A | F265S | I266A | K274Q | I292A | S302A | H304Y |
| 8 | P318A | S319A | K321A | N325A | K326Q | | |
| 9 | Y345A | D347A | S349A | S352A | D399A | R401A | |
| 10 | D460A | L461S | S462A | R463A | G466W | D467N | K471A |
| 11 | D473A | K478A | R480A | S483A | D485A | K488E | E491K |
| 12 | N503A | Q509A | K512S | D513A | | | |
| 13 | R354A | R395A | Q444A | T446A | | | |
| 14 | D332A | N333A | T336A | E409A | | | |
| 15 | H375A | E378A | R517A | S520A | D522A | | |

Generation of Mutants

Figure 7:
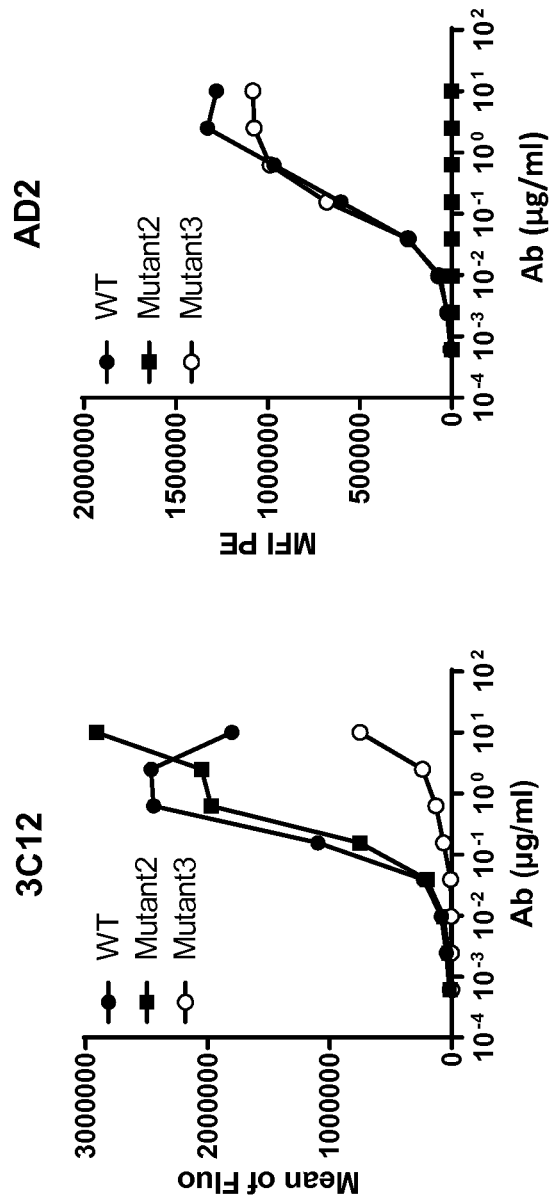
FIG. 7 shows titration of antibodies by flow cytometry on cell expressing mutants of human CD73. Antibody 3C12 binds to wild type CD73 and mutant 2 but not to mutant 3, while antibody AD2 binds to wild type CD73 and mutant 3, but not to mutant 2.

CD73 mutants are generated by PCR. The sequences amplified are run on agarose gel and purified using the Macherey Nagel PCR Clean-Up Gel Extraction kit (reference 740609). The purified PCR products generated for each mutant are then ligated into an expression vector, with the ClonTech InFusion system. The vectors containing the mutated sequences are prepared as Miniprep and sequenced. After sequencing, the vectors containing the mutated sequences are prepared as Midiprep using the Promega PureYield™ Plasmid Midiprep System. HEK293T cells are grown in DMEM medium (Invitrogen), transfected with vectors using Invitrogen's Lipofectamine 2000 and incubated at 37° C. in a CO2 incubator for 24 hours prior to testing for transgene expression Flow Cytometry Analysis of Anti-CD73 Binding to the HEK293T Transfected Cells Anti-CD73 antibodies are tested for their binding to each mutant by flow cytometry. A first experiment is performed to determine antibodies that lose their binding to one or several mutants at one concentration. To confirm a loss of binding, titration of antibodies is done on antibodies for which binding seemed to be affected by the CD73 mutations (1-0.1-0.01-0.001 µg/ml). Antibodies 11E1, 8C7, 3C12 or 6E1 lost binding to mutant 3 of CD73, but not to any other mutant. Mutant 3 contains amino acid substitutions at residues A99, E129, K133, E134, and A135, indicating that one or more, or all of, the residues of the mutant are important to the core epitope of these antibodies. Antibody AD2 that causes clustering and internalization of CD73 did not lose binding to mutant 3; AD2 instead lost binding to mutant 2 having substitutions at residues Q70, R73, A74, A107 and R109. Exemplary results for antibody 3C12 and AD2 are shown in FIG. 7. Antibody 7G2 lost binding to mutants 5, 6 and 7 (but not mutants 2 or 3).

Figure 8A:
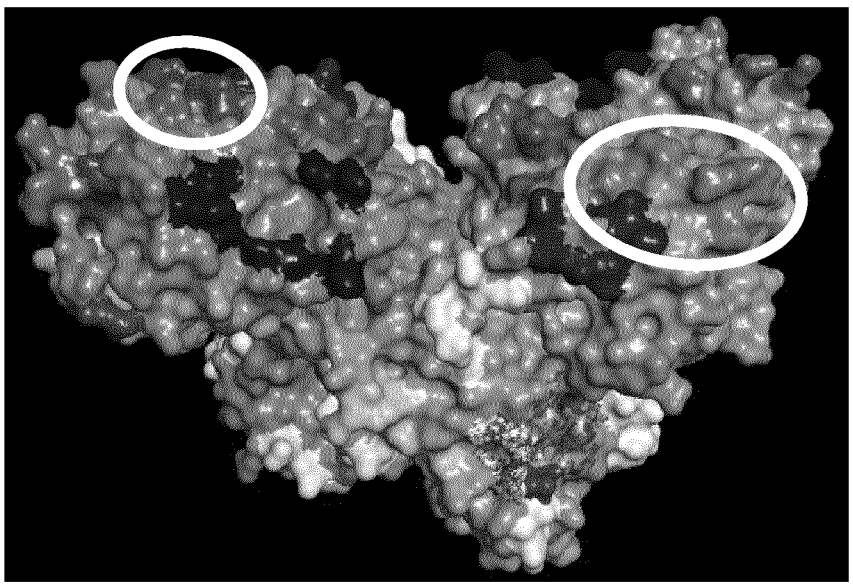
FIG. 8A shows the molecular structure of the CD73 dimer, with amino acids mutated in mutant 2 (loss of binding by AD2) indicated (white circles) in both "open" or "closed" configurations.
Figure 8A:
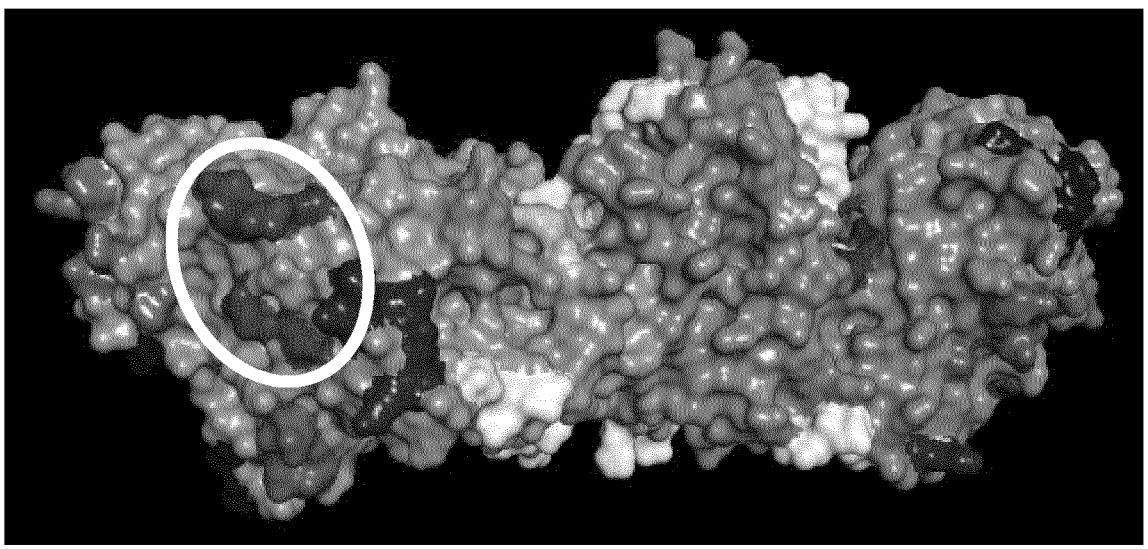
Figure 8B:
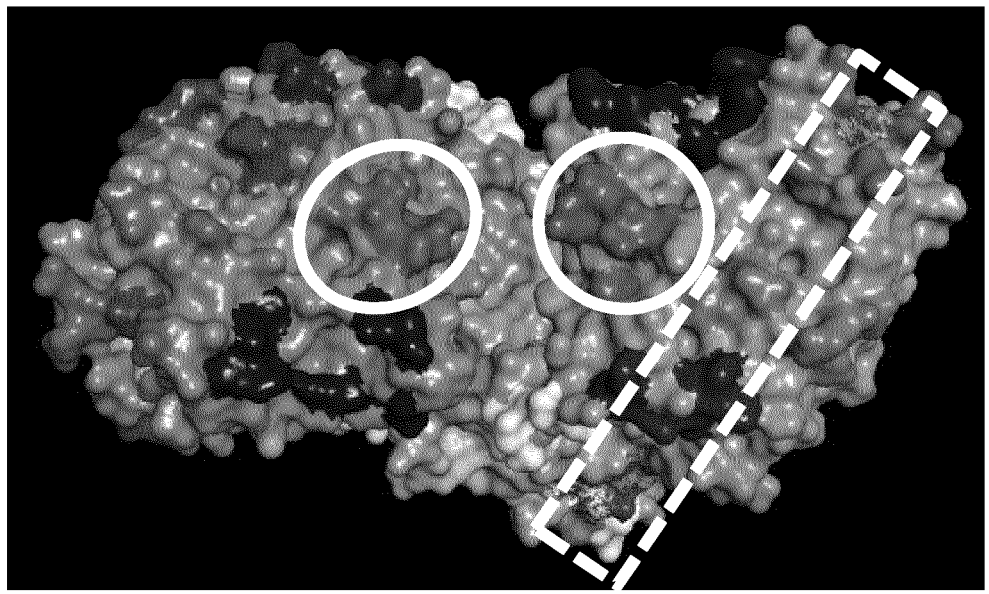
FIG. 8B shows the molecular structure of the CD73 dimer, with amino acids mutated in mutant 3 (loss of binding by 11E1, 8C7, 3C12 or 6E1) indicated in both "open" or "closed" configurations. The active site is indicated by the box (dashed lines).
Figure 8B:
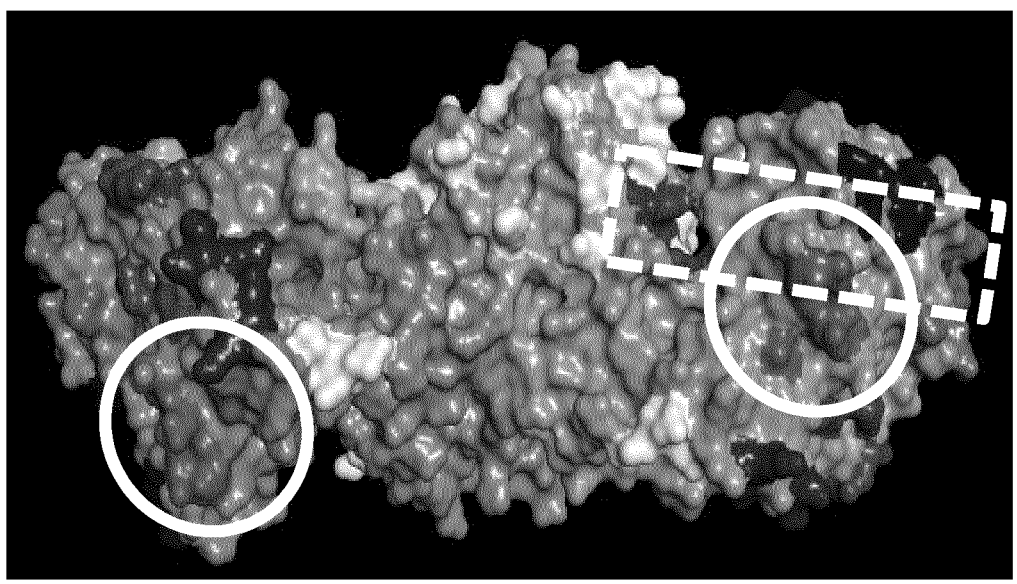

When bound by active site ligands as illustrated by the irreversibly ADP analog binder APCP, CD73 changes conformation from an "open" conformation to a "closed" conformation. As shown in Example 4, mAbs 11E1, 8C7, 3C12 and 6E1 bound cellular CD73 both in the presence and absence of APCP, indicating that the epitope of these antibodies remains present on CD73 when the active site is occupied. FIG. 8A shows the molecular structure of the CD73 dimer, with amino acids mutated in mutant 2 (loss of binding by AD2) indicated (white circles) in both "open" or "closed" configurations. FIG. 8B shows the molecular structure of the CD73 dimer, with amino acids mutated in mutant 3 (loss of binding by 11E1, 8C7, 3C12 or 6E1) indicated in both "open" or "closed" configurations. The active site is indicated by the box (dashed lines). Interestingly, it can be seen from FIG. 8B that when the CD73 assumes a dimeric form, the amino acids mutated in mutant 3 are on a common face of the CD73 dimer, e.g., on or about on a plane (other epitopes of other mutants are not). Finally, from a comparison of the amino acids within mutant 3 one can see that these residues are relatively distant from the enzymatic active site (indicated in FIG. 8B), consistent with a mode of action that involves allosteric inhibition of CD73.

Example 9: CD73 Binding Affinity by Surface Plasmon Resonance (SPR)

Biacore T100 General Procedure and Reagents

SPR measurements were performed on a Biacore T100 apparatus (Biacore GE Healthcare) at 25° C. In all Biacore experiments HBS-EP+(Biacore GE Healthcare) and NaOH 10 mM served as running buffer and regeneration buffer respectively. Sensorgrams were analyzed with Biacore T100 Evaluation software. Protein-A was purchase from (GE Healthcare). Human soluble dimeric CD73 proteins were cloned, produced and purified at Innate Pharma.

Immobilization of Protein-A

Protein-A proteins were immobilized covalently to carboxyl groups in the dextran layer on a Sensor Chip CM5. The chip surface was activated with EDC/NHS (N-ethyl-N'-(3-dimethylaminopropyl) carbodiimide hydrochloride and N-hydroxysuccinimide (Biacore GE Healthcare). Protein-A was diluted to 10 μg/ml in coupling buffer (10 mM acetate, pH 5.6) and injected until the appropriate immobilization level was reached (i.e. 2000 RU). Deactivation of the remaining activated groups was performed using 100 mM ethanolamine pH 8 (Biacore GE Healthcare).

Affinity Study

Affinity study was carried out according to a standard Capture-Kinetic protocol recommended by the manufacturer (Biacore GE Healthcare kinetic wizard). Serial dilutions of human recombinant soluble dimeric CD73 proteins, ranging from 1.23 to 300 nM were sequentially injected over the captured anti-CD73 antibodies and allowed to dissociate for 10 min before regeneration. The entire sensorgram sets were fitted using the 1:1 kinetic binding model. Bivalent affinities and kinetic association and dissociation rate constants are shown below in Table 2 below.

TABLE 2

| CD73 Ab | KD (nM) |
|---|---|
| 1E11 | 0.822 |
| 3C12 | 0.682 |
| 6E1 | 0.819 |

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar references are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment herein using terms such as "comprising", "having," "including," or "containing" with reference to an element or elements is intended to provide support for a similar aspect or embodiment herein that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. An isolated antibody or antibody fragment that specifically binds a human CD73 polypeptide at the surface of a cell and that is capable of neutralizing the 5'-ectonucleotidase activity thereof, selected from the group consisting of:
   (a) monoclonal antibody or antibody fragment comprising (i) a heavy chain variable region comprising CDR 1, 2 and 3 of the heavy chain variable region of SEQ ID NO: 3 and (ii) a light chain variable region comprising CDR 1, 2 and 3 of the light chain variable region of SEQ ID NO: 4;
   (b) monoclonal antibody or antibody fragment comprising (i) a heavy chain variable region comprising CDR 1, 2 and 3 of the heavy chain variable region of SEQ ID NO: 3 and (ii) a light chain variable region comprising CDR 1, 2 and 3 of the light chain variable region of SEQ ID NO: 21;
   (c) monoclonal antibody or antibody fragment comprising (i) a heavy chain variable region comprising CDR 1, 2 and 3 of the heavy chain variable region of SEQ ID NO: 28 and (ii) a light chain variable region comprising CDR 1, 2 and 3 of the light chain variable region of SEQ ID NO: 29; and
   (d) monoclonal antibody or antibody fragment comprising (i) a heavy chain variable region comprising CDR 1, 2 and 3 of the heavy chain variable region of SEQ ID NO: 36 and (ii) a light chain variable region comprising CDR 1, 2 and 3 of the light chain variable region of SEQ ID NO: 37.

2. The isolated antibody of claim 1, wherein the antibody is a human IgG4 antibody or an antibody having a human Fc domain that is modified to reduce binding between the Fc domain and an Fcγ receptor.

3. The isolated antibody of claim 1, wherein the antibody is an IgG1 and comprises one, two or three substitutions at residues 234, 235 and 331 or at 234, 235 and 322 (EU numbering).

4. A pharmaceutical composition comprising an antibody or antibody fragment according to claim 1, and a pharmaceutically acceptable carrier.

5. The isolated antibody or antibody fragment of claim 1, said monoclonal antibody or antibody fragment comprising (i) a heavy chain variable region comprising CDR 1, 2 and 3 of the heavy chain variable region of SEQ ID NO: 3 and (ii) a light chain variable region comprising CDR 1, 2 and 3 of the light chain variable region of SEQ ID NO: 4.

6. The isolated antibody or antibody fragment of claim 1, said monoclonal antibody comprising (i) a heavy chain variable region comprising CDR 1, 2 and 3 of the heavy chain variable region of SEQ ID NO: 3 and (ii) a light chain variable region comprising CDR 1, 2 and 3 of the light chain variable region of SEQ ID NO: 21.

7. The isolated antibody or antibody fragment of claim 1, said monoclonal antibody comprising (i) a heavy chain variable region comprising CDR 1, 2 and 3 of the heavy chain variable region of SEQ ID NO: 28 and (ii) a light chain variable region comprising CDR 1, 2 and 3 of the light chain variable region of SEQ ID NO: 29.

8. The isolated antibody or antibody fragment of claim 1, said monoclonal antibody comprising (i) a heavy chain variable region comprising CDR 1, 2 and 3 of the heavy chain variable region of SEQ ID NO: 36 and (ii) a light chain variable region comprising CDR 1, 2 and 3 of the light chain variable region of SEQ ID NO: 37.

9. The isolated antibody or antibody fragment of claim 1, said antibody fragment comprising (i) a heavy chain variable region comprising CDR 1, 2 and 3 of the heavy chain variable region of SEQ ID NO: 3 and (ii) a light chain variable region comprising CDR 1, 2 and 3 of the light chain variable region of SEQ ID NO: 4.

10. The isolated antibody or antibody fragment of claim 1, said antibody fragment comprising (i) a heavy chain variable region comprising CDR 1, 2 and 3 of the heavy chain variable region of SEQ ID NO: 3 and (ii) a light chain variable region comprising CDR 1, 2 and 3 of the light chain variable region of SEQ ID NO: 21.

11. The isolated antibody or antibody fragment of claim 1, said antibody fragment comprising (i) a heavy chain variable region comprising CDR 1, 2 and 3 of the heavy chain variable region of SEQ ID NO: 28 and (ii) a light chain variable region comprising CDR 1, 2 and 3 of the light chain variable region of SEQ ID NO: 29.

12. The isolated antibody or antibody fragment of claim 1, said antibody fragment comprising (i) a heavy chain variable region comprising CDR 1, 2 and 3 of the heavy chain variable region of SEQ ID NO: 36 and (ii) a light chain variable region comprising CDR 1, 2 and 3 of the light chain variable region of SEQ ID NO: 37.

* * * * *

UNITED STATES PATENT AND TRADEMARK OFFICE
CERTIFICATE OF CORRECTION

PATENT NO. : 10,766,966 B2  
APPLICATION NO. : 15/517991  
DATED : September 8, 2020  
INVENTOR(S) : Ivan Perrot, Carine Paturel and Laurent Gauthier Page 1 of 1

It is certified that error appears in the above-identified patent and that said Letters Patent is hereby corrected as shown below:

In the Specification

Column 5,  
Line 63, "ECs," should read --$EC_{50}$,--.

Column 8,  
Line 41, "ECs," should read --$EC_{50}$,--.

Column 10,  
Line 26, "ECs," should read --$EC_{50}$,--.

Column 36,  
Line 65, "N (Asp)." should read --N (Asn).--.

Column 39, Table A,  
mab 1E11, LCDR1 Kabat SEQ 14, "KASO5VINDVA" should read --KASQSVTNDVA--.  
mab 1E11, LCDR1 Chotia SEQ 15, "SQSVIND" should read --SQSVTND--.  
mab 6E1, LCDR1 Kabat SEQ 14, "KASQ5VINDVA" should read --KASQSVTNDVA--.  
mab 6E1, LCDR1 Chotia SEQ 15, "SQSVIND" should read --SQSVTND--.

Signed and Sealed this  
Twenty-sixth Day of January, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 46

<210> SEQ ID NO 1
<211> LENGTH: 574
<212> TYPE: PRT
<213> ORGANISM: Homo sapiens

<400> SEQUENCE: 1

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140
```

```
Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Asn Leu Arg His Thr Asp Glu Met Phe Trp Asn His Val
    370                 375                 380

Ser Met Cys Ile Leu Asn Gly Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
```

<210> SEQ ID NO 2
<211> LENGTH: 553
<212> TYPE: PRT
<213> ORGANISM: Homo sapiens

<400> SEQUENCE: 2

```
Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
                35                  40                  45

Ser Lys Cys Val Asn Ala Ser Arg Cys Met Gly Gly Val Ala Arg Leu
        50                  55                  60

Phe Thr Lys Val Gln Gln Ile Arg Arg Ala Glu Pro Asn Val Leu Leu
65              70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
                115                 120                 125

Glu Pro Leu Leu Lys Glu Ala Lys Phe Pro Ile Leu Ser Ala Asn Ile
        130                 135                 140

Lys Ala Lys Gly Pro Leu Ala Ser Gln Ile Ser Gly Leu Tyr Leu Pro
145             150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
                180                 185                 190

Phe Glu Asp Glu Ile Thr Ala Leu Gln Pro Glu Val Asp Lys Leu Lys
                195                 200                 205

Thr Leu Asn Val Asn Lys Ile Ile Ala Leu Gly His Ser Gly Phe Glu
        210                 215                 220

Met Asp Lys Leu Ile Ala Gln Lys Val Arg Gly Val Asp Val Val Val
225             230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
                260                 265                 270

Arg Lys Val Pro Val Val Gln Ala Tyr Ala Phe Gly Lys Tyr Leu Gly
                275                 280                 285

Tyr Leu Lys Ile Glu Phe Asp Glu Arg Gly Asn Val Ile Ser Ser His
        290                 295                 300

Gly Asn Pro Ile Leu Leu Asn Ser Ser Ile Pro Glu Asp Pro Ser Ile
305             310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
                340                 345                 350

Cys Arg Phe Arg Glu Cys Asn Met Gly Asn Leu Ile Cys Asp Ala Met
                355                 360                 365
```

```
Ile Asn Asn Asn Leu Arg His Thr Asp Glu Met Phe Trp Asn His Val
370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
            435                 440                 445

Phe Leu Gln Val Gly Ile His Val Val Tyr Asp Leu Ser Arg Lys
450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
                500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
530                 535                 540

Arg Ile Lys His His His His His His
545                 550

<210> SEQ ID NO 3
<211> LENGTH: 120
<212> TYPE: PRT
<213> ORGANISM: mus musculus

<400> SEQUENCE: 3

Glu Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
                20                  25                  30

Asn Met Tyr Trp Val Lys Gln Ser His Gly Lys Ser Leu Glu Trp Ile
            35                  40                  45

Gly Tyr Ile Asp Pro Tyr Asn Gly Gly Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met His Leu Asn Ser Leu Thr Ser Glu Asp Ser Ala Val Tyr Tyr Cys
                85                  90                  95

Ala Arg Gly Tyr Gly Asn Tyr Lys Ala Trp Phe Ala Tyr Trp Gly Gln
                100                 105                 110

Gly Thr Leu Val Thr Val Ser Ala
            115                 120

<210> SEQ ID NO 4
<211> LENGTH: 106
<212> TYPE: PRT
<213> ORGANISM: Mus musculus

<400> SEQUENCE: 4

Asp Ala Val Met Thr Gln Thr Pro Lys Phe Leu Leu Val Ser Ala Gly
1               5                   10                  15
```

```
Asp Arg Val Thr Ile Thr Cys Lys Ala Ser Gln Ser Val Thr Asn Asp
                20                  25                  30

Val Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
        50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Leu Thr
                85                  90                  95

Phe Gly Ala Gly Thr Lys Leu Glu Leu Lys
            100                 105

<210> SEQ ID NO 5
<211> LENGTH: 5
<212> TYPE: PRT
<213> ORGANISM: Mus musculus

<400> SEQUENCE: 5

Ser Tyr Asn Met Tyr
1               5

<210> SEQ ID NO 6
<211> LENGTH: 7
<212> TYPE: PRT
<213> ORGANISM: Mus musculus

<400> SEQUENCE: 6

Gly Tyr Ala Phe Thr Ser Tyr
1               5

<210> SEQ ID NO 7
<211> LENGTH: 8
<212> TYPE: PRT
<213> ORGANISM: Mus musculus

<400> SEQUENCE: 7

Gly Tyr Ala Phe Thr Ser Tyr Asn
1               5

<210> SEQ ID NO 8
<211> LENGTH: 17
<212> TYPE: PRT
<213> ORGANISM: Mus musculus

<400> SEQUENCE: 8

Tyr Ile Asp Pro Tyr Asn Gly Gly Thr Ser Tyr Asn Gln Lys Phe Lys
1               5                   10                  15

Gly

<210> SEQ ID NO 9
<211> LENGTH: 4
<212> TYPE: PRT
<213> ORGANISM: Mus musculus

<400> SEQUENCE: 9

Pro Tyr Asn Gly
1

<210> SEQ ID NO 10
<211> LENGTH: 8
<212> TYPE: PRT
```

-continued

<213> ORGANISM: Mus musculus

<400> SEQUENCE: 10

Ile Asp Pro Tyr Asn Gly Gly Thr
1               5

<210> SEQ ID NO 11
<211> LENGTH: 11
<212> TYPE: PRT
<213> ORGANISM: Mus musculus

<400> SEQUENCE: 11

Gly Tyr Gly Asn Tyr Lys Ala Trp Phe Ala Tyr
1               5                   10

<210> SEQ ID NO 12
<211> LENGTH: 9
<212> TYPE: PRT
<213> ORGANISM: Mus musculus

<400> SEQUENCE: 12

Tyr Gly Asn Tyr Lys Ala Trp Phe Ala
1               5

<210> SEQ ID NO 13
<211> LENGTH: 13
<212> TYPE: PRT
<213> ORGANISM: Mus musculus

<400> SEQUENCE: 13

Ala Arg Gly Tyr Gly Asn Tyr Lys Ala Trp Phe Ala Tyr
1               5                   10

<210> SEQ ID NO 14
<211> LENGTH: 11
<212> TYPE: PRT
<213> ORGANISM: Mus musculus

<400> SEQUENCE: 14

Lys Ala Ser Gln Ser Val Thr Asn Asp Val Ala
1               5                   10

<210> SEQ ID NO 15
<211> LENGTH: 7
<212> TYPE: PRT
<213> ORGANISM: Mus musculus

<400> SEQUENCE: 15

Ser Gln Ser Val Thr Asn Asp
1               5

<210> SEQ ID NO 16
<211> LENGTH: 6
<212> TYPE: PRT
<213> ORGANISM: Mus musculus

<400> SEQUENCE: 16

Gln Ser Val Thr Asn Asp
1               5

<210> SEQ ID NO 17
<211> LENGTH: 7
<212> TYPE: PRT
<213> ORGANISM: Mus musculus

```
<400> SEQUENCE: 17

Tyr Ala Ser Asn Arg Tyr Thr
1               5

<210> SEQ ID NO 18
<211> LENGTH: 3
<212> TYPE: PRT
<213> ORGANISM: Mus musculus

<400> SEQUENCE: 18

Tyr Ala Ser
1

<210> SEQ ID NO 19
<211> LENGTH: 8
<212> TYPE: PRT
<213> ORGANISM: Mus musculus

<400> SEQUENCE: 19

Gln Gln Asp Tyr Ser Ser Leu Thr
1               5

<210> SEQ ID NO 20
<211> LENGTH: 5
<212> TYPE: PRT
<213> ORGANISM: Mus musculus

<400> SEQUENCE: 20

Asp Tyr Ser Ser Leu
1               5

<210> SEQ ID NO 21
<211> LENGTH: 120
<212> TYPE: PRT
<213> ORGANISM: Mus musculus

<400> SEQUENCE: 21

Glu Phe Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Thr Ser Tyr
            20                  25                  30

Asn Met Tyr Trp Val Lys Gln Ser His Gly Lys Arg Leu Glu Trp Ile
        35                  40                  45

Gly Tyr Ile Asp Pro Tyr Asn Gly Gly Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met His Leu Asn Asn Leu Thr Ser Glu Asp Ser Ala Val Tyr Tyr Cys
                85                  90                  95

Ala Arg Gly Tyr Asn Asn Tyr Lys Ala Trp Phe Ala Tyr Trp Gly Gln
            100                 105                 110

Gly Thr Leu Val Thr Val Ser Ala
        115                 120

<210> SEQ ID NO 22
<211> LENGTH: 106
<212> TYPE: PRT
<213> ORGANISM: Mus musculus

<400> SEQUENCE: 22

Ser Ile Val Met Thr Gln Thr Pro Lys Phe Leu Leu Val Ser Ala Gly
```

```
                1               5                  10                  15
            Asp Arg Val Thr Ile Thr Cys Lys Ala Ser Gln Ser Val Thr Asn Asp
                            20                  25                  30

Val Ala Trp Tyr Gln Lys Pro Gly Gln Ser Pro Lys Leu Leu Ile
                        35                  40                  45

Tyr Tyr Ala Ser Asn Arg Tyr Thr Gly Val Pro Asp Arg Phe Thr Gly
                    50                  55                  60

Ser Gly Tyr Gly Thr Asp Phe Thr Phe Thr Ile Ser Thr Met Gln Ala
            65                  70                  75                  80

Glu Asp Leu Ala Val Tyr Phe Cys Gln Gln Asp Tyr Ser Ser Leu Thr
                            85                  90                  95

Phe Gly Ala Gly Thr Lys Leu Glu Leu Lys
                        100                 105
```

<210> SEQ ID NO 23
<211> LENGTH: 17
<212> TYPE: PRT
<213> ORGANISM: Mus musculus

<400> SEQUENCE: 23

```
Tyr Ile Asp Pro Tyr Asn Gly Gly Ser Ser Tyr Asn Gln Lys Phe Lys
1               5                   10                  15

Gly
```

<210> SEQ ID NO 24
<211> LENGTH: 8
<212> TYPE: PRT
<213> ORGANISM: Mus musculus

<400> SEQUENCE: 24

```
Ile Asp Pro Tyr Asn Gly Gly Ser
1               5
```

<210> SEQ ID NO 25
<211> LENGTH: 11
<212> TYPE: PRT
<213> ORGANISM: Mus musculus

<400> SEQUENCE: 25

```
Gly Tyr Asn Asn Tyr Lys Ala Trp Phe Ala Tyr
1               5                   10
```

<210> SEQ ID NO 26
<211> LENGTH: 9
<212> TYPE: PRT
<213> ORGANISM: Mus musculus

<400> SEQUENCE: 26

```
Tyr Asn Asn Tyr Lys Ala Trp Phe Ala
1               5
```

<210> SEQ ID NO 27
<211> LENGTH: 13
<212> TYPE: PRT
<213> ORGANISM: Mus musculus

<400> SEQUENCE: 27

```
Ala Arg Gly Tyr Asn Asn Tyr Lys Ala Trp Phe Ala Tyr
1               5                   10
```

<210> SEQ ID NO 28

```
<211> LENGTH: 126
<212> TYPE: PRT
<213> ORGANISM: Mus musculus

<400> SEQUENCE: 28

Glu Val Gln Leu Gln Gln Ser Gly Pro Glu Leu Val Lys Pro Gly Ala
1               5                   10                  15
Ser Val Lys Val Ser Cys Lys Ala Ser Gly Tyr Ala Phe Ala Ser Tyr
                20                  25                  30
Asn Met Asn Trp Val Lys Gln Ser His Gly Lys Ser Leu Asp Trp Ile
            35                  40                  45
Gly Tyr Ile Asp Pro Tyr Asn Gly Gly Ser Ser Tyr Asn Leu Thr Phe
        50                  55                  60
Lys Gly Lys Ala Thr Leu Thr Val Asp Lys Ser Ser Thr Thr Ala Tyr
65                  70                  75                  80
Met His Leu Asn Ser Leu Thr Ser Glu Asp Ser Ala Val Tyr Tyr Cys
                85                  90                  95
Ala Arg Gly Tyr Gly Asn Tyr Lys Ala Trp Phe Ala Tyr Trp Gly Gln
            100                 105                 110
Gly Thr Leu Val Thr Val Ser Ala Ala Ser Thr Lys Gly Pro
        115                 120                 125

<210> SEQ ID NO 29
<211> LENGTH: 112
<212> TYPE: PRT
<213> ORGANISM: Mus musculus

<400> SEQUENCE: 29

Ser Ile Val Met Thr Pro Thr Pro Lys Phe Leu Leu Val Ser Ala Gly
1               5                   10                  15
Asp Arg Val Thr Ile Thr Cys Lys Ala Ser Gln Ser Val Ser Asn Asp
                20                  25                  30
Val Ala Trp Tyr Gln Gln Lys Pro Gly Gln Ser Pro Lys Leu Leu Ile
            35                  40                  45
Tyr Tyr Ala Ser Thr Arg Tyr Thr Gly Val Pro Asp Arg Phe Thr Gly
        50                  55                  60
Ser Gly Tyr Gly Thr Asp Phe Thr Phe Thr Ile Ser Thr Val Gln Ala
65                  70                  75                  80
Glu Asp Leu Ala Val Tyr Phe Cys Gln Gln Asp Tyr Ser Ser Leu Thr
                85                  90                  95
Phe Gly Ala Gly Thr Lys Leu Glu Leu Lys Arg Thr Val Ala Ala Pro
            100                 105                 110

<210> SEQ ID NO 30
<211> LENGTH: 5
<212> TYPE: PRT
<213> ORGANISM: Mus musculus

<400> SEQUENCE: 30

Ser Tyr Asn Met Asn
1               5

<210> SEQ ID NO 31
<211> LENGTH: 7
<212> TYPE: PRT
<213> ORGANISM: Mus musculus

<400> SEQUENCE: 31

Gly Tyr Ala Phe Ala Ser Tyr
```

```
<210> SEQ ID NO 32
<211> LENGTH: 8
<212> TYPE: PRT
<213> ORGANISM: Mus musculus

<400> SEQUENCE: 32

Gly Tyr Ala Phe Ala Ser Tyr Asn
1               5

<210> SEQ ID NO 33
<211> LENGTH: 17
<212> TYPE: PRT
<213> ORGANISM: Mus musculus

<400> SEQUENCE: 33

Tyr Ile Asp Pro Tyr Asn Gly Gly Ser Ser Tyr Asn Leu Thr Phe Lys
1               5                   10                  15

Gly

<210> SEQ ID NO 34
<211> LENGTH: 7
<212> TYPE: PRT
<213> ORGANISM: Mus musculus

<400> SEQUENCE: 34

Ser Gln Ser Val Ser Asn Asp
1               5

<210> SEQ ID NO 35
<211> LENGTH: 6
<212> TYPE: PRT
<213> ORGANISM: Mus musculus

<400> SEQUENCE: 35

Gln Ser Val Ser Asn Asp
1               5

<210> SEQ ID NO 36
<211> LENGTH: 126
<212> TYPE: PRT
<213> ORGANISM: Mus musculus

<400> SEQUENCE: 36

Gln Ile Gln Leu Gln Gln Ser Gly Pro Glu Leu Val Lys Pro Gly Ala
1               5                   10                  15

Ser Val Lys Val Ser Cys Lys Ala Ser Gly Tyr Ala Phe Ala Ser Tyr
                20                  25                  30

Asn Met Asn Trp Val Lys Gln Ser His Gly Lys Ser Leu Asp Trp Ile
            35                  40                  45

Gly Tyr Ile Asp Pro Tyr Asn Gly Gly Ser Ser Tyr Asn Leu Thr Phe
        50                  55                  60

Lys Gly Lys Ala Thr Leu Thr Val Asp Lys Ser Ser Thr Thr Ala Tyr
65                  70                  75                  80

Met His Leu Asn Ser Leu Thr Ser Glu Asp Ser Ala Val Tyr Tyr Cys
                85                  90                  95

Ala Arg Gly Tyr Gly Asn Tyr Lys Ala Trp Phe Ala Tyr Trp Gly Gln
                100                 105                 110

Gly Thr Leu Val Thr Val Ser Ala Ala Ser Thr Lys Gly Pro
            115                 120                 125
```

<210> SEQ ID NO 37
<211> LENGTH: 112
<212> TYPE: PRT
<213> ORGANISM: Mus musculus

<400> SEQUENCE: 37

Asp Val Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Thr Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Leu Thr
                85                  90                  95

Phe Gly Ala Gly Thr Lys Leu Glu Leu Lys Arg Thr Val Ala Ala Pro
            100                 105                 110

<210> SEQ ID NO 38
<211> LENGTH: 5
<212> TYPE: PRT
<213> ORGANISM: Mus musculus
<220> FEATURE:
<221> NAME/KEY: X
<222> LOCATION: (5)..(5)
<223> OTHER INFORMATION: X is any amino acid

<400> SEQUENCE: 38

Ser Tyr Asn Met Xaa
1               5

<210> SEQ ID NO 39
<211> LENGTH: 17
<212> TYPE: PRT
<213> ORGANISM: mus musculus
<220> FEATURE:
<221> NAME/KEY: X
<222> LOCATION: (9)..(9)
<223> OTHER INFORMATION: X is any amino acid
<220> FEATURE:
<221> NAME/KEY: X
<222> LOCATION: (13)..(13)
<223> OTHER INFORMATION: X is any amino acid
<220> FEATURE:
<221> NAME/KEY: X
<222> LOCATION: (14)..(14)
<223> OTHER INFORMATION: X is any amino acid

<400> SEQUENCE: 39

Tyr Ile Asp Pro Tyr Asn Gly Gly Xaa Ser Tyr Asn Xaa Xaa Phe Lys
1               5                   10                  15

Gly

<210> SEQ ID NO 40
<211> LENGTH: 9
<212> TYPE: PRT
<213> ORGANISM: Mus musculus
<220> FEATURE:
<221> NAME/KEY: X
<222> LOCATION: (9)..(9)
<223> OTHER INFORMATION: X is any amino acid

```
<400> SEQUENCE: 40

Tyr Ile Asp Pro Tyr Asn Gly Gly Xaa
1               5

<210> SEQ ID NO 41
<211> LENGTH: 13
<212> TYPE: PRT
<213> ORGANISM: Mus musculus
<220> FEATURE:
<221> NAME/KEY: X
<222> LOCATION: (3)..(3)
<223> OTHER INFORMATION: X is any amino acid

<400> SEQUENCE: 41

Gly Tyr Xaa Ala Ala Asn Tyr Lys Ala Trp Phe Ala Tyr
1               5                  10

<210> SEQ ID NO 42
<211> LENGTH: 11
<212> TYPE: PRT
<213> ORGANISM: Mus musculus
<220> FEATURE:
<221> NAME/KEY: X
<222> LOCATION: (7)..(7)
<223> OTHER INFORMATION: X is any amino acid

<400> SEQUENCE: 42

Lys Ala Ser Gln Ser Val Xaa Asn Asp Val Ala
1               5                  10

<210> SEQ ID NO 43
<211> LENGTH: 7
<212> TYPE: PRT
<213> ORGANISM: Mus musculus
<220> FEATURE:
<221> NAME/KEY: X
<222> LOCATION: (4)..(4)
<223> OTHER INFORMATION: X is any amino acid

<400> SEQUENCE: 43

Tyr Ala Ser Xaa Arg Tyr Thr
1               5

<210> SEQ ID NO 44
<211> LENGTH: 11
<212> TYPE: PRT
<213> ORGANISM: Mus musculus

<400> SEQUENCE: 44

Lys Ala Ser Gln Ser Val Ser Asn Asp Val Ala
1               5                  10

<210> SEQ ID NO 45
<211> LENGTH: 45
<212> TYPE: DNA
<213> ORGANISM: Homo sapiens

<400> SEQUENCE: 45
tacgactcac aagcttgccg ccaccatgtg tccccgagcc gcgcg            45

<210> SEQ ID NO 46
<211> LENGTH: 57
<212> TYPE: DNA
<213> ORGANISM: Homo sapiens

<400> SEQUENCE: 46
ccgccccgac tctagatcag tgatggtgat gatggtgctt gatccgacct tcaactg   57
```